US008591956B2

(12) United States Patent
Hadden et al.

(10) Patent No.: US 8,591,956 B2
(45) Date of Patent: Nov. 26, 2013

(54) METHOD OF INCREASING IMMUNOLOGICAL EFFECT

(75) Inventors: John W. Hadden, Cold Spring Harbor, NY (US); Theresa L. Whiteside-Nimick, Pittsburgh, PA (US); James E. Egan, Stony Brook, NY (US); Kathy L. Signorelli-Petrat, Springfield, VA (US); Harvey Brandwein, East Hills, NY (US)

(73) Assignee: IRX Therapeutics, Inc., New York, NY (US)

( * ) Notice: Subject to any disclaimer, the term of this patent is extended or adjusted under 35 U.S.C. 154(b) by 0 days.

(21) Appl. No.: 13/205,229

(22) Filed: Aug. 8, 2011

(65) Prior Publication Data

US 2012/0141512 A1 Jun. 7, 2012

Related U.S. Application Data

(62) Division of application No. 12/323,595, filed on Nov. 26, 2008, now Pat. No. 7,993,660.

(60) Provisional application No. 60/990,759, filed on Nov. 28, 2007, provisional application No. 61/056,925, filed on May 29, 2008.

(51) Int. Cl.
*A61K 35/26* (2006.01)
*C12N 5/00* (2006.01)
*C12N 5/02* (2006.01)

(52) U.S. Cl.
USPC ...................... 424/577; 435/372.3; 435/375

(58) Field of Classification Search
None
See application file for complete search history.

(56) References Cited

U.S. PATENT DOCUMENTS

| | | | |
|---|---|---|---|
| 4,079,127 A | 3/1978 | Goldstein et al. |
| 4,116,951 A | 9/1978 | Wang |
| 4,148,788 A | 4/1979 | Wang |
| 4,293,455 A | 10/1981 | Merrifield et al. |
| 4,353,821 A | 10/1982 | Birr et al. |
| 4,390,623 A | 6/1983 | Frabricius et al. |
| 4,406,830 A | 9/1983 | Fabricius et al. |
| 4,448,879 A | 5/1984 | Fabricius et al. |
| 4,464,355 A | 8/1984 | Fabricius et al. |
| 4,466,918 A | 8/1984 | Birr et al. |
| 4,470,926 A | 9/1984 | Birr et al. |
| 4,504,415 A | 3/1985 | Felix et al. |
| 4,612,365 A | 9/1986 | Birr et al. |
| 4,614,731 A | 9/1986 | Horecker |
| 4,659,694 A | 4/1987 | Horecker |
| 4,716,148 A | 12/1987 | Horecker |
| 4,910,296 A | 3/1990 | Birr et al. |
| 5,098,702 A | 3/1992 | Zimmerman et al. |
| 5,100,664 A | 3/1992 | Doyle et al. |
| 5,503,828 A | 4/1996 | Testa et al. |
| 5,503,841 A | 4/1996 | Doyle et al. |
| 5,632,983 A | 5/1997 | Hadden |
| 5,643,565 A | 7/1997 | Doyle et al. |
| 5,679,356 A | 10/1997 | Bonnem et al. |
| 5,698,194 A | 12/1997 | Hadden |
| 5,747,024 A | 5/1998 | Grabstein et al. |
| 5,788,963 A | 8/1998 | Murphy et al. |
| 5,800,810 A | 9/1998 | Doyle et al. |
| 5,849,307 A | 12/1998 | Metz et al. |
| 5,849,589 A | 12/1998 | Tedder et al. |
| 5,866,115 A | 2/1999 | Kanz et al. |
| 6,017,527 A | 1/2000 | Maraskovsky et al. |
| 6,060,068 A | 5/2000 | Doyle et al. |
| 6,274,378 B1 | 8/2001 | Steinman et al. |
| 6,350,589 B1 | 2/2002 | Morris et al. |
| 6,482,389 B1 | 11/2002 | Hadden |
| 6,896,879 B2 | 5/2005 | Talor |
| 6,977,072 B2 * | 12/2005 | Hadden ................. 424/85.2 |
| 7,153,499 B2 | 12/2006 | Hadden |
| 7,182,942 B2 | 2/2007 | Hadden |
| 7,731,945 B2 * | 6/2010 | Hadden ................. 424/85.1 |
| 7,993,660 B2 | 8/2011 | Hadden et al. |
| 2001/0053361 A1 | 12/2001 | Thompson et al. |
| 2002/0034494 A1 | 3/2002 | Vicari et al. |
| 2002/0058019 A1 | 5/2002 | Berenson et al. |
| 2002/0146397 A1 | 10/2002 | Hadden |
| 2002/0159953 A1 | 10/2002 | Hadden |
| 2003/0007955 A1 | 1/2003 | Rees et al. |
| 2003/0206885 A1 | 11/2003 | Hadden |
| 2004/0001829 A1 | 1/2004 | June et al. |
| 2004/0071658 A1 | 4/2004 | Hadden et al. |
| 2004/0136952 A1 | 7/2004 | Bhaskaran et al. |
| 2005/0008614 A1 | 1/2005 | Nieland et al. |

(Continued)

FOREIGN PATENT DOCUMENTS

CN 1106297 A 8/1995
EP 0 041 189 A1 12/1981

(Continued)

OTHER PUBLICATIONS

Egan et al ( J Immunother, 2007, v.30 pp. 624-633).*
Barrera et al Arch Otolar. Head Neck Surg, 2000, v.126, 345-351.*
Meneses et al ( International Immunol., 2003, v.3, pp. 1083-1091.*
Hadden et al ( I. J. of Immunol, 1995, v.17, pp. 821-828,.*
Albert et al., Dendritic cells acquire antigen from apoptotic cells and induce class I-restricted CTLs. Nature. Mar. 5, 1998; 392(6671):86-9.
Almand et al., Clinical significance of defective dendritic cell differentiation in cancer. Clin Cancer Res. May 6, 2000; (5):1755-66.
Alvarez et al., Human T cell growth factor. I. Optimal conditions for its production. J Immunol. Sep. 1979; 123(3):977-83.

(Continued)

*Primary Examiner* — Michail Belyavskyi
(74) *Attorney, Agent, or Firm* — Wolf, Greenfield & Sacks, P.C.

(57) ABSTRACT

A method of increasing immunological effect in a patient by administering an effective amount of a primary cell derived biologic to the patient, inducing immune production, blocking immune destruction, and increasing immunological effect in the patient. Methods of treating an immune target, treating a tumor, immune prophylaxis, and preventing tumor escape.

5 Claims, 41 Drawing Sheets

(56) References Cited

U.S. PATENT DOCUMENTS

| | | | |
|---|---|---|---|
| 2005/0124645 A1 | 6/2005 | Finkel | |
| 2005/0152874 A1 | 7/2005 | Hadden | |
| 2006/0120996 A1 | 6/2006 | Hadden | |
| 2006/0194242 A1 | 8/2006 | Hadden | |
| 2007/0025958 A1 | 2/2007 | Hadden | |
| 2007/0031372 A1 | 2/2007 | Hadden | |
| 2007/0041956 A1 | 2/2007 | Hadden | |
| 2007/0154399 A1 | 7/2007 | Hadden | |
| 2008/0220000 A1 | 9/2008 | Moore et al. | |
| 2009/0041797 A1 | 2/2009 | Davis et al. | |
| 2009/0180982 A1 | 7/2009 | Hadden, Sr. | |
| 2009/0181078 A1 | 7/2009 | Reed et al. | |
| 2009/0258395 A1 | 10/2009 | Fennington, Jr. et al. | |
| 2010/0047182 A1 | 2/2010 | Hadden | |
| 2010/0047205 A1 | 2/2010 | Hadden et al. | |
| 2010/0310469 A1 | 12/2010 | Hadden | |
| 2011/0044941 A1 | 2/2011 | Hadden | |
| 2011/0076249 A1 | 3/2011 | Hadden et al. | |
| 2011/0081313 A1 | 4/2011 | Hadden | |
| 2011/0110884 A1 | 5/2011 | Hadden et al. | |
| 2012/0064035 A1 | 3/2012 | Hadden et al. | |
| 2012/0244117 A1 | 9/2012 | Egan et al. | |

FOREIGN PATENT DOCUMENTS

| | | |
|---|---|---|
| EP | 0 433 765 A1 | 6/1991 |
| EP | 0 974 357 A1 | 1/2000 |
| EP | 0 789 588 B1 | 1/2005 |
| EP | 0 787 008 B1 | 1/2009 |
| EP | 1 653 912 B1 | 10/2011 |
| EP | 1 998 811 B1 | 10/2012 |
| JP | 8-511166 A | 11/1996 |
| JP | 11-504814 A | 5/1999 |
| JP | 2009-197032 A | 9/2009 |
| WO | 87/06830 A1 | 11/1987 |
| WO | 89/09619 A1 | 10/1989 |
| WO | 94/13314 A1 | 6/1994 |
| WO | 96/15800 A1 | 5/1996 |
| WO | 96/15808 A1 | 5/1996 |
| WO | 96/34956 A1 | 11/1996 |
| WO | 97/31119 A1 | 8/1997 |
| WO | 99/20788 A1 | 4/1999 |
| WO | 01/24771 A1 | 4/2001 |
| WO | 02/34119 A2 | 5/2002 |
| WO | 03/035004 A2 | 5/2003 |
| WO | 03/061566 A2 | 7/2003 |
| WO | 2005/025494 A2 | 3/2005 |
| WO | 2005/120550 A2 | 12/2005 |
| WO | 2007/136910 A2 | 11/2007 |
| WO | 2008/014220 A2 | 1/2008 |
| WO | 2008/101154 A2 | 8/2008 |
| WO | 2009/070639 A1 | 6/2009 |
| WO | WO 2009/137238 | 11/2009 |
| WO | WO 2009/146392 | 12/2009 |

OTHER PUBLICATIONS

Bajénoff et al., Stromal cell networks regulate lymphocyte entry, migration, and territoriality in lymph nodes. Immunity. Dec. 1, 1979; 25(6):989-1001.
Banchereau et al. Immunobiology of dendritic cells. Annu Rev Immunol. 2000;18:767-811.
Barrera et al., Clinical and pathological bio-responses induced with a cytokine mixture (IRX-2) in patients with oral cavity squamous cell carcinoma. Clinical and Applied Immunology Rev. 2001;1:181-5.
Barrera et al., Clinical and pathological responses induced by a neoadjuvant treatment with a cytokine mixture (IRX-2) in oral cavity squamous cell carcinoma of head and neck. Int J Immunorehab. 2000;2(3):29-32.
Barrera et al., Neoadjuvant immunological treatment with IRX-2 in patients with advanced oral cavity squamous cell carinoma of the head and neck induces clinical and histological responses. First World Congress on Head and Neck Oncology. 1998:1017-20.
Barrera et al., Nursing care makes a difference. Application of the Omaha System. Outcomes Manag. Oct.-Dec. 2003; 7(4):181-5.
Belldegrun et al., Adoptive immunotherapy of urologic tumors. Urologic Oncology. Cancer Treatment and Research. 1989;46:213-33.
Belldegrun et al., Human tumor infiltrating lymphocytes. Analysis of lymphokine mRNA expression and relevance to cancer immunotherapy. J Immunol. Jun. 15, 1989; 142(12):4520-6.
Bellone et al., Cancer immunotherapy: synthetic and natural peptides in the balance. Immunol Today. Oct. 20, 1999; (10):457-62.
Bellone et al., Processing of engulfed apoptotic bodies yields T cell epitopes. J Immunol. Dec. 1, 1997; 159(11):5391-9.
Bender et al., Improved methods for the generation of dendritic cells from nonproliferating progenitors in human blood. J Immunol Methods. Sep. 27, 1996; 196(2):121-35.
Berd et al., Effect of low dose cyclophosphamide on the immune system of cancer patients: reduction of T-suppressor function without depletion of the CD8+ subset. Cancer Res. Jun. 15, 1987; 47(12):3317-21.
Berd et al., Potentiation of human cell-mediated and humoral immunity by low-dose cyclophosphamide. Cancer Res. Nov. 1984; 44(11):5439-43.
Berd, Low doses of chemotherapy to inhibit suppressor T cells. Immunity to Cancer II. 1989; 288:449-58.
Beuth et al., Thymosin alpha(1) application augments immune response and down-regulates tumor weight and organ colonization in BALB/c-mice. Cancer Lett. Oct. 16, 2000; 159(1):9-13.
Borden, Interferons: rationale for clinical trials in neoplastic disease. Ann Intern Med. Sep. 1979; 91(3):472-9. Review.
Borysiewicz et al., A recombinant vaccinia virus encoding human papillomavirus types 16 and 18, E6 and E7 proteins as immunotherapy for cervical cancer. Lancet. Jun. 1, 1996; 347(9014):1523-7.
Brandwein, IRX-2: a natural cytokine stimulant for cancer vaccines. Session V: Strategies for immunization. Cancer Immunol Immunotherapy. Mar. 2003; 52:S17-18, 30.
Cella et al., Inflammatory stimuli induce accumulation of MHC class II complexes on dendritic cells. Nature. Aug. 21, 1997; 388(6644):782-7.
Cella et al., Ligation of CD40 on dendritic cells triggers production of high levels of interleukin-12 and enhances T cell stimulatory capacity: T-T help via APC activation. J Exp Med. Aug. 1, 1996; 184(2):747-52.
Chang et al., Overview of interleukin-2 as an immunotherapeutic agent. Semin Surg Oncol. 1989; 5(6):385-90. Review.
Chaux et al, Inflammatory cells infiltrating human colorectal carcinomas express HLA class II but not B7-1 and B7-2 costimulatory molecules of the T-cell activation. Lab Invest. May 1996; 74(5):975-83.
Chilson et al., Mitogenic lectins bind to the antigen receptor on human lymphocytes. Eur J Immunol. Feb. 19, 1989; (2):389-96.
Chirigos et al., Immunotherapeutic agents: their role in cellular immunity and their therapeutic potential. Springer Semin Immunopathol. 1985; 8(4):327-46.
Cirelli et al., Interferons in human papillomavirus infections. Antiviral Res. Jul. 24, 1994; (2-3):191-204.
Clerici et al., An Occam's razor approach to the immunopathogenesis of HIV infection. AIDS. 1995;9 Suppl A:S33-40.
Cohen et al., Pronounced acute immunosuppression in vivo mediated by HIV Tat challenge. Proc Natl Acad Sci U S A. Sep. 14, 1999; 96(19):10842-7.
Cortesina et al., Interleukin-2 injected around tumor-draining lymph nodes in head and neck cancer. Head Neck. Mar.-Apr. 13, 1991; (2):125-31.
Cortesina et al., Temporary regression of recurrent squamous cell carcinoma of the head and neck is achieved with a low but not with a high dose of recombinant interleukin 2 injected perilymphatically. Br J Cancer. Mar. 1994; 69(3):572-6.
Cortesina et al., Treatment of recurrent squamous cell carcinoma of the head and neck with low doses of interleukin-2 injected perilymphatically. Cancer. Dec. 15, 1988; 62(12):2482-5.
Cowens et al, Inhibition of the development of suppressor cells in culture by 4-hydroperoxycyclophosphamide. J Immunol. 1984;132:95-100.

(56) References Cited

OTHER PUBLICATIONS

Cozzolino et al., Characterization of cells from invaded lymph nodes in patients with solid tumors. Lymphokine requirement for tumor-specific lymphoproliferative response. J Exp Med. Aug. 1, 1987; 166(2):303-18.
Cross et al., Administration of a prostaglandin synthetase inhibitor associated with an increased immune cell infiltrate in squamous cell carcinoma of the head and neck. Arch Otolaryngol Head Neck Surg. May 1992; 118(5):526-8.
Czystowska et al., Mechanisms of T-cell protection from death by IRX-2: a new immunotherapeutic. Cancer Immunol Immunother. Apr. 2011; 60(4):495-506. doi: 10.1007/s00262-010-0951-9. Epub Dec. 23, 2010.
Dallal et al., The dendritic cell and human cancer vaccines. Curr Opin Immunol. Oct. 12, 2000; (5):583-8.
De Stefani et al., Improved survival with perilymphatic interleukin 2 in patients with resectable squamous cell carcinoma of the oral cavity and oropharynx. Cancer. Jul. 1, 2002; 95(1):90-7.
De Vries et al., Effective migration of antigen-pulsed dendritic cells to lymph nodes in melanoma patients is determined by their maturation state. Cancer Res. Jan. 1, 2003; 63(1):12-7.
Deans et al., CD45R as a primary signal transducer stimulating IL-2 and IL-2R mRNA synthesis by CD3-4-8-thymocytes. J Immunol. Oct. 15, 1989; 143(8):2425-30.
Deepe et al., Pharmacological modulation of suppressor cell activity in mice with disseminated histoplasmosis. Infect Immun. Jul. 1983; 41(1):114-20.
Den Otter et al., Local therapy of cancer with free IL-2. Cancer Immunol Immunother. Jul. 2008; 57(7):931-50. doi: 10.1007/s 00262-008-0455-z.
Dueñas-Gonzalez et al., A pilot study of perilymphatic leukocyte cytokine mixture (IRX-2) as neoadjuvant treatment for early stage cervical carcinoma. Int Immunopharmacol. Jun. 2, 2002; (7):1007-16.
Dunn et al., Dendritic cells and HNSCC: a potential treatment option? Oncology Reports. 2005; 13:3-10.
Ehrke, Immunomodulation in cancer therapeutics. Int Immunopharmacol. Aug. 2003; 3(8):1105-19.
Favalli et al., Modulation of natural killer activity by thymosin alpha 1 and interferon. Cancer Immunol Immunother. 1985; 20(3):189-92.
Ferraro et al., Co-delivery of PSA and PSMA DNA vaccines with electroporation induces potent immune responses. Hum Vaccin. Jan.-Feb. 2011; 7 Suppl:120-7. Epub Jan. 1, 2011.
Forni et al., Interleukin 2 activated tumor inhibition in vivo depends on the systemic involvement of host immunoreactivity. J Immunol. Jun. 1, 1987; 138(11):4033-41.
Frillingos et al., Appearance of thymosin alpha 1 in supernatants of monocytes incubated with prothymosin alpha. Arch Biochem Biophys. Jul. 1992; 296(1):256-63.
Gabrilovich et al., Decreased antigen presentation by dendritic cells in patients with breast cancer. Clin Cancer Res. Mar. 1997; 3(3):483-90.
Gabrilovich et al., Dendritic cells in antitumor immune responses. I. Defective antigen presentation in tumor-bearing hosts. Cell Immunol. May 25, 1996; 170(1):101-10.
Gabrilovich et al., Production of vascular endothelial growth factor by human tumors inhibits the functional maturation of dendritic cells. Nat Med. Oct. 1996; 2(10):1096-103.
Gabrilovich et al., Vascular endothelial growth factor inhibits the development of dendritic cells and dramatically affects the differentiation of multiple hematopoietic lineages in vivo. Blood. Dec. 1, 1998; 92(11):4150-66.
Gallo et al., Cyclooxygenase-2 pathway correlates with VEGF expression in head and neck cancer. Implications for tumor angiogenesis and metastasis. Neoplasia. Jan.-Feb. 2001; 3(1):53-61.
Galon et al., Type, density, and location of immune cells within human colorectal tumors predict clinical outcome. Science. Sep. 29, 2006; 313(5795):1960-4.
Garaci et al., Thymosin alpha 1 in the treatment of cancer: from basic research to clinical application. Int J Immunopharmacol. Dec. 2000; 22(12):1067-76. Review.
Garaci, Thymosin alpha1: a historical overview. Ann N Y Acad Sci. Sep. 2007; 1112:14-20. Epub Jun. 13, 2007.
Gearing et al., Production and assay of the interleukins. J Immunol Methods. Oct. 24, 1985; 83(1):1-27.
Gillis et al., T cell growth factor: parameters of production and a quantitative microassay for activity. J Immunol. Jun. 1978; 120(6):2027-32.
Goldstein et al., The role of interferon in cancer therapy: a current perspective. CA Cancer J Clin. Sep.-Oct. 1988; 38(5):258-77.
Goldstein et al., Thymosin alpha1: isolation and sequence analysis of an immunologically active thymic polypeptide. Proc Natl Acad Sci U S A. Feb. 1977; 74(2):725-9.
Goldstein, Thymosin α1: chemistry, mechanism of action and clinical applications. Combination Therapies. Plenum Press. 1993; 2:39-48.
Gollapudi et al, Effect of ciprofloxacin on mitogen-stimulated lymphocyte proliferation. Antimicrob Agents Chemother. Feb. 1986; 29(2):337-8.
Hadden et al., A trial of IRX-2 in patients with squamous cell carcinomas of the head and neck. Int Immunopharmacol. Aug. 2003; 3(8):1073-81.
Hadden et al., Immunopharmacologic bases of immunotherapy. Clin Physiol Biochem. 1985; 3(2-3):111-9. Review.
Hadden et al., Immunopharmacology. Immunomodulation and immunotherapy. JAMA. Nov. 25, 1992; 268(20):2964-9.
Hadden et al., Interleukins and contrasuppression induce immune regression of head and neck cancer. Arch Otolaryngol Head Neck Surg. Apr. 1994; 120(4):395-403.
Hadden et al., IRX-2 and thymosin alphal (Zadaxin) increase T lymphocytes in T lymphocytopenic mice and humans. Ann N Y Acad Sci. Sep. 2007; 1112:245-55. Epub Jun. 28, 2007.
Hadden et al., Lymphocyte blast transformation. I. Demonstration of adrenergic receptors in human peripheral lymphocytes. Cell Immunol. Dec. 1970; 1(6):583-95.
Hadden et al., Mixed interleukins and thymosin fraction V synergistically induce T lymphocyte development in hydrocortisone-treated aged mice. Cell Immunol. Oct. 1, 1992; 144(1):228-36.
Hadden et al., Strategies of immune reconstitution: effects of lymphokines on murine T cell development in vitro and in vivo. Life Sci. 1989; 44(13):v-xii.
Hadden et al., The characterization of immunotherapeutic agents. Immunopharmacol Reviews. Plenum Press. New York. 1990; 1:1-64.
Hadden, Aspects of the immunopharmacology of thymosin alpha-1. Clinical Applied Reviews. Mar. 2001; 1(3-4):187-91.
Hadden, Combination immunotherapy. Intl Immunopharm. 2003; 3:1049-50.
Hadden, Immunodeficiency and cancer: prospects for correction. Int Immunopharmacol. Aug. 2003; 3(8):1061-71.
Hadden, Immunology of Head and Neck Cancer. Contemporary Issues in Oral Cancer. New York. Oxford University Press. 2000:72-95.
Hadden, Immunology of head and neck cancer: prospects for immunotherapy. Clin Immunotherapy. 1995; 3:362-85.
Hadden, Immunopharmacology. Immunomodulation and immunotherapy. JAMA. Nov. 27, 1987; 258(20):3005-10.
Hadden, Immunostimulants. Immunol Today. Jun. 1993; 14(6):275-80. Review.
Hadden, Immunotherapy of human immunodeficiency virus infection. TIPS review. 1991; 12:107-11.
Hadden, T-cell adjuvants. Int J Immunopharmacol. Sep. 1994; 16(9):703-10.
Hadden, The immunology and immunotherapy of breast cancer: an update. Int J Immunopharmacol. Feb. 1999; 21(2):79-101.
Hadden, The immunopharmacology of head and neck cancer: an update. Int J Immunopharmacol. Nov.-Dec. 1997; 19(11-12):629-44.
Hadden, The treatment of zinc deficiency is an immunotherapy. Int J Immunopharmacol. Sep. 1995; 17(9):697-701.
Hadden, Thymic endocrinology. Ann N Y Acad Sci. May 1, 1998; 840:352-8.

(56) References Cited

OTHER PUBLICATIONS

Hadden, Thymic endocrinology. Int J Immunopharmacol. Apr. 1992; 14(3):345-52. Review.

Hank et al., Monoclonal antibodies, cytokines and fusion proteins in the treatment of malignant disease. Cancer Chemother Biol Response Modif. 1999; 18:210-22.

Hart, Dendritic cells: unique leukocyte populations which control the primary immune response. Blood. Nov. 1, 1997; 90(9):3245-87.

Hengst et al., Cooperation between cyclophosphamide tumoricidal activity and host antitumor immunity in the cure of mice bearing large MOPC-315 tumors. Cancer Res. Jun. 1981; 41(6):2163-7.

Hengst et al., Importance of timing in cyclophosphamide therapy of MOPC-315 tumor-bearing mice. Cancer Res. Jul. 1980; 40(7):2135-41.

Hillman et al., Systemic treatment with interleukin-4 induces regression of pulmonary metastases in a murine renal cell carcinoma model. Cell Immunol. Feb. 1995; 160(2):257-63.

Hirsch et al., Immunostimulation of patients with head and neck cancer. In vitro and preliminary clinical experiences. Arch Otolaryngol. May 1983; 109(5):298-301.

Hoffmann et al., Alterations in the frequency of dendritic cell subsets in the peripheral circulation of patients with squamous cell carcinomas of the head and neck. Clin Cancer Res. Jun. 2002; 8(6):1787-93.

Holtl et al., Immunotherapy of metastatic renal cell carcinoma with tumor lysate-pulsed autologous dendritic cells. Clin Cancer Res. Nov. 2002; 8(11):3369-76.

Hwu et al., The genetic modification of T cells for cancer therapy: an overview of laboratory and clinical trials. Cancer Detect Prev. 1994; 18(1):43-50. Review.

Hwu et al., The use of gene-modified tumor-infiltrating lymphocytes for cancer therapy. Ann N Y Acad Sci. May 31, 1994; 716:188-97; discussion 197-203. Review.

Johnston-Early et al., Delayed hypersensitivity skin testing as a prognostic indicator in patients with small cell lung cancer. Cancer. Oct. 15, 1983; 52(8):1395-400.

Jordan et al., Optimal analysis of composite cytokine responses during alloreactivity. J Immunol Methods. Feb. 1, 2002; 260(1-2):1-14.

June et al., Evidence for the involvement of three distinct signals in the induction of IL-2 gene expression in human T lymphocytes. J Immunol. Jul. 1, 1989; 143(1):153-61.

Kaech et al., Effector and memory T-cell differentiation: implications for vaccine development. Nat Rev Immunol. Apr. 2002; 2(4):251-62.

Kalinski et al., Prostaglandin E(2) is a selective inducer of interleukin-12 p40 (IL-12p40) production and an inhibitor of bioactive IL-12p70 heterodimer. Blood. Jun. 1, 2001; 97(11):3466-9.

Kameda et al., Mixed lymphokines in low dose prolong life in cyclophosphamide-treated melanoma-bearing mice. Int J Immunother. 1992; 8:1-5.

Kaminuma et al., Interleukin-5 production by peripheral blood mononuclear cells of asthmatic patients is suppressed by T-440: relation to phosphodiesterase inhibition. J Pharmacol Exp Ther. Oct. 1996; 279(1):240-6.

Katsuyuki et al., Clinical trials of immunotherapy for advanced prostate cancer. Urologic Oncology. 2000; 5:265-73.

Kavanaugh et al., Immunologic dysfunction in cancer. Hematol Oncol Clin North Am. Aug. 1996; 10(4):927-51.

Kidd, Th1/Th2 balance: the hypothesis, its limitations, and implications for health and disease. Altern Med Rev. Aug. 2003; 8(3):223-46.

Kleindienst et al., Endogenous dendritic cells are required for amplification of T cell responses induced by dendritic cell vaccines in vivo. J Immunol. Mar. 15, 2003; 170(6):2817-23.

Koopman et al., Reversal of human papillomavirus immune escape using IRX-2 and a toll-like receptor 3 agonist. Online. Available at http://scripties.umcg.eldoc.ub.rug.nl/root/geneeskunde/2010/KoopmanMaaike/. Jan 1, 2011. Retrieved from the Internet on Jan. 22, 2011.

Kovacs et al., Increases in CD4 T lymphocytes with intermittent courses of interleukin-2 in patients with human immunodeficiency virus infection. A preliminary study. N Engl J Med. Mar. 2, 1995; 332(9):567-75.

Lafferty et al., Immunological induction of T lymphocytes: role of antigen and the lymphocyte costimulator. Blood Cells 1978;4(3):395-406.

Lahiri et al., Engagement of TLR signaling as adjuvant: towards smarter vaccine and beyond. Vaccine. Dec. 9, 2008; 26(52):6777-83.

Langenkamp et al., Kinetics of dendritic cell activation: impact on priming of TH1, TH2 and nonpolarized T cells. Nat Immunol. Oct. 2000; 1(4):311-6.

Lanzavecchia et al., Understanding the generation and function of memory T cell subsets. Curr Opin Immunol. Jun. 2005; 17(3):326-32.

Lopez et al., Biochemotherapy with thymosin alpha 1, interleukin-2 and dacarbazine in patients with metastatic melanoma: clinical and immunological effects. Ann Oncol. Oct. 1994; 5(8):741-6.

López-Rodríguez et al., Interleukin-2 killer cells: in vitro evaluation of combination with prothymosin alpha. Lymphokine Cytokine Res. Jun. 1994; 13(3):175-82.

Lou et al., Dendritic cells strongly boost the antitumor activity of adoptively transferred T cells in vivo. Cancer Res. Sep. 15, 2004; 64(18):6783-90.

Maass et al., Priming of tumor-specific T cells in the draining lymph nodes after immunization with interleukin 2-secreting tumor cells: three consecutive stages may be required for successful tumor vaccination. Proc Natl Acad Sci U S A. Jun. 6, 1995; 92(12):5540-4.

Mackall et al., Age, thymopoiesis, and CD4+ T-lymphocyte regeneration after intensive chemotherapy N Engl J Med. Jan. 19, 1995; 332(3):143-9.

Mackall, T-cell immunodeficiency following cytotoxic antineoplastic therapy: a review. Stem Cells. 2000; 18(1):10-8.

MacLean et al., Enhancing the effect of THERATOPE STn-KLH cancer vaccine in patients with metastatic breast cancer by pretreatment with low-dose intravenous cyclophosphamide. J Immunother Emphasis Tumor Immunol. Jul. 1996; 19(4):309-16.

Mantovani et al., Macrophage polarization: tumor-associated macrophages as a paradigm for polarized M2 mononuclear phagocytes. Trends Immunol. Nov. 2002; 23(11):549-55. Review.

Maric et al., Immunostimulatory activity of prothymosin-alpha in senescence. Ann N Y Acad Sci. 1991; 621:148-58.

Maric et al., In vivo effect of prothymosin-alpha 1 on humoral and cell-mediated immune responses in the young rat. Int J Neurosci. Jul. 1991; 59(1-3):135-42.

Masek et al., Neuroendocrine immune interactions in health and disease. Int Immunopharmacol. Aug. 2003; 3(8):1235-46.

Mastino et al., Combination therapy with thymosin alpha 1 potentiates the anti-tumor activity of interleukin-2 with cyclophosphamide in the treatment of the Lewis lung carcinoma in mice. Int J Cancer. Feb. 1, 1992; 50(3):493-9.

Mastino et al., Thymosin alpha 1 potentiates interleukin 2-induced cytotoxic activity in mice. Cell Immunol. Mar. 1991; 133(1):196-205.

Mastrangelo et al., Active specific immunization in the treatment of patients with melanoma. Semin Oncol. Dec. 1996; 23(6):773-81.

Mattijssen et al., Clinical and immunopathological results of a phase II study of perilymphatically injected recombinant interleukin-2 in locally far advanced, nonpretreated head and neck squamous cell carcinoma. J Immunother (1991). Feb. 1991; 10(1):63-8.

Mempel et al., Rulers over randomness: stroma cells guide lymphocyte migration in lymph nodes. Immunity. Dec. 2006; 25(6):867-9.

Meneses et al., Histologic findings in patients with head and neck squamous cell carcinoma receiving perilymphatic natural cytokine mixture (IRX-2) prior to surgery. Arch Pathol Lab Med. May 1998; 122(5):447-54.

Middel et al., Sinus histiocytosis with massive lymphadenopathy: evidence for its relationship to macrophages and for a cytokine-related disorder. Histopathology. Dec. 1999; 35(6):525-33.

Mikyskováet al., Local cytokine treatment of HPV16-associated tumors results in inhibition of their lung metastases. Clin Exp Metastasis. 2001; 18(7):581-7.

Mitchell et al., Promotion of human T lymphocyte proliferation by IL-4. J Immunol. Mar. 1, 1989; 142(5):1548-57.

Mokyr et al., Role of antitumor immunity in cyclophosphamide-induced rejection of subcutaneous nonpalpable MOPC-315 tumors. Cancer Res. Mar. 1982; 42(3):974-9.

(56) References Cited

OTHER PUBLICATIONS

Moody et al., Thymosin alpha 1 down-regulates the growth of human non-small cell lung cancer cells in vitro and in vivo. Cancer Res. Nov. 1, 1993; 53(21):5214-8.
Morgan et al., Selective in vitro growth of T lymphocytes from normal human bone marrows. Science. Sep. 10, 1976; 193(4257):1007-8.
Mule, Mechanistic aspects of successful immunotherapy of established pulmonary metastases by the systemic administration of high-dose recombinant interleukin-2. Prog Clin Biol Res. 1987; 244:79-91.
Murphy et al., Infusion of dendritic cells pulsed with HLA-A2-specific prostate-specific membrane antigen peptides: a phase II prostate cancer vaccine trial involving patients with hormone-refractory metastatic disease. Prostate. Jan. 1, 1999; 38(1):73-8.
Musiani et al., Effect of low doses of interleukin-2 injected perilymphatically and peritumorally in patients with advanced primary head and neck squamous cell carcinoma. J Biol Response Mod. Dec. 1989; 8(6):571-8.
Naylor et al., Preclinical and clinical studies on immunogenicity and safety of the HIV-1 p17-based synthetic peptide AIDS vaccine—HGP-30-KLH. Int J Immunopharmacol. 1991; 13 Suppl 1:117-27.
Naylor et al., Enhancement of Peptide Specific DTH with Combination Cytokines. Presented CSHL Meeting Dec. 4-7, 2003. Molecular Approaches to Vaccine Design. p. 28.
Naylor et al., Immunopharmacology of thymosin alpha1 and cytokine synergy. Ann N Y Acad Sci. Sep. 2007; 1112:235-44. Epub Jun. 13, 2007.
Naylor et al., IRX-2 increases the T cell-specific immune response to protein/peptide vaccines. Vaccine. Oct. 8, 2010; 28(43):7054-62. Epub Aug. 13, 2010.
Naylor et al., Preclinical studies with an IRX-2 enhanced prostate vaccine. J Urology. 2008; 179(4):45.
Naylor et al., Preclinical studies with IRX-2 and thymosin alpha1 in combination therapy. Ann N Y Acad Sci. Apr. 2010; 1194:162-8.
Naylor et al., T cell targeted immune enhancement yields effective T cell adjuvants. Int Immunopharmacol. Aug. 2003; 3(8):1205-15.
Nohria et al., Cytokines as potential vaccine adjuvants. Biotherapy. 1994; 7(3-4):261-9.
O'Hagan et al., Recent developments in adjuvants for vaccines against infectious diseases. Biomol Eng. Oct. 15, 2001; 18(3):69-85.
Overwijk et al., Creating therapeutic cancer vaccines: notes from the battlefield. Trends Immunol. Jan. 2001; 22(1):5-7.
Paetkeau et al., Proliferation of murine thymic lymphocytes in vitro is mediated by the concanavalin A-induced release of a lymphokine (costimulator). J Immunol. Oct. 1976; 117(4):1320-4.
Panje, Regression of head and neck carcinoma with a prostaglandin-synthesis inhibitor. Arch Otolaryngol. Nov. 1981; 107(11):658-63.
Pulley et al., Intravenous, intralesional and endolymphatic administration of lymphokines in human cancer. Lymphokine Res. 1986; 5 Suppl 1:S157-63.
Randolph, Dendritic cell migration to lymph nodes: cytokines, chemokines, and lipid mediators. Semin Immunol. Oct. 2001; 13(5):267-74.
Rapidis et al., Immunotherapy of head and neck cancer: current and future considerations. J Oncol. 2009; 2009:346345. doi: 10.1155/2009/346345. Epub Aug. 9, 2009. 11 pages.
Rasi et al., Anti-tumor effect of combined treatment with thymosin alpha 1 and interleukin-2 after 5-fluorouracil in liver metastases from colorectal cancer in rats. Int J Cancer. Jun. 1, 1994; 57(5):701-5.
Rasi et al., Combined treatment with thymosin-alpha1 and low dose interferon-alpha after dacarbazine in advanced melanoma. Melanoma Res. Apr. 2000; 10(2):189-92.
Ridgway, The first 1000 dendritic cell vaccinees. Cancer Invest. 2003; 21(6):873-86.
Riesbeck et al., Limited effects of temafloxacin compared with ciprofloxacin on T-lymphocyte function. Antimicrob Agents Chemother. Apr. 1994; 38(4):879-82.
Riesenbeck et al., Superinduction of cytokine gene transcription by ciprofloxacin. J Immunol. Jul. 1, 1994; 153(1):343-52.
Rogers et al., CD28, Ox-40, LFA-1, and CD4 modulation of Th1/Th2 differentiation is directly dependent on the dose of antigen. J Immunol. Mar. 15, 2000; 164(6):2955-63.
Romani et al., Generation of mature dendritic cells from human blood. An improved method with special regard to clinical applicability. J Immunol Methods. Sep. 27, 1996; 196(2):137-51.
Rosenberg et al., A progress report on the treatment of 157 patients with advanced cancer using lymphokine-activated killer cells and interleukin-2 or high-dose interleukin-2 alone. N Engl J Med. Apr. 9, 1987; 316(15):889-97.
Rosenberg et al., Cancer immunotherapy: moving beyond current vaccines. Nat Med. Sep. 2004; 10(9):909-15.
Rosenberg et al., Observations on the systemic administration of autologous lymphokine-activated killer cells and recombinant interleukin-2 to patients with metastatic cancer. N Engl J Med. Dec. 5, 1985; 313(23):1485-92.
Rosenberg, Immunotherapy of cancer by systemic administration of lymphoid cells plus interleukin-2. J Biol Response Mod. Oct. 1984; 3(5):501-11.
Rosenberg, The development of new immunotherapies for the treatment of cancer using interleukin-2. A review. Ann Surg. Aug. 1988; 208(2):121-35. Review.
Saha et al., Zinc induces thymulin secretion from human thymic epithelial cells in vitro and augments splenocyte and thymocyte responses in vivo. Int J Immunopharmacol. Sep. 1995; 17(9):729-33.
Saito et al., Spontaneous ex vivo apoptosis of peripheral blood mononuclear cells in patients with head and neck cancer. Clin Cancer Res. Jun. 1999; 5(6):1263-73.
Sallusto et al., Dendritic cells use macropinocytosis and the mannose receptor to concentrate macromolecules in the major histocompatibility complex class II compartment: downregulation by cytokines and bacterial products. J Exp Med. Aug. 1, 1995; 182(2):389-400.
Sallusto et al., Efficient presentation of soluble antigen by cultured human dendritic cells is maintained by granulocyte/macrophage colony-stimulating factor plus interleukin 4 and downregulated by tumor necrosis factor alpha. J Exp Med. Apr. 1, 1994; 179(4):1109-18.
Schuler-Thurner et al., Rapid induction of tumor-specific type 1 T helper cells in metastatic melanoma patients by vaccination with mature, cryopreserved, peptide-loaded monocyte-derived dendritic cells. J Exp Med. May 20, 2002; 195(10):1279-88.
Schuloff, Thymic peptide hormones: basic properties and clinical applications in cancer. Crit Rev Oncol Hematol. 1985; 3(4):309-76. Review.
Scott et al., Cell-mediated immune response to human papillomavirus infection. Clin Diagn Lab Immunol. Mar. 2001; 8(2):209-20.
Scott et al., Th1 Cytokine Patterns in Cervical Human Papillomavirus Infection. Clin Diagn Lab Immunol. Sep. 1999; 6(5): 751-5.
Silecchia et al., Efficacy of repeated cycles of chemo-immunotherapy with thymosin alpha1 and interleukin-2 after intraperitoneal 5-fluorouracil delivery. Cancer Immunol Immunother. Jul. 1999; 48(4):172-8.
Sozzani et al., Differential regulation of chemokine receptors during dendritic cell maturation: a model for their trafficking properties. J Immunol. Aug. 1, 1998; 161(3):1083-6.
Steinman et al., Avoiding horror autotoxicus: the importance of dendritic cells in peripheral T cell tolerance. Proc Natl Acad Sci U S A. Jan. 8, 2002; 99(1):351-8. Epub Jan. 2, 2002.
Steinman, The dendritic cell system and its role in immunogenicity. Annu Rev Immunol. 1991; 9:271-96.
Syrjänen, Human papillomavirus (HPV) in head and neck cancer. J Clin Virol. Mar. 2005; 32 Suppl 1:S59-66.
Tagawa, Cytokine therapy for cancer. Curr Pharm Des. Apr. 6, 2000; (6):681-99.
Talmage et al., Activation of cytotoxic T cells by nonstimulating tumor cells and spleen cell factor(s). Proc Natl Acad Sci U S A. Oct. 1977; 74(10):4610-4.
Tas et al., Depressed monocyte polarization and clustering of dendritic cells in patients with head and neck cancer: in vitro restoration of this immunosuppression by thymic hormones. Cancer Immunol Immunother. 1993; 36(2):108-14.

(56) References Cited

OTHER PUBLICATIONS

Thurman et al., Comparative evaluation of multiple lymphoid and recombinant human interleukin-2 preparations. J Biol Response Mod. Feb. 1986; 5(1):85-107.

Tjoa et al., Development of dendritic-cell based prostate cancer vaccine. Immunol Lett. Sep. 15, 2000; 74(1):87-93.

Tjoa et al., Evaluation of phase I/II clinical trials in prostate cancer with dendritic cells and PSMA peptides. Prostate. Jun. 15, 1998; 36(1):39-44.

Tzehoval et al., Thymosins alpha 1 and beta 4 potentiate the antigen-presenting capacity of macrophages. Immunopharmacology. Sep.-Oct. 1989; 18(2):107-13.

Valente et al., Infiltrating leukocyte populations and T-lymphocyte subsets in head and neck squamous cell carcinomas from patients receiving perilymphatic injections of recombinant interleukin 2. A pathologic and immunophenotypic study. Mod Pathol. Nov. 1990; 3(6):702-8.

Van Den Eynde et al., T cell defined tumor antigens. Curr Opin Immunol. Oct. 1997; 9(5):684-93.

Van Lier et al, Immobilized anti-CD3 monoclonal antibodies induce accessory cell-independent lymphokine production, proliferation and helper activity in human T lymphocytes. Immunology. Sep. 1989; 68(1):45-50.

Verastegui et al. Immunological approach in the evaluation of regional lymph nodes of patients with squamous cell carcinoma of the head and neck. Clin Immunol. Jan. 2002; 102(1):37-47.

Verastegui et al., A natural cytokine mixture (IRX-2) and interference with immune suppression induce immune mobilization and regression of head and neck cancer. Int J Immunopharmacol. Nov.-Dec. 1997; 19(11-12):619-27.

Verastegui et al., Long-term immune dysfunction after radiotherapy to the head and neck area. Int Immunopharmacol. Aug. 2003; 3(8):1093-1104.

Verwilghen et al., Differences in the stimulating capacity of immobilized anti-CD3 monoclonal antibodies: variable dependence on interleukin-1 as a helper signal for T-cell activation. Immunology. Feb. 1991; 72(2):269-76.

Vine et al., T4 cell activation by immobilized phytohemagglutinin: differential capacity to induce IL-2 responsiveness and IL-2 production. J Immunol. Oct. 15, 1988; 141(8):2593-600.

Wang et al., Human tumor antigens for cancer vaccine development. Immunol Rev. Aug. 1999; 170:85-100.

Webb et al., Mitogen-induced human lymphocyte activation in serum-free medium. Clin Immunol Immunopathol. Apr. 1973; 1(3):304-10.

Whiteside et al., Antigen-processing machinery in human dendritic cells: up-regulation by maturation and down-regulation by tumor cells. J Immunol. Aug. 1, 2004; 173(3):1526-34.

Whiteside et al., Evidence for local and systemic activation of immune cells by peritumoral injections of interleukin 2 in patients with advanced squamous cell carcinoma of the head and neck. Cancer Res. Dec. 1, 1993; 53(23):5654-62.

Whiteside, Immunobiology and immunotherapy of head and neck cancer. Curr Oncol Rep. Jan. 2001; 3(1):46-55.

\* cited by examiner

In Vivo Dose Response for IRX-2

Peptide Specific DTH Response in the Conjugate Vaccine Model

Day 0 and Day 21

IRX-2 Increases Regional Lymph Node Size, T-Cell Area and Density and Reverses Sinus Histiocytosis IRX-2 Stimulates Killer T-Cell Infiltration that Causes Tumor Destruction

METHOD OF INCREASING IMMUNOLOGICAL EFFECT

BACKGROUND OF THE INVENTION (1) Field of the Invention

The present invention relates to therapy of the immune system. In particular, the present invention relates to a primary cell derived biologic and methods of using the same to modify potentiation of the immune system.

(2) Description of Related Art

In a functioning and competent immune system, immature dendritic cells ingest antigens and migrate to the lymph nodes, where they mature. The resulting mature dendritic cells are then able to activate naïve T cells, creating antigen-specific cytotoxic T cells that then proliferate, enter the circulation, and search out and kill the antigenic target. This is generally a powerful, effective, and fast response. For example, the immune system is able to clear out an influenza infection between 7-12 days.

Antigenic targets can only be eliminated if the immune system is competent. Tumors and various other antigenic targets have effectively evolved strategies to successfully evade the host immune system, and various molecular and cellular mechanisms responsible for tumor evasion have been identified. Some of these mechanisms target immune antitumor effector cells. For example, dysfunction and apoptosis of these cells in the tumor-bearing host creates an immune imbalance that cannot be corrected by immunotherapies aimed only at activation of anti-tumor immune responses.

Apoptosis, or Type I cell death, is a type of programmed cell death and can be induced by stress, infection, or DNA damage. Apoptosis is an integral process during development; however, in certain instances it can actually do harm. For example, apoptosis of lymphocyte/hematopoietic populations, including T cells, can be a serious problem during cancer therapy-related chemotherapy and/or radiation therapy. These cells tend to be sensitive to chemotherapy and radiation therapy.

There are two major mechanisms controlling apoptosis in the cell, the p53 pathway (pro-apoptotic) and the nuclear factor kappa B (NF-κB) pathway (anti-apoptotic). Both pathways are frequently deregulated in tumors, as p53 is usually lost, while NF-κB becomes constitutively active.

Tumor-induced apoptosis of lymphocytes is thought to play a significant role in the immune suppression seen in cancer patients. Apoptosis of anti-tumor effector cells has been associated with expression of FasL on the surface of tumor cells. This is based on well-documented evidence that Fas/FasL interactions play an important role in the down-modulation of immune functions, including triggering of activation-induced cell death (AICD), to maintain central and peripheral tolerance. Many human tumors express FasL and can eliminate activated Fas+ effector lymphocytes via the Fas/FasL pathway. FasL expression on tumor cells has been shown to negatively correlate with patient prognosis. In addition, it has been shown that tumors can release membrane-associated FasL through secretion of membranous microvesicles (MVs), thereby providing an explanation for spontaneous apoptosis of T lymphocytes observed in the peripheral circulation of patients with cancer.

Applicants previously showed that MV detected in sera of patients with oral carcinoma induced caspase-3 cleavage, DNA-fragmentation, cytochrome c release, loss of mitochondrial membrane potential (MMP) and TCR ζ-chain down-regulation in activated T lymphocytes. Furthermore, Applicants demonstrated that these tumor-derived MV are distinguishable from immune cell-derived MV by their unique molecular profile and immune-suppressive properties. Recent data also indicate that MVs are present in sera of patients with squamous cell carcinoma of head and neck (H&NSCC) and that these MVs contain biologically active FasL which may be involved in mediating lysis of Fas positive T cells in the peripheral circulation. Thus, the activity of tumor-derived MV might significantly contribute to the dysfunction and death of effector T cells in cancer patients. The loss of these cells could be responsible for inadequate anti-tumor function and, by extension, inadequate immune responses to cancer vaccines.

It has been convincingly demonstrated that H&NSCC is able to induce functional defects and apoptosis in immune effector cells as well as antigen-presenting cells (APCs) by various mechanisms. In previous studies, Applicants have observed a high level of apoptosis of tumor-infiltrating lymphocytes (TIL) and T lymphocytes in the peripheral circulation of H&NSCC and melanoma patients. Applicants demonstrated that CD8+ T cells are more sensitive to apoptosis than CD4+ cells, and that the effector and tumor-specific subpopulations of CD8+ T cells are preferentially targeted for apoptosis. Also, individuals with HIV generally experience immune suppression caused by dramatic reductions in helper T cell populations. This reduction is caused by apoptosis of the HIV-infected helper T cells.

The mechanisms responsible for immune cell dysfunction in patients with cancer are numerous and varied. In addition to a wide variety of soluble immunosuppressive factors such as PGE2, TGF-β, IL-10, and VEGF, and pro-apoptic ligands such as FasL (described above) that are released by tumor cells or other cells in the tumor microenvironment, suppressor cell populations, i.e., regulatory T cells (T regs), have been shown to play a key role in down-regulation of anti-tumor host immunity.

Collectively, these mechanisms create a poisonous environment, which explains the failure of immunotherapy approaches in the past. In order to have an effective therapeutic outcome, these tumor-induced mechanisms of immune suppression must be directly addressed. With the newfound knowledge of the multiple causes of immune dysfunction seen in cancer patients, it is becoming more apparent that multiple active components are needed to create an effective cancer immunotherapy. However, there have been many difficulties in finding an effective immunotherapy and understanding its mechanism of action.

Since toxin-induced tumor regressions of human cancer achieved by William Coley early in the 20$^{th}$ century, cancer therapists have employed hundreds of different immune therapies with only relatively rare clinical responses. Because there was little or no insight into the cause of these failures, no consistent mechanism of action emerged. In order to establish a clear mechanism of action, a therapy needed to be devised which could consistently produce a response that could then be dissected.

Head and neck squamous cell cancer (H&NSCC) offers a good model since much is known about the immune defects seen in these patients. They include, to name a few, (Whiteside, 2001; Hadden, 1995): 1) T lymphocyte anergy and depletion induced by tumor and host-mediated mechanism including prostaglandins, T regs, myeloid suppressor cells, antigen-antibody complexes, and cytokines such as IL-10; 2) monocyte/macrophage functional defects with evidence of suppressor and inflammatory changes (Mantovani, 2002); and 3) dendritic cell (DC) defects characterized by sinus histiocytosis (SH) (Dunn, 2005).

Effective therapeutic efforts were needed to reverse these multiple defects. An extensive review of the literature (Hadden, 1995) and a series of pre-clinical experiments resulted in the primary cell-derived biologic (also known as IRX-2) protocol. The IRX-2 protocol, shown in FIG. 1, employs an initial dose of low dose cyclophosphamide (CY) (300 mg/m$^2$) by intravenous infusion to reverse suppression by T regs and perhaps other forms of suppressors. The CY is followed by 10-20 daily injections of IRX-2 at the base of the skull to feed into the jugular chains of lymph nodes regional to the cancer.

IRX-2 was originally thought to act via increasing T lymphocyte number and function. Recent evidence indicates that reversal of tumor-induced apoptosis is also a major mechanism, as disclosed in U.S. Provisional Patent Application No. 60/990,759 to Signorelli, et al. Indomethacin (INDO) was administered daily for approximately 21 days to block prostaglandin production by tumor and monocyte/macrophages, a known cancer related suppression mechanism. Zinc was also administered as another aspect of the immunorestorative component of the strategy (Hadden, 1995).

Additionally, at the time the protocol was developed, the critical role played by dendritic cells as presenters of tumor antigen to T cells was unknown. It was also unknown that sinus histiocytosis (SH) reflected a DC defect, and specifically a tumor induced failure of maturation and antigen presentation. Mechanism of action studies disclosed in U.S. Pat. Nos. 6,977,072 and 7,153,499 to Applicants made it clear that the IRX-2 protocol reverses this DC defect and produces changes in regional lymph nodes which reflect a potent immunization (Meneses, 2003). More specifically, these patents disclose a method of inducing the production of naïve T cells and restoring T cell immunity by administration of IRX-2, which preferably includes the cytokines IL-1β, IL-2, IL-6, IL-8, INF-γ, and TNF-α. This was one of the first showings that adult humans can generate naïve T cells through molecular therapy. The presence of naïve T cells available for antigen presentation was important in the restoration of immunity.

The mechanistic hypothesis that underpins IRX-2 is similar to that of a therapeutic cancer vaccine, although no exogenous antigen is required. When administered into the neck, the agent is thought to act in the cervical lymph node chain directly on DCs to promote their maturation and subsequent ability to present endogenous tumor antigen to naïve T cells.

Non-clinical data regarding the mechanism of action of IRX-2 has shown that the agent effectively stimulates and activates human monocyte-derived DCs (Egan, 2007). IRX-2 treatment of immature DCs increased expression of CD83 and CCR7 (markers for maturation and lymph node migration, respectively), as well as differentiation molecules that are important for antigen presentation to naïve T cells. Additionally, IRX-2 induces CD40, CD54, and CD86, which are co-stimulatory receptors that are critical for activation of naïve T cells. Functional changes in IRX-2-treated DCs included an increase in antigen presentation and T cell activity. Taken collectively, IRX-2 treatment of immature DC drives morphologic, phenotypic, and functional changes that are consistent with the development of mature and activated DCs that are able to effectively stimulate naïve T cells.

In contrast to defined antigen-based therapeutic cancer vaccines where antigen-specific reactivity can be measured, rejection antigens have not been discovered in H&NSCC, thus limiting the ability to measure antigen-specific reactivity after IRX-2 therapy.

While IRX-2 was shown to increase T lymphocyte function and generate new immature T cells, there was no disclosure or suggestion and thus no conclusive demonstration that IRX-2 prevented apoptosis of those T cells once generated and it was not known what the function of the T cells were after presentation of antigen. There were no experimental results that showed that apoptosis of T cells was prevented or would even suggest the mechanism of action. Proliferation and apoptosis are separate cellular processes and it would be imprudent to assume that a factor that causes proliferation would necessarily protect from programmed cell death. The exact mechanism by which IRX-2 restores the antitumor response of T cells, and prevents their apoptosis, was neither expressly nor inherently disclosed in the prior art. Furthermore, while IRX-2 was shown to be effective in the mechanisms described above during cancer treatment, there has been no evidence that IRX-2 provides the same mechanism of action in other instances of immune suppression besides cancer.

Not only have individual cytokines not been able to completely restore each part of the immune system through the promotion of DC maturation, the generation of new T cells, and prevention of their apoptosis; but other therapeutics including multiple cytokines have not been able to do this as well. For example, MULTIKINE® (Cel-Sci) is effective only on the tumor itself, affecting the cell cycle of the tumor cells. PROVENCE® (sipuleucel-T, Dendreon), GVAX® (Cell Genesys), PROMUNE® (Coley Pharmaceutical Group), Dynavax TLR 9 ISS, ONCOPHAGE® (vitespen, Antigenics), CANVAXIN® (CancerVax), and TROVAX® (Oxford BioMedica) have been able to show antigen amplification, dendritic cell processing, and some cellular adjuvancy. TREMELIMUMAB® (Pfizer) and IPILIMUMAB® (Medarex and Bristol-Myers Squibb) only target the T regulatory cell population.

In addition, some therapeutic agents have addressed the issue of apoptosis of cells. There are several biological agents and small molecules that have been developed to prevent cellular and lymphocyte apoptosis. For example, International Patent Application Publication WO/2006/039545 to Maxim Pharmaceuticals, Inc. discloses the administration of a PARP-1 inhibitor and additionally an inhibitor of reactive oxygen metabolite (ROM) production or release to protect tumorcidal lymphocytes, including cytotoxic T lymphocytes and NK cells, from apoptosis. A cytotoxic lymphocyte stimulatory composition including various cytokines can be co-administered. This application reports that free radicals produced by tumor adjacent phagocytes cause dysfunction and apoptosis in tumorcidal or cytotoxic lymphocytes.

International Patent Application Publication WO/2005/056041 to Cleveland Clinic Foundation discloses latent TGF-β as a compound that can be used to protect a patient from treatments that induce apoptosis. The latent TGF-β induces NF-κB activity, thus preventing apoptosis.

International Patent Application Publication WO/2007/060524 to Fundacion de la Comunidad Valenciana discloses various ringed compounds that are inhibitors of Apaf-1 and therefore act as apoptosis inhibitors. Apaf-1 is an apoptotic protease-activating factor that makes up part of an apoptosome. Capsase-9 is activated within the apoptosome and initiates apoptotic signals.

Amifostine (ETHYOL, MedImmune) is another compound that is administered in order to reduce toxicities resulting from chemotherapy and radiotherapy. More specifically, it is an intravenous organic thiophosphate cytoprotective agent.

There are several disadvantages to these present treatments. For biological agents, there is the problem of difficulty in manufacturing and possible difficulty in specifically targeting a given cell population. For small molecules, there may be a problem of toxicity if used systemically. Further, agents with a single mechanism of action have shown a lack of efficacy because multiple activities are needed to promote anti-apoptotic effects in lymphocyte cell populations. Also, none of these treatments directly address the immunosuppressive environment created by the tumor. Thus, effective adjuvants and approaches to neutralize the tumor-induced suppression are lacking in the prior art.

In essence, the earlier work of Applicants described the mechanism of action of the primary cell derived biologic with respect to DC maturation and generation of naïve T cells, i.e. several specific levels of affecting the immune system. Presented herein is evidence of another level of effect, of the primary cell derived biologic, namely promotion of the survival of lymphocytes. The data herein, taken together with prior disclosures by the Applicants, show that the primary cell derived biologic has a corrective and positive effect on the generation and activation of specific effectors, and their subsequent survival—each level of the immune system, i.e. each arm of the immune system. Compositions of the prior art are directed to only one of these levels.

Therefore, there is a need for a composition that can effectively enhance both effector generation and effector survival and target each arm of the immune system to restore the immune system and provide a complete mechanism of action against immune suppression.

BRIEF SUMMARY OF THE INVENTION

The present invention provides for a method of increasing immunological effect, including the steps of administering an effective amount of a primary cell derived biologic to a patient, inducing immune production, blocking immune destruction, and increasing immunological effect in the patient.

The present invention provides for a method of treating an immune target in a patient, including the steps of administering an effective amount of the primary cell derived biologic to the patient, inducing immune production, blocking immune destruction, and treating the immune target in the patient.

The present invention also provides for a method of treating a tumor in a patient, including the steps of administering an effective amount of the primary cell derived biologic to the patient, inducing immune production, blocking immune destruction, and treating the tumor in the patient.

The present invention further provides for a method of immune prophylaxis, including the steps of administering an effective amount of a primary cell derived biologic to a patient, inducing immune production, blocking immune destruction, and preventing immune suppression in the patient.

The present invention also provides for a method of preventing tumor escape in a patient, including the steps of administering an effective amount of a primary cell derived biologic to the patient, inducing immune production, blocking immune destruction, and preventing tumor escape in the patient.

BRIEF DESCRIPTION OF THE SEVERAL VIEWS OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

In general, the present invention is directed to the application of the mechanism of action of IRX-2 both with respect to tumors and the immune system in general and provides for a method of treating an immune target by the administration of a primary cell derived biologic. The primary cell derived biologic produces an immune rejection of the immune target, as further described below by reversing immune incompetence and potentiating immune response.

Figure 3:
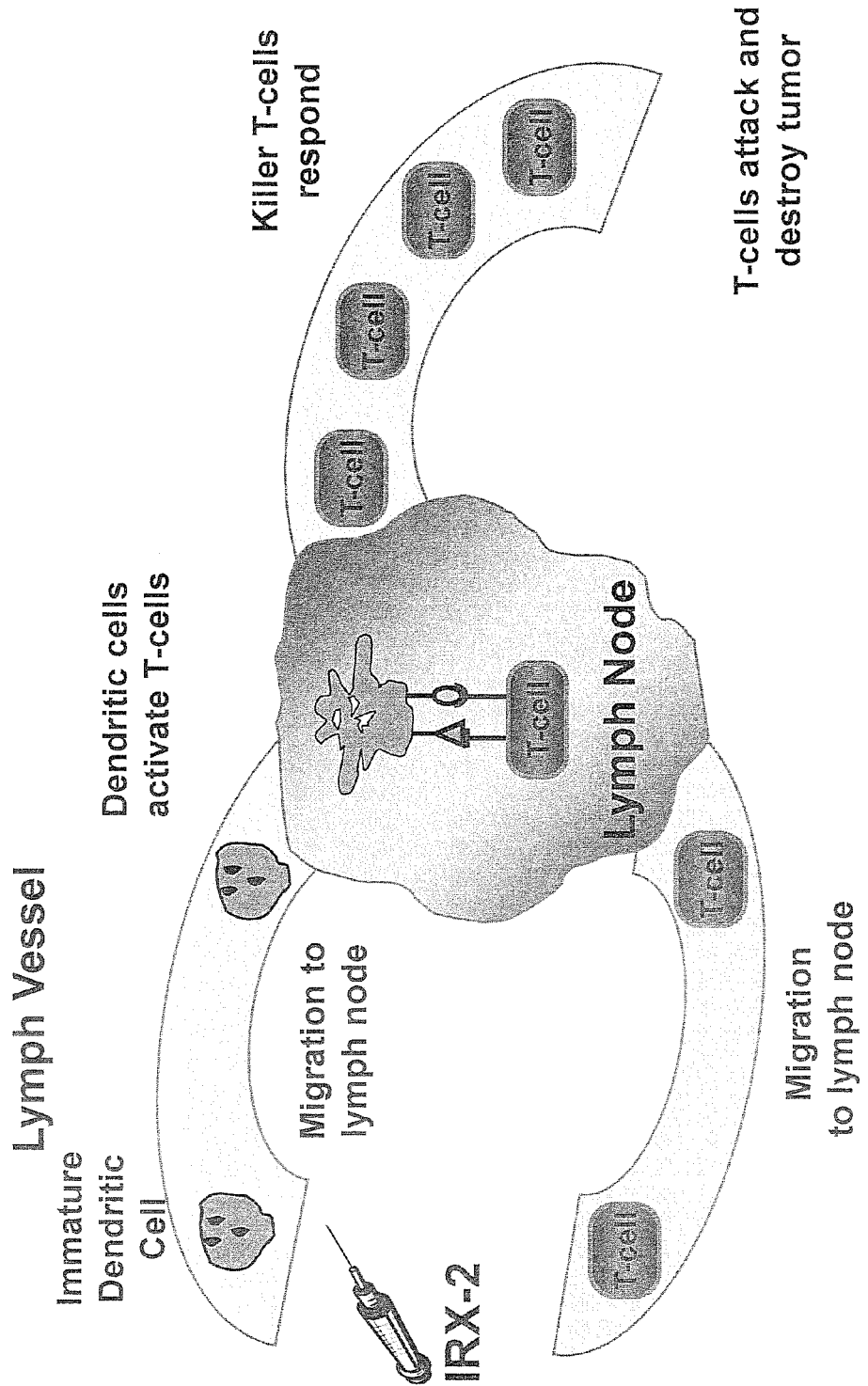
FIG. 3 is a representation of the mechanism of action of IRX-2.

More specifically, the primary cell biologic of the present invention affects each arm of the immune system (cellular and humoral) and by doing so the primary cell derived biologic is able to effectively potentiate the immune system. The primary cell derived biologic both induces immune production and blocks immune destruction, so that there is a net positive immune effect. In other words, not only are the effects of immune destruction reversed, but also immune production is increased notwithstanding that reversal. Thus, the immune system is potentiated to an even greater degree than if there was increased humoral and/or cellular response or only decreased inhibition of immune destruction. All aspects of the immune system are affected upon administration of the primary cell derived biologic, as shown in FIG. 3, including dendritic cell maturation, naïve T cell production, effective antigen presentation, prevention of apoptosis, and tumor infiltration by lymphocytes. That the primary cell derived biologic has an effect on all aspects of the immune system makes it different and more effective than previous therapies, which only address one aspect of the immune system.

The primary cell derived biologic is not a "vaccine" in the classic sense of the word, although it can certainly function in the manner of a vaccine. A classic vaccine is used to "turn on" a competent immune system and have traditionally been effective only in a prophylactic setting. The primary cell derived biologic, however, reverses an incompetent immune system, i.e. one in which an immune target or other therapy (eg radiation, chemotherapy) has rendered incompetent, and reverse this incompetence. In other words, the primary cell derived biologic is able to make an immune incompetent patient immune competent. This is a critical step in treating immune targets such as cancer and chronic viral infections.

DEFINITIONS

As used herein, the term "immune target" refers to any antigenic source or entity that can be rendered antigenic and afflicts the host patient. Generally, such targets, such as immunogenic pathogens and tumors, show surface antigen that would otherwise induce an immune response in an immune competent patient. In addition, exogenous antigen can cause an otherwise non-immunogenic immune target to be susceptible to immune attack in an immune competent patient. With specific regard to the present invention, the immune target is immunogenic or potentially immunogenic to which the immune system is nonresponsive due to immune incompetence from any cause. In the present invention, the immune target is "targeted" by the immune system made competent by the primary cell derived biologic which reverses the immune suppression and restores the immune system to function.

The immune incompetence can be caused by genetic defects in the components of the immune system (intrinsic, or primary immune deficiencies). The immune suppression can also be caused by extrinsic factors (secondary immune deficiencies). For example, diseases such as AIDS or HIV, irradiation (radiotherapy), chemotherapy, malnutrition, burns, infections, and cancer (tumors) can cause immune suppression.

As used herein, "apoptosis" refers to cell death. As stated above, apoptosis (Type I cell-death) is a type of programmed cell death that occurs for various reasons such as stress, infection, or DNA damage. Apoptosis of lymphocytes can be induced by a variety of phenomena, such as, but not limited to cancer-related therapies (chemotherapy, radiation), and tumors themselves producing apoptosis-inducing factors.

As used herein, "effective amount" refers to an amount of primary cell derived biologic that is needed to achieve the desired result of the present invention, namely, protecting lymphocytes and other hematopoietic components from apoptosis as well as activating the immune system to attack an immune target. One skilled in the art can determine the effective amount of the primary cell derived biologic that should be given to a particular patient.

As used herein, "increasing immunological effect" refers to the process of changing an incompetent immune system to a competent immune system. The function of a single component of the immune system is reversed from incompetent to competent, and preferably, the function of multiple components is reversed from incompetent to competent. Therefore, the effect that the immune system has on an immune target is increased. A competent immune system is required to effectively destroy tumors and other immune targets. Not merely turning on but preventing breakdown so that there is a build up of immunity.

As used herein, "lymphocytes" refers to a white blood cell present in the immune system and includes large granular lymphocytes (natural killer (NK) cells) and small lymphocytes (T cells and B cells).

A "primary cell derived biologic", as used herein, is a combination of cytokines, preferably natural and non-recombinant cytokines, also previously known as a natural cytokine mixture (NCM). Preferably, the primary cell derived biologic is IRX-2 (citoplurikin) as described below, and the two terms can be used interchangeably throughout this application without deviation from the intended meaning.

"IRX-2", also known as "citoplurikin", is a leukocyte-derived, natural primary cell derived biologic produced by purified human white blood cells (mononuclear cells) stimulated by phytohemagglutinin (PHA) and ciprofloxacin (CIPRO). The major active components are interleukin 1β (IL-1β), interleukin 2 (IL-2), interleukin 6 (IL-6), interleukin 8 (IL-8), tumor necrosis factor α (TNF-α), and γ-interferon (IFN-γ). Preferably, the IRX-2 used in the present invention includes these six critical cytokines. IRX-2 has also previously been referred to as an "NCM", a natural cytokine mixture, defined and set forth in U.S. Pat. Nos. 6,977,072 and 7,153,499.

Briefly, IRX-2 is prepared in the continuous presence of a 4-aminoquinolone antibiotic and with the continuous or pulsed presence of a mitogen, which in the preferred embodiment is PHA. Other mitogens, however, can also be used. The IRX-2 produced for administration to patients contains a concentration of IL-1β that ranges from 60-6,000 pcg/mL, more preferably, from 150-1,800 pcg/mL; a concentration of IL-2 that ranges from 600-60,000 pcg/mL, more preferably, from 3,000-12,000 pcg/mL, and concentrations of IFN-γ and TNF-α that range from 200-20,000 pcg/mL, more preferably, from 1,000-4,000 pcg/mL.

IRX-2 can also contain a concentration of IL-6 that ranges from 60-6,000 pcg/mL, more preferably, from 300-2,000 pcg/mL; a concentration of IL-8 that ranges from 6000-600,000 pcg/mL, more preferably from 20,000-180,000 pcg/mL; a concentration of TNF-α that ranges from 200-20,000 pcg/ml, more preferably, from 1,000-4,000 pcg/mL. Recombinant, natural or pegylated cytokines can be used, or IRX-2 can include a mixture of recombinant, natural or pegylated cytokines. The IRX-2 of the present invention can further include other recombinant, natural or pegylated cytokines such as IL-7, IL-12, IL-15, GM-CSF (at a concentration that ranges from 100-10,000 pcg/mL, more preferably from 500-2,000 pcg/mL), and G-CSF. The method of making IRX-2 is disclosed in the above cited patents as well as in U.S. Provisional Patent Application No. 61/044,674.

Figure 2:
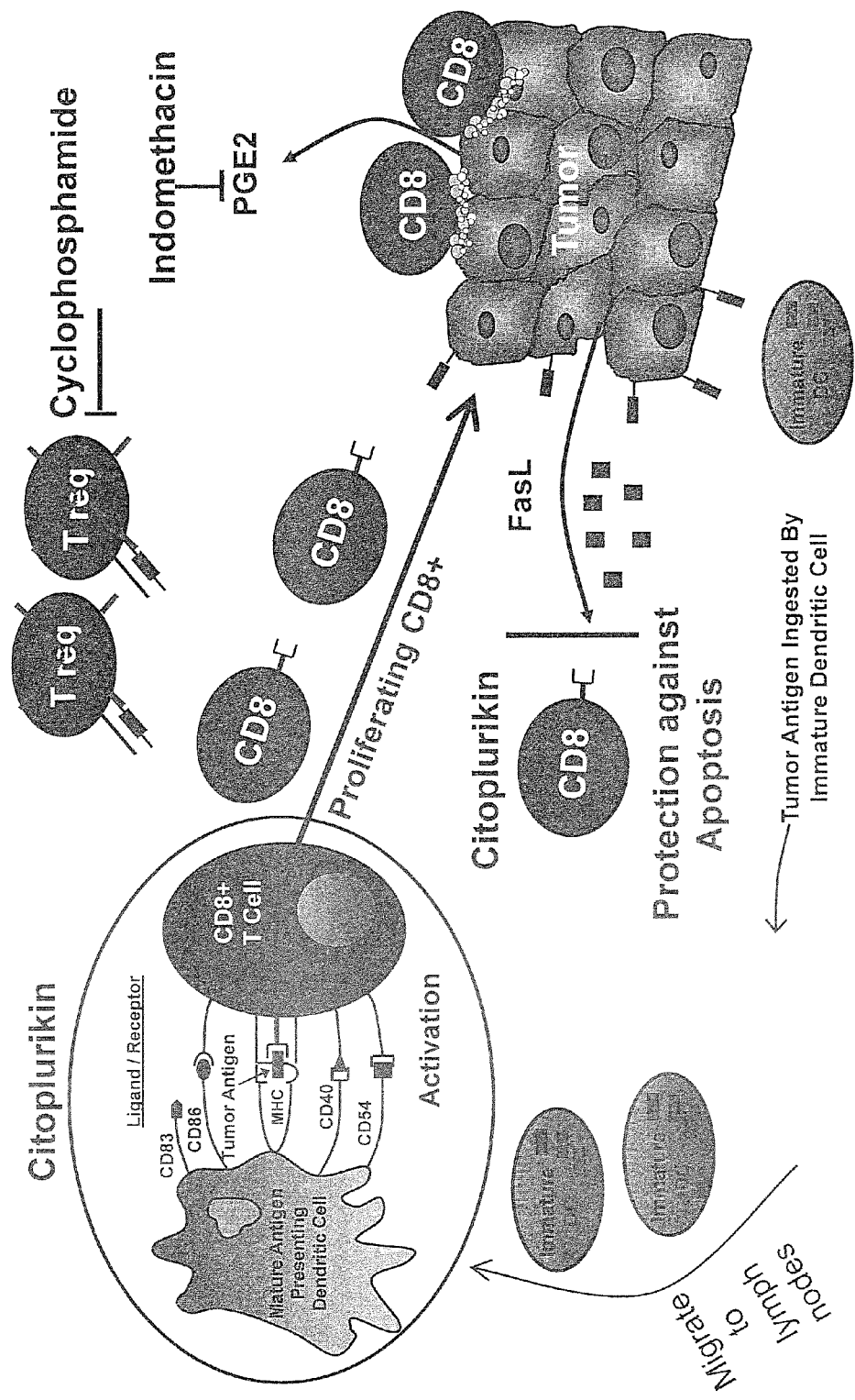
FIG. 2 is a representation of the mechanism of action of IRX-2 in combination with a chemical inhibitor and NSAID.

Other compounds can also be administered along with IRX-2, such as chemical inhibitors, non-steroidal anti-inflammatory drugs (NSAIDS), zinc, and combinations thereof. The chemical inhibitor can be any chemotherapeutic agent (preferably used at low doses) that has immunomodulatory effects so as to increase immunity and/or an immune response, e.g., by preferentially inhibiting immune suppression or suppressor mechanisms in the body. According to a preferred embodiment, the chemical inhibitor is an anti-neoplastic agent, including but not limited to alkylating agents, antimetabolites and antibiotics. The chemical inhibitor can also be an immunomodulating agent such as thalidomide. The chemical inhibitor can also be in a salt or other complex form. Preferably, the chemical inhibitor is the alkylating agent cyclophosphamide (CY). The NSAID is preferably indomethacin (INDO), which is both a Cox I and Cox II inhibitor. The NSAID can also be ibuprofen or Cox II inhibitors such as celecoxib and rofecoxib, or combinations thereof. The four components used together (i.e. chemical inhibitor, NSAID, primary cell derived biologic, and zinc) are able to address the suppressive environment created by the immune target and restore the cellular immune response of the patient. More specifically, the chemical inhibitor inhibits T regulatory cells; the NSAID reverses local immune suppression by prostaglandins, the primary cell derived biologic activates dendritic cells, stimulates T cells, and protects T cells from apoptosis; and zinc provides key nutrients for T cell function as shown in FIG. 2. This combined action encourages immune response to both endogenous and exogenous antigens.

"Tumor escape" as used herein refers to any mechanism by which tumors escape the host's immune system.

The Overall Mechanism of the Primary Cell Derived Biologic

The present invention is directed to a method of increasing immunological effect, including the steps of administering an effective amount of a primary cell derived biologic, inducing immune production, blocking immune destruction, and increasing immunological effect.

Immune Production

Immune production is induced by maturing immature dendritic cells, the resulting mature dendritic cells activating naïve T cells, modifying populations of B and T cells in blood, activating regional lymph nodes, infiltrating an area adjacent to an immune target with T helper and B cells, and infiltrating the immune target with T killer cells and macrophages.

The primary cell derived biologic causes maturation of dendritic cells and induces the production of naïve T cells, as described in U.S. Pat. Nos. 6,977,072 and 7,153,499. The mature dendritic cells can then present antigen to the naïve and memory T cells and activate them.

The populations of B and T cells can be up-regulated or down-regulated, i.e. modified, due to IRX-2 administration. The populations of B and T cells in the blood that are modified are more specifically populations of naïve T cells and early memory T cells. The populations of naïve T cells that are modified are CD3+ CD45RA+ CCR7+. This is accomplished by differentiating naïve T cells into memory and effector T cells, which is a time dependent process. The central memory T cells are also caused to exit the bloodstream and migrate to draining lymph nodes. In other words, the modification of levels of naïve T cells is the result of the naïve T cells differentiating into more advanced forms of T cells that can effectively attack the immune target. The populations of B cells in the blood are also modified because the B cells are recruited into lymph nodes, exposed to antigen, migrate to the immune target, and attack the immune target. More specifically, the B cells attack the immune target by producing antibodies and/or supporting antibody-dependent cellular cytotoxicity.

The regional lymph nodes are activated as evidenced by their enlargement, replenishment of lymphocytes, and reversing sinus histiocytosis. Immunization to antigen to the immune target occurs in the regional lymph nodes.

Infiltration of the area adjacent to the immune target is mainly by CD45RA+, CD3+, and CD4+ T lymphocytes and CD20+ B lymphocytes. The area adjacent to the immune target can range from the surface of the immune target itself to a distance from the surface. Infiltration of the immune target itself, i.e. directly within the immune target, occurs with CD45RO+, CD3+, and CD8+ lymphocytes (i.e. killer T cells) and CD68+ macrophages. Each of these infiltration processes contribute to producing humoral (mediated by antibodies) as well as cellular (mediated by cells) immunity.

Blocking Immune Destruction

Immune destruction is blocked by protecting the activated T cells from apoptosis. One of the mechanisms of tumor escape involves targeted elimination of CD8+ effector T cells through apoptosis mediated by tumor-derived microvesicles (MV). Immunosuppressive MV have been found in neoplastic lesions, sera, ascites and pleural effusions obtained from cancer patients and have been linked to apoptosis and TCR alterations in effector T cells in these patients. MV-driven elimination of effector T cells, which are necessary for anti-tumor host defense, contributes to tumor escape and cancer progression. Therefore, protection of anti-tumor effector cells from functional impairments and death is a major objective of immune therapy. Clinical and experimental data show that certain cytokines, especially survival cytokines using the common receptor γ chain, are able to protect activated T cells from tumor-induced death and enhance their anti-tumor activity.

More specifically, there are several ways in which IRX-2 protects T cells from apoptosis. The expression of anti-apoptotic signaling molecules (i.e. JAK-3 and phosphor-Akt) is up-regulated and the expression of pro-apoptotic molecules (i.e. SOCS-2) is down-regulated. Activation of caspases in CD8+ and CD4+ T lymphocytes is decreased and cFLIP expression is increased. Inhibition of the PI3K/Akt survival pathway is counteracted by IRX-2. The T cells are protected from both extrinsic apoptosis (MV-induced and FasL-induced apoptosis) and intrinsic metabolic (cellular stress or DNA damage related) apoptosis.

The protection from extrinsic MV-induced apoptosis is further accomplished by preventing down-regulation of JAK3, CD3-ζ, and STAT5; inhibiting dephosphorylation of Akt-1/2; and maintaining balanced ratios of Bax/Bcl-2, Bax-Bcl-xL, and Bim/Mcl-1. The protection from MV-induced apoptosis is also accomplished by preventing induction of the activity of caspase-3 and caspase-7. More specifically, the induction of the active cleaved form of caspase-3 is blocked, as is the loss of mitochondrial membrane potential. Nuclear DNA fragmentation is inhibited. Protection from intrinsic apoptosis by IRX-2 is shown by its protection of activated T cells from staurosporine-induced apoptosis.

Importantly, the cytokines of IRX-2 protect the activated T cells from apoptosis in a synergistic manner. In other words, the combination of the cytokines in IRX-2 produces a greater affect than is seen by administering individual cytokines alone.

The primary cell derived biologic, i.e. IRX-2, administered is preferably as described above. A chemical inhibitor, low dose cyclophosphamide is preferably administered prior to administering the IRX-2, which reverses suppression by T regs lymphocytes. An NSAID (preferably indomethacin) and zinc can also be administered daily during the IRX-2 regimen. Dosing of IRX-2 is further described below.

Inducing immune production and blocking immune destruction is essentially restoring and potentiating the cellular and humoral arms of a patient's immune system that were previously incompetent. This is accomplished by restoring naïve T cell populations, activating T and B cells, promoting infiltration of leukocytes into and adjacent to an immune target, and extending the duration of immune response as described above. These steps of inducing immune production and blocking immune destruction together produce evidence of increased immunological effect because each arm of the immune system has been changed from incompetent to competent, and thus immune targets can be effectively attacked and destroyed.

Patients who have a suppressed immune system or immune incompetence benefit from IRX-2 treatment and have their immune system restored to normal or higher levels of function, i.e. they have a reversal of immune incompetence and an increased immunological effect. For example, tumors and other immune targets tend to down-regulate various immune components needed to attack that immune target. Immune targets have defenses which prevent effective attack by the immune system. Furthermore, the dendritic cells of the immune suppressed patients can induce T and B cells to become tolerant of the presence of the immune target. These immune targets are susceptible to attack, however, once the immune system has been unsuppressed and changed from incompetent to competent. IRX-2 breaks the tolerance by inducing maturation of the dendritic cells to the immune target, encourages the generation of naïve T cells to be activated by mature dendritic cells, overcomes suppression, and prevents T cell apoptosis. In this manner, IRX-2 activates each of the arms of the immune system as described above in order to overcome all of the protective effects of the immune target.

Other Embodiments

Various other procedures can be performed in combination with the IRX-2 administration in each of the methods of the present invention to further enhance therapy such as, but not limited to, surgery, radiotherapy, chemotherapy, or combinations thereof. For example, IRX-2 administration before radiotherapy or chemotherapy (cytodestructive processes) improves the results of these processes because IRX-2 acts as a cytoprotectant by protecting T lymphocytes from apoptosis.

The present invention also provides for a method of treating an immune target, including the steps of administering an effective amount of a primary cell derived biologic, inducing immune production and blocking immune destruction as described above, and treating the immune target. These steps produce evidence of immune rejection of the immune target. In other words, inducing immune protection and blocking immune destruction is evidence that the immune system has recognized that the immune target must be destroyed as well as evidence that the immune system has been restored to function normally (or at a higher level than previously in a disease or immune suppressed state).

The present invention provides for a method of treating a tumor including the steps of administering an effective amount of a primary cell derived biologic, inducing immune production and blocking immune destruction as described above, and treating the tumor. More specifically, the method of treating a tumor is accomplished by modifying populations of B and T cells in blood, activating regional lymph nodes, peritumorally infiltrating the tumor with T helper and B cells, intratumorally infiltrating the tumor with killer T cells and macrophages, and treating the tumor. Killer T cells are produced by maturing immature dendritic cells, activating naïve T cells, the resulting mature dendritic cells stimulating the naïve T cells, and differentiating the naïve T cells into killer T cells. As evidenced herein, the naïve T cells can now differentiate into killer T cells and become directed to a tumor so that the tumor can be treated and destroyed. Each of these steps is as described above. IRX-2 is shown below in the Examples to treat tumors in various stages of cancer as evidenced by softening of the tumor, reducing pain caused by the tumor, reducing the size of the tumor, fragmentation of the tumor, necrosis of the tumor, and fibrosis of the tumor. In essence, IRX-2 unsuppresses and potentiates the cellular and humoral arms of immunity so that a tumor can effectively be treated and cancer eradicated, i.e. completely eliminated, from a patient.

The present invention provides a method of immune prophylaxis, including the steps of administering an effective amount of the primary cell derived biologic, inducing immune production and blocking immune destruction as described above, and preventing immune suppression. Immune prophylaxis is the prevention of the immune system from being suppressed. The primary cell derived biologic actively turns on all parts of the immune system, specifically by maturing immature dendritic cells, activating naïve T cells, the resulting mature dendritic cells activating the naïve T cells, protecting the activated naïve T cells from apoptosis (especially when administered before performing chemotherapy or irradiation), differentiating the naïve T cells into memory and effector T cells, and activating regional lymph nodes so that the immune system does not become suppressed. Each of these steps is as described above. If a patient is prone to immune suppression due to biological factors, this patient can be given IRX-2 preemptively to prevent their immune system from becoming depressed. For example, if a patient has certain genetic factors that predispose them to developing cancer, IRX-2 can be administered so that in the event that an immune target such as cancer does become present, the immune system will be ready to attack the immune target.

The present invention further provides for a method of preventing tumor escape, including the steps of, administering an effective amount of a primary cell derived biologic, inducing immune production and blocking immune destruction as described above, and preventing tumor escape. More specifically, tumor escape is prevented by producing an immune regression of a tumor by modifying populations of B and T cells in blood, activating regional lymph nodes, peritumorally infiltrating the tumor with T helper and B cells, intratumorally infiltrating the tumor with T killer cells and macrophages. Each of these steps is as described above. Many tumors resist immune response by expressing immunosuppressive signals. Since the immune system is completely unsuppressed by IRX-2, tumor escape and subsequent metastasis are prevented. Importantly, the patients in the Examples below experienced a reduction or delay in recurrence of tumors after IRX-2 treatment, illustrating that IRX-2 can prevent tumor escape.

The present invention provides for a method of protecting activated T cells from apoptosis, including the steps of administering an effective amount of a primary cell derived biologic (IRX-2), and protecting activated T cells from apoptosis. Essentially, the method of protecting activated T cells from apoptosis enhances their anti-tumor activity, because the T cells live longer to perform their necessary functions.

The present invention also provides for a method of enhancing the anti-tumor activity of T cells, including the steps of administering an effective amount of a primary cell derived biologic, stimulating the production of naïve T cells, activating the naïve T cells, protecting the activated T cells from apoptosis, and enhancing the anti-tumor activity of the T cells. Naïve T cells are produced in response to the administration of IRX-2, as disclosed in U.S. Pat. Nos. 6,977,072 and 7,153,499. These naïve T cells become activated and mature through the presentation of tumor antigen. According to the present invention, the IRX-2 can now protect these activated T cells from apoptosis. This protection is accomplished as described above.

The present invention is useful in preventing apoptosis in cancer patients suffering from cancers such as, but not limited to, squamous cell head and neck cancer (H&NSCC), lung, renal-cell, breast, and colorectal cancers. Furthermore, the present invention can be used to prevent and/or reverse immune suppression in HIV patients by preventing apoptosis of helper T cells.

The present invention also provides for a method of prolonging the life of lymphocytes, including the steps of administering an effective amount of a primary cell derived biologic (IRX-2), and prolonging the life of lymphocytes. The lymphocytes that are affected by IRX-2 are preferably T cells. IRX-2 can further prolong the life of other cells that could be affected by apoptosis, such as B cells and hematopoietic populations, (dendritic cells, monocytes and myeloid cells). IRX-2 prevents the T cells from otherwise dying, thus prolonging their lives and allowing them to acquire and exert the anti-tumor effects for which they are programmed, e.g. cytolytic activity or T helper activity. In other words, the IRX-2 prevents apoptosis of the T cells, thus prolonging the lives of the T cells.

The present invention further provides for a method of cytoprotective cancer therapy, including the steps of, administering an effective amount of a primary cell derived biologic (IRX-2), producing a cytoprotective effect on T cells, and performing a cancer therapy such as, but not limited to radiation, chemotherapy, and combinations thereof. Normally, cancer therapies such as radiation and chemotherapy suppress immunity by inducing apoptosis in T cells, i.e. they are cytodestructive. The present invention counteracts the cytodestructive effects, preserving immune function and/or accelerating its recovery after treatment.

There are several advantages of the present invention with regard to apoptosis. First, the primary cell derived biologic used in the present invention is a well-defined biologic that is manufactured in a robust and consistent manner (IRX-2). This is unlike the previously disclosed prior art compounds that are able to protect T cells from apoptosis, but are not manufactured robustly. Further, the cytokines in the primary cell derived biologic used in the present invention act synergistically on multiple cell types of the immune system resulting in a coordinated immune response at doses far lower than are needed to achieve similar results using single, recombinant cytokines as monotherapies, as evidenced in the examples below.

As shown in the following examples, it was determined that IRX-2 is able to protect T cells from apoptosis mediated by tumor-derived MV. Some of the cytokines present in the IRX-2 such as IL-2 are known to have anti-apoptotic effects; thus, it was reasonable to evaluate whether the IRX-2 had protective as well as stimulatory effects on T cells. The combined effects of T cell survival enhancement and functional stimulation underlie IRX-2's apparent synergistic effects in vivo. Using a previously established in vitro model of tumor-induced apoptosis, it is demonstrated herein that IRX-2 provides strong protection to T cells from apoptosis mediated by tumor-derived MV through activation of survival pathways, thereby effectively counteracting cancer-related immunosuppression. The results of these experiments are presented in the examples below. Thus, it is shown herein that IRX-2 is effective against a new arm of the immune system and is able to restore that arm of the immune system, i.e. preventing apoptosis of lymphocytes.

Tumor-derived microvesicles (MV) expressing a membrane form of FasL were purified from supernatants of the PCI-13 tumor cell line and co-incubated with CD8+ Jurkat cells or activated peripheral blood (PB) T cells. FasL, the Fas ligand, is a type II transmembrane protein belonging to the tumor necrosis factor (TNF) family. FasL-receptor interactions play an important role in the regulation of the immune system and the progression of cancer. Apoptosis is induced upon binding and trimerization of FasL with its receptor (FasR), which spans the membrane of a cell targeted for death.

Incubation of CD8+ Jurkat T cells and activated PB T cells with tumor-derived MV induced significant apoptosis, as evidenced by increased annexin binding (64.4%±6.4), caspase activation (58.1%±7.6), a loss of mitochondrial membrane potential (MMP) (82.9%±3.9) and DNA-fragmentation.

Pre-incubation of T cells with IRX-2 suppressed apoptosis in a dose- and time-dependent manner ($p<0.001$ to $p<0.005$). The observed protective effects on $CD8^+$ T cells of IRX-2 were comparable to the cytoprotective effects of recombinant IL-2 or IL-15 alone but was superior to IL-7; however, IRX-2 had greater effects on protecting $CD4^+$ T cells from apoptosis IRX-2 does not contain IL-7 or IL-15 and the fact that it is protecting $CD4^+$ T cells from apoptosis more effectively than equivalent amounts of recombinant IL-2 means that the unique components of IRX-2 act synergistically to protect T cells from apoptosis.

IRX-2 suppressed MV-induced down-regulation of JAK3 and the TCR-associated ζ-chain and induced strong Stat5 activation in T cells. Flow cytometry analysis showed that IRX-2 reversed the MV-induced imbalance of pro- and anti-apoptotic proteins in T cells by suppressing the MV-mediated up-regulation of pro-apoptotic proteins Bax and Bim ($p<0.005$ to $p<0.05$), and concurrently restoring the expression of the anti-apoptotic proteins Bcl-2, Bcl-xL, FLIP and Mcl-1 ($p<0.005$ to $p<0.01$). In addition, IRX-2 treatment counteracted the MV-induced inhibition of the PI3K/Akt survival pathway. A specific Akt-inhibitor (Akti-1/2) abrogated the protective effect of IRX-2, demonstrating that the PI3K/Akt pathway plays a key role in IRX-2-mediated survival signaling. The PI3K/Akt pathway is a key component in preventing apoptosis and activation of this pathway would prevent against many different inducers of apoptosis. These studies show that a short ex vivo pre-treatment with IRX-2 provides potent protection of T cells from tumor-induced apoptosis. As effector T cells resistant to immunosuppressive influences of the tumor microenvironment are essential for anti-tumor host defense, utilization of IRX-2 significantly improves the effectiveness of cancer biotherapies.

The present invention also provides for a method of inducing immunization in a patient, including the steps of administering an effective amount of the primary cell derived biologic, detecting a change in T and B cells, and inducing immunization in a patient. The changes in circulating T and B cell subset compositions, described above, reflect alterations in lymphocyte generation, differentiation, and traffic. i.e. a modification in levels of T cells and B cells in blood occurs because they are differentiating or moving to other areas. These changes in subset composition are evidence that immunization has been induced in a patient.

The present invention also provides a method of predicting a favorable treatment outcome to cancer treatment, including the steps of administering an effective amount of the primary cell derived biologic, detecting an increase peritumorally of T helper and B cells and intratumorally of T killer cells and macrophages, and predicting a favorable treatment outcome to cancer treatment. More specifically, an increase is detected peritumorally of CD45RA+ CD3+ CD4+ T lymphocytes and CD20+ B lymphocytes and intratumorally of CD45RO+ CD3+ CD8+ lymphocytes and CD68+ macrophages as described above. In other words, this characteristic change in leukocyte infiltration is a biomarker that indicates that treatment with the primary cell derived biologic will be effective. This biomarker can be used to screen out patients for whom continued treatment with the primary cell derived biologic will not be successful so that these patients can seek other alternatives. This method can use automated means for predicting the treatment outcome, such as, but not limited to, various assays or immunoassays (ELISA, radioimmunoassays) and high-throughput methods such as flow or microscopic cytometry.

Advantages of the Primary Cell Derived Biologic

Overall, IRX-2 unsuppresses and potentiates all aspects of the cellular and humoral arms of the immune system to attack various immune targets. Any immune incompetent disease state (cancer, AIDS, and others as previously described above) can now be reversed by unsuppressing and potentiating the immune system through IRX-2. IRX-2 functions as a "symphony" rather than just a single "instrument" in that the specific combination of cytokines of IRX-2 effect multiple parts of the immune system, as opposed to prior art therapeutics which, while being combinations of components, either augment generation of effectors or prevent their apoptosis, i.e. only work on a single part of the immune system. Each part of the immune system is a gatekeeper of one effect experienced by IRX-2 administration. Each of these parts of the immune system is required in order to attack an immune target. FIGS. 2 and 3 depict the processes potentiated by IRX-2 therapy. Immature dendritic cells must become mature in order to activate naïve T cells. Production of naïve T cells also must be induced so that they can be presented with antigen by the mature dendritic cells. Both the naïve T cells and the dendritic cells must migrate to the regional lymph node in order for antigen to be presented to the naïve T cells by the dendritic cells. Once activated, the T cells must be protected from apoptosis so that they can differentiate into killer T cells and attack the immune target. B cells also mature into plasma cells to aid in attacking the immune target. Administration of IRX-2 augments all of these processes, providing a competent immune system that is ready to attack any immune target.

Dosing and Administration

Administration of the primary cell derived biologic in vivo is the same as the vaccine+IRX-2 or IRX-2 alone immunotherapy disclosed in the previously mentioned patents related to IRX-2. IRX-2 is preferably injected perilymphatically over a 10 day regimen at 115 Units per injection, but can also be injected with other methods further described below. Alternatively, other regimes can be used wherein the IRX-2 is administered intermittently. For example, it can be administered three days a week or five out of seven days a week. As shown below, IRX-2 inhibits apoptosis over a range of concentrations: from 1:1 to 1:10 dilution of the IRX-2 liquid (i.e. dilution of the IRX-2 in the media in which it was produced).

Preferably, the IRX-2 is injected around lymphatics that drain into lymph nodes regional to a lesion, such as a tumor or other persistent lesion. Perilymphatic administration at draining nodes is critical. Peritumoral injection has been associated with little response, increase in the mitotic index of the tumor, even progression and is thus contraindicated. A ten (10) day injection scheme is optimal and a twenty (20) day injection protocol, while effective clinically, tends to reduce TH1 response and likely shifts towards a less desirable TH2 response as measured by lymphoid infiltration into the cancer. Bilateral injections are effective. Where radical neck dissection has occurred, contralateral injection is effective.

The compounds of the present invention (including IRX-2) are administered and dosed to promote protection from apoptosis as well as optimal immunization either to exogenous or endogenous antigen, taking into account the clinical condition of the individual patient, the site and method of administration, scheduling of administration, patient age, sex, and body weight. The pharmaceutically "effective amount" for purposes herein is thus determined by such considerations as are known in the art. The amount is preferably effective to induce immune production and block immune destruction. The amount is also preferably effective to promote immunization, leading to, e.g., tumor reduction, tumor fragmentation and leukocyte infiltration, delayed recurrence or improved survival rate, or improvement or elimination of symptoms.

In the methods of the present invention, the compounds of the present invention can be administered in various ways, although the preferred method is by perilymphatic injection. It should be noted that the compounds can be administered as the compounds themselves or as a pharmaceutically acceptable derivative and can be administered alone or as an active ingredient in combination with pharmaceutically acceptable carriers, diluents, adjuvants and vehicles. The compounds can also be administered intra- or subcutaneously, or peri- or intralymphatically, intranodally or intrasplenically or intramuscularly, intraperitoneally, and intrathoracically. Implants of the compounds can also be useful. The patient being treated is a warm-blooded animal and, in particular, mammals including man. The data presented shows activity of the IRX-2 on humans or cells derived from humans, and therefore the data herein is all directly relevant and applicable to humans. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days, although preferably a 10 day injection scheme is used. When administering the compound of the present invention, it is generally formulated in a unit dosage injectable form (e.g., solution, suspension, or emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with several of the other ingredients, as desired.

A pharmacological formulation of the present invention can be administered to the patient in an injectable formulation containing any compatible carrier, such as various vehicles, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those disclosed in U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

The invention is further described in detail by reference to the following experimental examples. These examples are provided for the purpose of illustration only, and are not intended to be limiting unless otherwise specified. Thus, the present invention should in no way be construed as being limited to the following examples, but rather, be construed to encompass any and all variations which become evident as a result of the teaching provided herein.

EXAMPLES

Materials and Methods

All steps relating to cell culture are performed under sterile conditions. General methods of cellular immunology not described herein are performed as described in general references for cellular immunology techniques such as Mishell and Shiigi (Selected Methods in Cellular Immunology, 1981) and are well known to those of skill in the art.

Antibodies and Reagents:

The following monoclonal antibodies were used for flow cytometry analysis: anti-CD3-ECD, -CD8-PCS, -CD4-PE (Beckman Coulter, Miami, Fla.); anti-Bcl-2-FITC, -Bcl-2-PE, -Fas-FITC, -FasL-PE (BD Biosciences, San Jose, Calif.); anti-Bax-FITC, -Bcl-xL-FITC (Santa Cruz Biotechnology, Santa Cruz, Calif.) and anti-Bid-antibody (Abcam Inc., Cambridge, Mass.). Polyclonal antibodies were: anti-Bim (Cell Signaling, Danvers, Mass.), anti-FLIP (GenWay Biotech, San Diego, Calif.), and anti-Mcl-1 (Santa Cruz Biotechnology). FITC-conjugated Annexin V was purchased from Beckman Coulter. FITC-conjugated anti-rabbit IgG was purchased from Jackson ImmunoResearch Laboratories (West Grove, Pa.) and the isotype controls ($IgG_1$-FITC, $IgG_{2a}$-FITC and $IgG_{2b}$-FITC and IgG2-PE) were purchased from BD Biosciences. Antibodies purchased for Western Blot analysis included: polyclonal phospho-Akt (Ser473), polyclonal total-Akt, monoclonal phospho-STAT5 (Tyr694) and monoclonal total-STAT5 (Cell Signaling), monoclonal Bcl-2, monoclonal CD3-ζ, monoclonal JAK3, polyclonal SOCS-2 and polyclonal Mcl-1 (Santa Cruz Biotechnology), polyclonal caspase-3, polyclonal FasL antibody-3 (BD Biosciences) and monoclonal β-actin (Sigma Aldrich, St. Louis, Mo.). Anti-Fas (CH-11) agonistic monoclonal antibody, IgM isotype control for CH-11, anti-Fas blocking monoclonal antibody, clone ZB4, and isotype IgG1 control for ZB4 were all purchased from Upstate Biotechnology (Lake Placid, N.Y.). All cell culture reagents including AIM V medium, RPMI 1640 medium, phosphate-buffered saline (PBS), heat-inactivated fetal calf serum (ΔFCS), streptomycin, penicillin, I-glutamine, recombinant trypsin-like enzyme (TrypLE) and trypan blue dye were purchased from Gibco/Invitrogen (Grand Island, N.Y.). The human recombinant cytokines, rhIL-2, rhIL-7 and rhIL-15, were purchased from Peprotech Inc. (Rocky Hill, N.J.). Bovine serum albumin (BSA), saponin, etoposide and staurosporine were from Sigma Aldrich. 7-amino-actinomycin D (7AAD) and the pan caspase inhibitor, z-VAD-FMK, were obtained from BD Biosciences. The selective inhibitor of Akt1/Akt2 was purchased from Calbiochem (San Diego, Calif.) and the selective inhibitors for caspase-3, caspase-8 and caspase-9 from R&D Systems (Minneapolis, Minn.).

Preparation of Primary Cell Derived Biologic (IRX-2):

The method of making the primary cell derived biologic is generally described in U.S. Provisional Patent Application No. 61/044,674. Mononuclear cells (MNCs) are purified to remove contaminating cells by loading leukocytes onto lymphocyte separation medium (LSM) and centrifuging the medium to obtain purified MNCs with an automated cell processing and washing system. The MNCs are then stored overnight in a FEP lymphocyte storage bag. An induction mixture of the MNCs is stimulated with a mitogen, preferably phytohemagglutinin (PHA), and ciprofloxacin in a disposable cell culture device and a primary cell derived biologic is produced from the MNCs. The mitogen is removed from the induction mixture by filtering and tangential flow filtration mode, and then the induction mixture is incubated. The induction mixture is clarified by filtering to obtain a primary cell derived biologic supernatant. Finally, the primary cell derived biologic supernatant is cleared from DNA and adventitious agents by applying anion exchange chromatography and 15 nanometer filtration and optionally further inactivation by ultraviolet-C (UVC). The final product can then be vialed and stored for future administration to a patient.

Cells and Cell Lines:

The head and neck squamous cell carcinoma (H&NSCC) cell line PC-13 was established in Applicants' laboratory and maintained as previously described. It was retrovirally transfected with the human FasL gene obtained from Dr. S. Nagata (Osaka Biosciences Institute, Osaka, Japan) as previously reported. Supernatants of transfected PCI-13-cells (PCI-13-FasL), which contained both sFasL and the 42 kDa membranous form of FasL, were used as a source of tumor-derived microvesicles (MV). Jurkat cells were obtained from American Tissue Culture Collection (ATCC, Manassas, Va.) and were transfected with CD8. The CD8+ Jurkat cells were cultured in RPMI 1640 medium supplemented with 10% (v/v) fetal bovine serum (FBS), L-glutamine and antibiotics. Human T lymphocytes were isolated from peripheral blood mononuclear cells (PBMC) obtained from consented normal donors. PBMC were isolated by Ficoll-Hypaque density gradient centrifugation (GE Healthcare Bio-Sciences Corp., Piscataway, N.J.), washed and plated for 1 hour at 37° C. in culture flasks (T162) in an atmosphere of 5% $CO_2$ to remove CD14+ monocytes. The non-adherent T-lymphocyte fraction was collected and immediately used for experiments or cryopreserved. CD8+ T cells or CD4+ T cells were purified by positive selection using CD8 MicroBeads or CD4 MicroBeads, respectively (Miltenyi Biotec, Auburn, Calif.) using the AutoMACS system according to the manufacturer's instructions. Purified CD8+ or CD4+ T cells were then cultured for 2-3 days in AIM V medium supplemented with 10% FBS in the presence of beads coated with anti-CD3 and anti-CD28 antibodies (T Cell Activation/Expansion Kit, Miltenyi Biotec). All cells used for the above described experiments were in the log phase of growth.

Isolation of Microvesicles:

Microvesicles (MV) were isolated from culture supernatants of the FasL-transfected PCI-13 cell line as previously described. Briefly, the concentrated cell culture supernatants were fractioned by a two-step procedure, including size exclusion chromatography and ultracentrifugation. PCI-13-FasL supernatants were concentrated at least 10 times using Centriprep Filters (Fisher Scientific, Pittsburgh, Pa.). Next, 10 mL aliquots of concentrated supernatants were applied to a Sepharose 2B (Amersham Biosciences, Piscataway, N.J.) column (1.5×35 cm) equilibrated with PBS. One milliliter fractions were collected and the protein content was monitored by measuring absorbance at 280 nm. The exclusion peak material, containing proteins of >50 million kDA, was then centrifuged at 105,000×g for 2 hours at 4° C. The pellet was resuspended in 300-500 μl of sterile PBS. Protein concentration in each MV preparation was estimated by a Lowry's protein assay (Bio-Rad Laboratories, Hercules, Calif.) with bovine serum albumin (BSA) used as a standard.

Western Blot Assays:

To determine total or phosphorylated forms of Akt, Bcl-2, CD3ζ, caspase-3, JAK3, STAT5, FLIP, and Mcl-1, Jurkat CD8+ cells or purified activated CD8+ or CD4+ T-cells were co-incubated with MV at the indicated concentration and/or with IRX-2 (1:3 final dilution) for the indicated period of time at 37° C. The cells were then washed, centrifuged at 4° C. and lysed in equal volumes of ice-cold lysis-buffer (50 mM Tris-HCL pH 7.5, 150 mM NaCl, 0.5% Nonidet P-40) and protease inhibitor cocktail (Pierce Chemical Co., Rockford, Ill.). After lysis, the homogenates were clarified by centrifugation. The supernatants were isolated, and boiled for 5 minutes in 5× Laemmli sample buffer. Proteins were separated by sodium dodecyl sulfate-polyacrylamide gel electrophoresis (SDS-PAGE) and electrotransfered to polyvinylidene difluoride (PVDF) membranes. The membranes were blocked in 5% fat-free milk or 5% BSA in TTBS (0.05% Tween 20 in Tris-buffered saline) for 1 hour at room temperature (RT) and then incubated overnight at 4° C. with the appropriate antibodies. After washing (3×15 minutes) with TTBS at RT, membranes were incubated with horseradish peroxidase-conjugated secondary antibody at 1:150,000 dilution (Pierce Chemical Co) for 1 hour at RT. After washes, membranes were developed with a SuperSignal chemoluminescent detection system (Pierce Chemical Co). To reprobe with another primary antibody, membranes were incubated in stripping buffer (0.5 M NaCl, 3% (v/v) glacial acetic acid), washed and then used for further study.

Co-Incubation of CD8+ Jurkat Cells or Activated Normal T-Lymphocytes with MV and IRX-2:

CD8+ Jurkat cells or activated normal T lymphocytes were plated at 0.3×$10^6$ cells per well in a 96-well plate and pretreated or not with IRX-2 or with recombinant human cytokines at a final concentration of 10 ng/mL or 100 IU/mL for 24 hours (unless otherwise noted). MV (10 μg protein per 0.3× $10^6$ cells) were then added for 3-24 hours. In some experiments, cells were first co-incubated with MV for 3-24 hours, then washed and treated further with IRX-2 or cytokines or treated for the indicated time period with MV and IRX-2 added simultaneously. In selected blocking experiments, anti-Fas neutralizing monoclonal antibody, ZB-4, the pan-caspase inhibitor, Z-VAD-FMK, or the specific Akt-inhibitor or specific inhibitors for caspase-3, caspase-8 and caspase-9 were added at the indicated concentrations prior to MV co-incubation.

Cell Surface Staining:

MV and/or IRX-2 co-incubated CD8+ Jurkat cells or activated T-lymphocytes (at least 300,000 cells/tube) were washed twice in staining buffer (0.1% w/v BSA and 0.1% w/v $NaN_3$). Cells were stained for cell surface markers as previously described. Briefly, cells were incubated with the optimal dilution of each antibody for 20 minutes at RT in the dark, washed twice with staining buffer and finally fixed in 1% (v/v) paraformaldehyde (PFA) in PBS. The following antibodies were used for surface staining: anti-CD3-ECD, anti-CD4-PE, anti-CD8-PCS, anti-Fas-FITC and anti-FasL-PE.

Flow Cytometry:

Four color flow cytometry was performed using a FACS-can flow cytometer (Beckman Coulter) equipped with Expo32 software (Beckman Coulter). Lymphocytes were gated based on morphology, and debris, MV as well as monocytes and granulocytes were excluded, collecting data on at least $10^5$ cells. For the analysis of activated primary T lymphocytes, gates were restricted to the $CD3^+$ $CD8^+$ or $CD3^+$ $CD4^+$ T-cell subsets. Data was analyzed using Coulter EXPO 32vl.2 analysis software.

Annexin V Binding Assay:

Annexin V (ANX) binding to MV and/or IRX-2 co-incubated CD8+ Jurkat cells or activated T lymphocytes was measured by flow cytometry to evaluate spontaneous or in vitro induced apoptosis. Following surface-staining with antibodies to CD3, CD8 or CD4, the cells were resuspended in Annexin-binding buffer and incubated with FITC-conjugated Annexin V for 15 minutes on ice. Additional staining with 7-amino-actinomycin D (7-AAD) was performed to discriminate dead and live cells. The cells were analyzed by flow cytometry within 30 minutes of staining.

Measurement of Caspase Activation:

Total cellular Caspase activity was tested by intracellular staining of activated caspases using a pan caspase inhibitor, CASPACE FITC-VAD-FMK In Situ Marker (Promega, Madison, Wis.). Cells were resuspended in PBS and FITC-VAD-FMK was added at a final concentration of 5 µM. The cells were incubated for 20 minutes at 37° C., 5% $CO_2$ and washed with PBS. Then cells were stained for cell surface receptors, fixed with 1% paraformaldehyde and analyzed by flow cytometry. The specific activation of caspase-3 and caspase-7 was measured using the VYBRANT FAM caspase-3 and -7 Assay Kit from Invitrogen (Carlsbad, Calif.) according to the manufacturers' instructions. Briefly, cells were resuspended in PBS and stained with a 150× dilution of the carboxyfluorescein (FAM)-labeled FMK-caspase inhibitor for 60 minutes at 37° C., 5% $CO_2$. Then the cells were washed in wash buffer and fixed with 1% paraformaldehyde. The cells were analyzed by flow cytometry with the fluorescein measured on the FL1 channel.

Measurement of the Mitochondrial Membrane Potential:

The loss of mitochondrial membrane potential (MMP) as a hallmark of apoptosis was measured using the MITOPROBE JC-1 Assay Kit from Invitrogen (Carlsbad, Calif.). The cationic dye JC-1 (5,5',6,6'-tetrachloro-1,1',3,3'-tetraethylbenzimidazolylcarbocyanine iodide) exists in healthy cells as a green monomer in the cytosol and also accumulates as red aggregates in the mitochondria. In apoptotic and necrotic cells, JC-1 remains only in the cytoplasm due to mitochondrial depolarization, which can be detected by flow cytometry as a decrease in the red/green fluorescence intensity ratio. CD8+ Jurkat cells or activated T lymphocytes were incubated in PBS containing 2 µM of JC-1 for 30 minutes at 37° C., 5% $CO_2$. An aliquot of the cells was treated with 50 µM of the mitochondrial uncoupler carbonyl cyanide 3-chlorophenylhydrazone (CCCP) during the staining period as a positive control for mitochondrial depolarization. The cells were analyzed using a flow cytometer immediately after staining.

Evaluation of Apoptosis-Related Proteins:

Expression of anti-apoptotic proteins Bcl-2, Bcl-xL, FLIP and Mcl-1 and the pro-apoptotic proteins Bax, Bim and Bid was investigated in CD8+ Jurkat cells or activated primary T lymphocytes using multicolor flow cytometry. The cells were first stained for surface T-cell markers as described above. For intracellular staining of apoptosis-related proteins the cells were fixed with 1% (v/v) paraformaldehyde in PBS at RT for 10 minutes and then permeabilized with saponin (0.1% v/v in PBS) for 15 minutes at 4° C. Next, the cells were stained for 30 minutes at 4° C. with FITC- or PE-conjugated antihuman Bcl-2, Bax and Bcl-xL or unconjugated antibodies for FLIP, Bim, Bid or Mcl-1, followed by a wash with 0.1% saponin. Samples stained with unconjugated antibodies were further incubated with a FITC-conjugated goat anti-rabbit IgG for 15 minutes at room temperature. After washing with 0.1% saponin, cells were fixed in 1% (v/v) paraformaldehyde. Isotype control matched antibodies were used for both surface and intracellular controls and all antibodies were pre-titered on fresh PBMC.

TUNEL Assay:

DNA fragmentation was measured using the In Situ Cell Death Detection Kit, TMR red (Roche, Indianapolis, Ind.). Briefly, cytospin preparations (100,000 cells/slide) of MV- and IRX-2 treated T cells were air-dried and fixed with 4% (v/v) paraformaldehyde (PFA) in PBS for 1 hour at RT. Slides were rinsed with PBS and incubated with permeablization solution (01% Triton X-100 in 0.1% sodium citrate) for 2 minutes on ice. Then the slides were washed twice with PBS and incubated with 20 µl of the TUNEL reaction mixture for 1 hour at 37° C. in a humidified chamber in the dark. Then the samples were washed extensively with PBS and incubated in a medium with 4',6-diamidino-2-phenylindole (DAPI; Vector Laboratories, CA) to trace cell nuclei. Slides were evaluated in a Nikon Eclipse E-800 fluorescence microscope under ×200 magnification. For digital image analysis, Adobe Photoshop 6.0 was used. A minimum of 300 cells were randomly counted in a microscopic field to determine the percentage of cells with DNA fragmentation.

Statistical Analysis:

Statistical analysis was performed using the Student's t-test. P values <0.05 were considered significant.

Example 1

Figure 4:
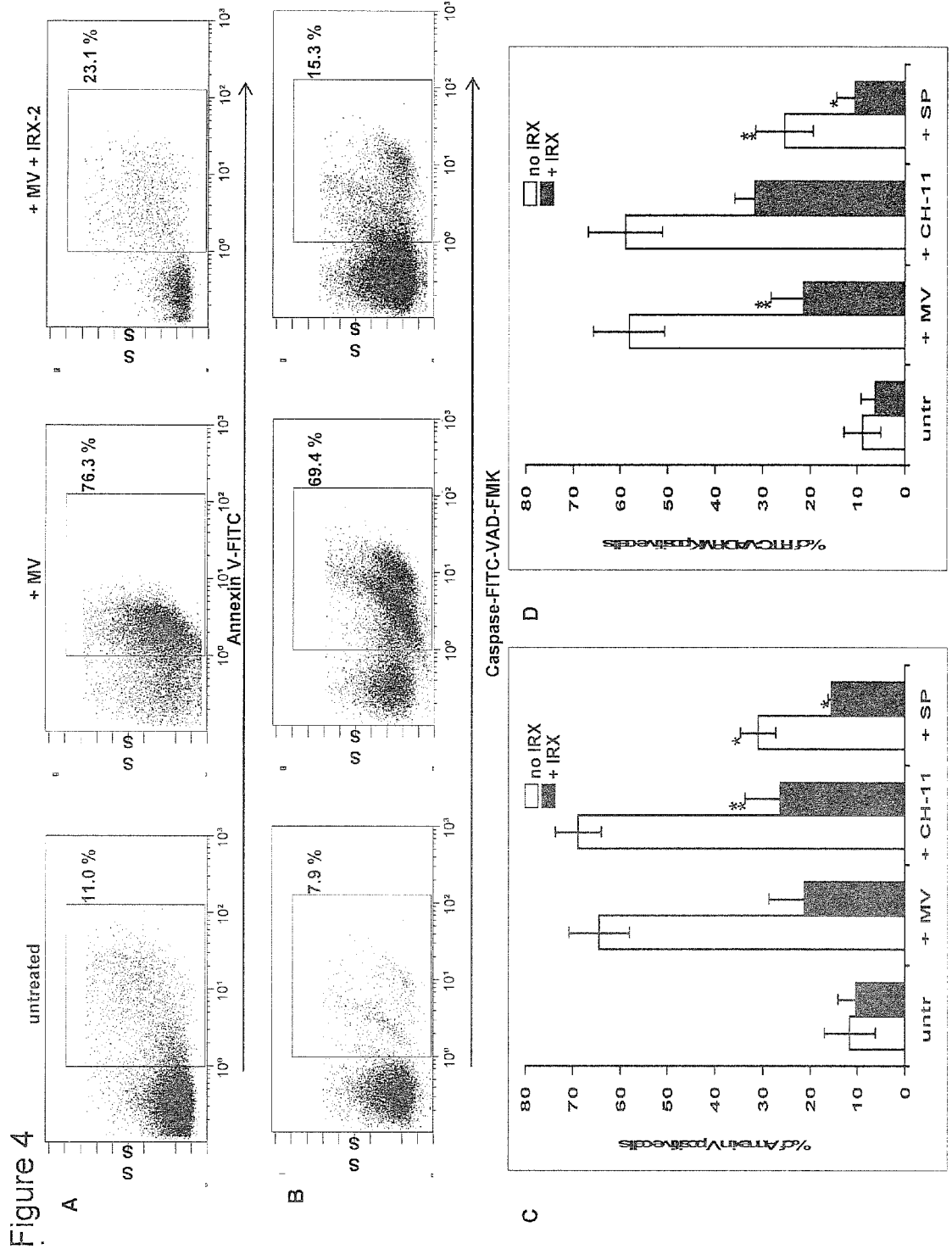
FIG. 4A shows CD8+ Jurkat cells analyzed for Annexin V binding by flow cytometry.
FIG. 4B shows Caspase activation detected by FITC-VAD-FMK staining and flow cytometry.
FIG. 4C shows mean percentage+/−standard deviation (SD) of Annexin V-positive/7-AAD-negative Jurkat cells following incubation with various apoptosis-inducing agents.
FIG. 4D shows mean percentage+/−SD of FITC-VAD-FMK+ Jurkat T cells following incubation with various apoptosis-inducing agents.

IRX-2 Protects Both Jurkat T Cells and Primary T Lymphocytes from Cell Death Mediated by a Variety of Apoptosis-Inducing Agents To determine whether IRX-2 protects T cells from apoptosis mediated by tumor-derived microvesicles (MV), CD8+ FasL-sensitive Jurkat cells were pre-incubated with a 1:3 dilution of IRX-2 (approximately 4 ng/mL or 90 IU/mL IL-2) for 24 hours and subsequently treated them with 10 µg of tumor-derived MV (10 µg), CH-11 (400 ng/mL) or staurosporine (1 µg/mL) for 3 hours. As shown in Applicants' previous studies, the co-incubation of Jurkat cells with MV caused marked apoptosis, demonstrated by enhanced Annexin V binding (FIGS. 4A and 4C) and binding of FITC- VAD-FMK indicative of caspase activation (FIGS. 4B and 4D). Dead cells (7-AAD+) were excluded and the gate was set on 7-AAD negative CD8+ Jurkat cells. Upon pre-incubation of Jurkat T cells with IRX-2, the MV-induced apoptosis, as detected by both assays, was significantly reduced (FIGS. 4A-4D).

Figure 12:
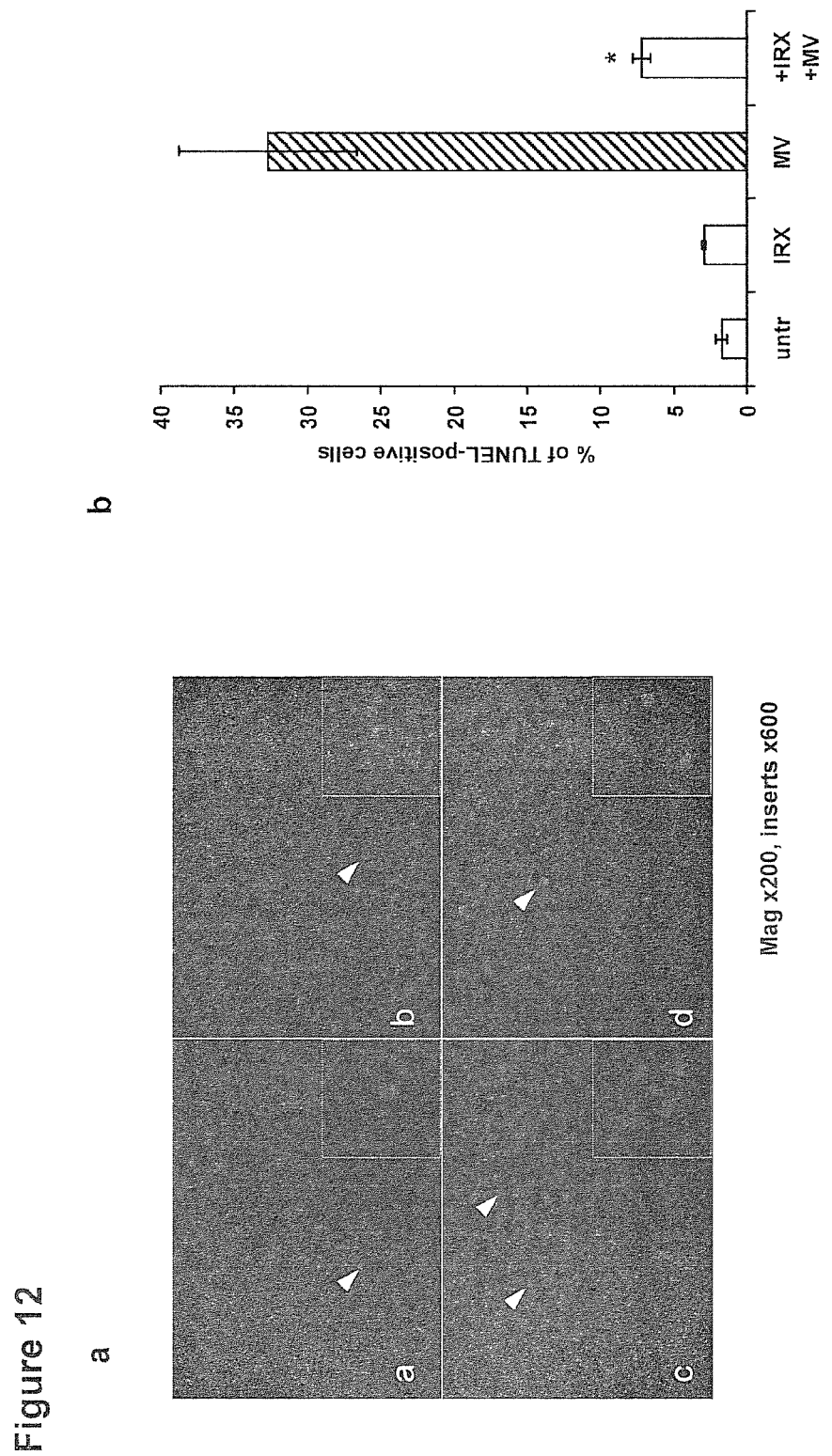
FIG. 12A is a fluorescent microscopy of CD8+ Jurkat cells which were either untreated (a), incubated for 24 hours with IRX-2 alone (b) or MV alone for 24 hours (c) or pre-incubated with IRX-2 for 24 hours and subsequently treated with MV for 24 hours (d) and then stained by the TUNEL method to reveal DNA strand breaks (red nuclei) indicative of apoptosis.
FIG. 12B is a graph of percentage of TUNEL-positive CD8+ Jurkat cells in the above co-cultures.

Interestingly, it was found that IRX-2 was effective not only against MV-induced apoptosis, but also provided protection of Jurkat T cells against FasL-induced (CH-11-Ab) and cytotoxic drug-induced (staurosporine) apoptosis. FIGS. 12C-12D shows IRX-2 significantly reduced apoptosis induced by each of these agents as measured by decreased Annexin V binding (FIG. 4C) and by reduced caspase activation (FIG. 12D). Results shown in FIG. 4C and FIG. 4D are representative of 3 independent experiments (*p<0.05; ** p<0.002).

IRX-2-mediated protection was also observed when using primary blood-derived CD8+ and CD4+ T lymphocytes. The data in Table 1 illustrates the protective effect of IRX-2 on both MV- or CH-11-induced apoptosis as indicated by decreases in caspase activation in these cells (Table 1). Similar decreases of Annexin V binding were observed with IRX-2 (data not shown). CD8+ T cells showed a significantly greater sensitivity to MV-induced apoptosis than CD4+ T cells, but in both these subsets, IRX-2 pre-treatment provided a strong protection against MV-induced apoptosis, as determined by a total decrease in the percentage of T cells with caspase-activation. IRX-2 also protected both cell subsets from CH-11 Ab induced apoptosis (Table 1). Taken together, these findings indicate that IRX-2 effectively protects primary T cells and cell lines from MV- or anti-Fas CH-11 Ab-induced apoptosis as well as from intrinsic apoptosis associated with staurosporine-induced mitochondrial changes. Such results strengthen the argument that IRX-2 provides significant protection from several different types of apoptotic stimuli including that derived from tumors as well intrinsic mechanisms that may be induced by chemotherapy, radiotherapy or viral infection for example.

TABLE 1

IRX-2 protects activated peripheral blood CD8+ and CD4+ T-lymphocytes from MV- and Fas-induced apoptosis[a]

|  | CD8+ cells | | CD4+ cells | |
| --- | --- | --- | --- | --- |
|  | mean % of FITC-VAD-FMK+ cells ± SD | p-value[b] | mean % of FITC-VAD-FMK+ cells ± SD | p-value[b] |
| untreated cells | 14.8 ± 4.8 |  | 12.6 ± 2.3 |  |
| no IRX-2 + CH-11 Ab | 52.8 ± 4.9 |  | 41.2 ± 9.8 |  |
| +IRX- + CH-11 Ab | 15.0 ± 3.5 | 0.0010 | 15.4 ± 6.1 | 0.0510 |
| no IRX-2 + MV | 68.9 ± 10.4 |  | 49.8 ± 8.0 |  |
| +IRX-2 + MV | 26.5 ± 10.3 | 0.0006 | 13.9 ± 6.4 | 0.0211 |

[a]Activated CD8+ or CD4+ cells were pre-incubated with IRX-2 for 24 hours (at 1:3 final dilution, contains 90 IU/ml IL-2; see Materials and Methods for add'l cytokine conc. details) and then treated with 10 µg MV or CH-11 antibody (Ab) (400 ng/mL) for an additional 24 hours. Cells were analyzed for caspase activation by FITC-VAD-FMK staining via flow cytometry. Results are mean percentage ± SD of 3 independent experiments.
[b]The p values are for differences between no IRX-2 and +IRX-2 treated cells.

Example 2

IRX-2-Mediated Protection from Apoptosis is Time- and Concentration-Dependent

Figure 5:
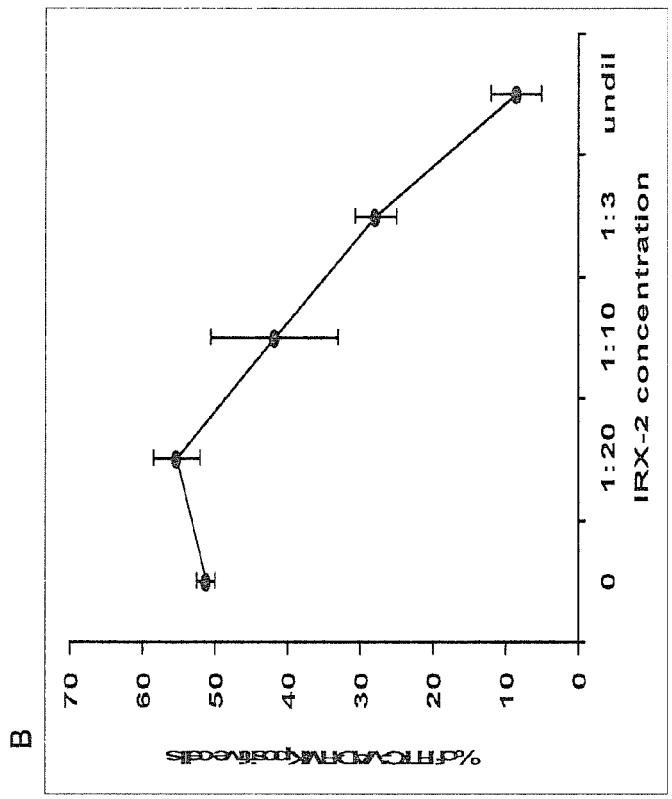
FIG. 5A shows a time-course analysis of CD8+ Jurkat cells.
FIG. 5B shows a concentration-course analysis.
Figure 5:
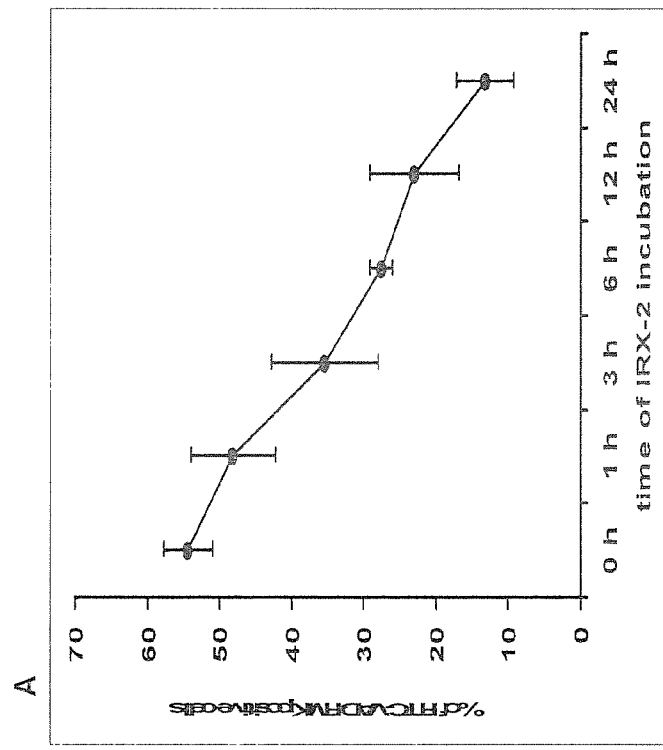

To better understand the protective effects of IRX-2 on T cells, CD8+ Jurkat cells were pre-incubated with IRX-2 (fixed dilution of 1:3=90 IU/ml IL-2) for incrementally longer time periods (0-24 hours) or with increasing concentrations of IRX-2 (as indicated) for a fixed 24 hour period and subsequently treated with MV (10 µg) for 3 hours (FIGS. 5A and 5B, respectively). Apoptosis was assessed using FITC-VAD-FMK staining of activated caspases by flow cytometry. IRX-2 was found to block MV-induced apoptosis, and this inhibition was time-dependent, as extending the time of the pre-incubation with IRX-2 intensified its protective effects. A maximal inhibition was observed after 24 hours of MV treatment (FIG. 5A). Pre-incubation of T cells with different IRX-2 concentrations showed a dose-dependent inhibition of apoptosis caused by MV (FIG. 5). At the highest possible concentration (i.e., undiluted IRX-2), IRX-2 completely inhibited the induction of apoptosis by MV (FIG. 5B). Results are mean percentage±SD of 4 independent experiments. The fact that IRX-2-mediated inhibition is both time and concentration dependent demonstrates pharmacologically that the effects are specific to the drug.

Figure 6:
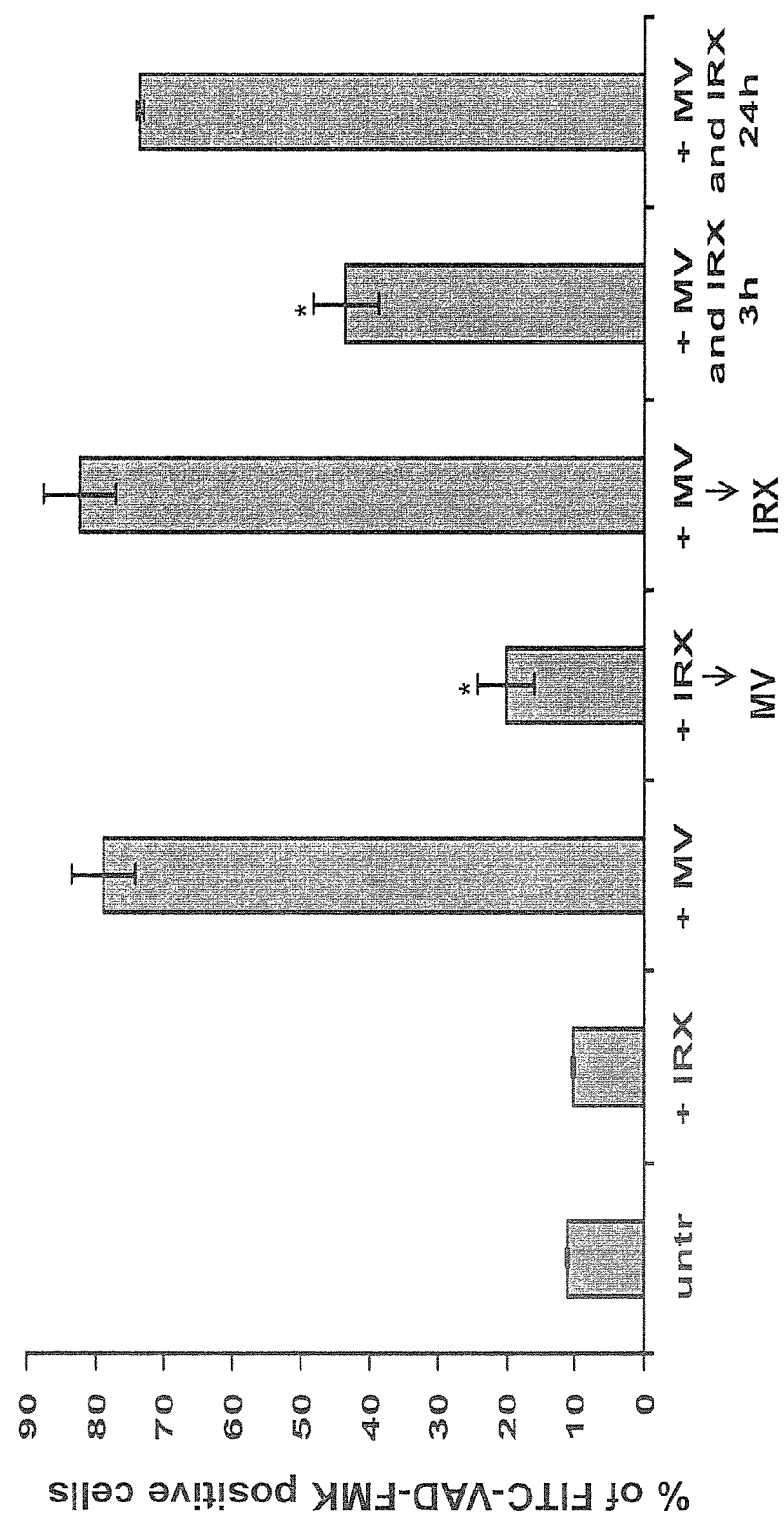
FIG. 6 shows a graph of percentage of FITC-VAD-FMK positive cells for various treatments of CD8+ Jurkat cells.

It was also desired to determine whether IRX-2 could protect T cells from apoptotic cell death once the apoptotic cascade had been initiated. To address this question, CD8+ Jurkat cells were untreated, treated with IRX-2 (1:3 dilution) for 24 hours (+IRX), MV for 3 hours (+MV), pre-incubated with IRX-2 for 24 hours and then treated with MV (10 µg) for 3 hours (+IRX→MV) or first incubated with MV and then treated with IRX-2 (+MV→IRX-2) or incubated with both agents simultaneously (+MV and IRX) for 3 hours or 24 hours, respectively. Activation of caspases was analyzed by flow cytometry. Results are mean percentage±SD from a representative experiment of 3 performed (*p<0.002 compared to MV-treated sample). In comparison to the effects of IRX-2 treatment prior to the addition of MV, apoptosis was reduced by about 50% after simultaneous co-incubation of T cells with MV+IRX-2 (FIG. 6). When IRX-2 was added 3 hours after treatment with MV, the protective effect of IRX-2 was completely abrogated. Since IRX-2 was obviously not able to overcome the apoptotic cascade already initiated by MV, it acts through a protective mechanism rather than through a reversal of ongoing apoptotic processes initiated by MV.

Example 3

Comparison of the Protective Effect of IRX-2 with the Effect of the Survival Cytokines IL-7 and IL-15: Caspase-Activation in Jurkat CD8+ Cells After Treatment with Tumor-MV Jurkat CD8+ cells were plated at a density of 300,000 cells/100 µL/well in a 96 well-plate and incubated for 24 hours with IRX-2 (1:3 final concentration), IL-7 (10 ng/mL), IL-15 (10 ng/mL), or both cytokines (10 ng/ML each), respectively. The cells were treated for 3 hours with PCI-13/FasL-MV (15 µg). Jurkat CD8+ cells heated for 10 minutes at 56 degrees C. were used as a positive control. The cells were harvested, washed in 1 mL PBS, resuspended in 500 µL PBS, and stained with 5 µM VAD-FITC at 37 degrees C. for 20 minutes. Then the cells were washed in PBS and stained for 15 minutes for CD8-PE-Cy5. After washing, the cells were fixed in 1% PFA and analyzed by multiparametric flow cytometry.

Figure 7:
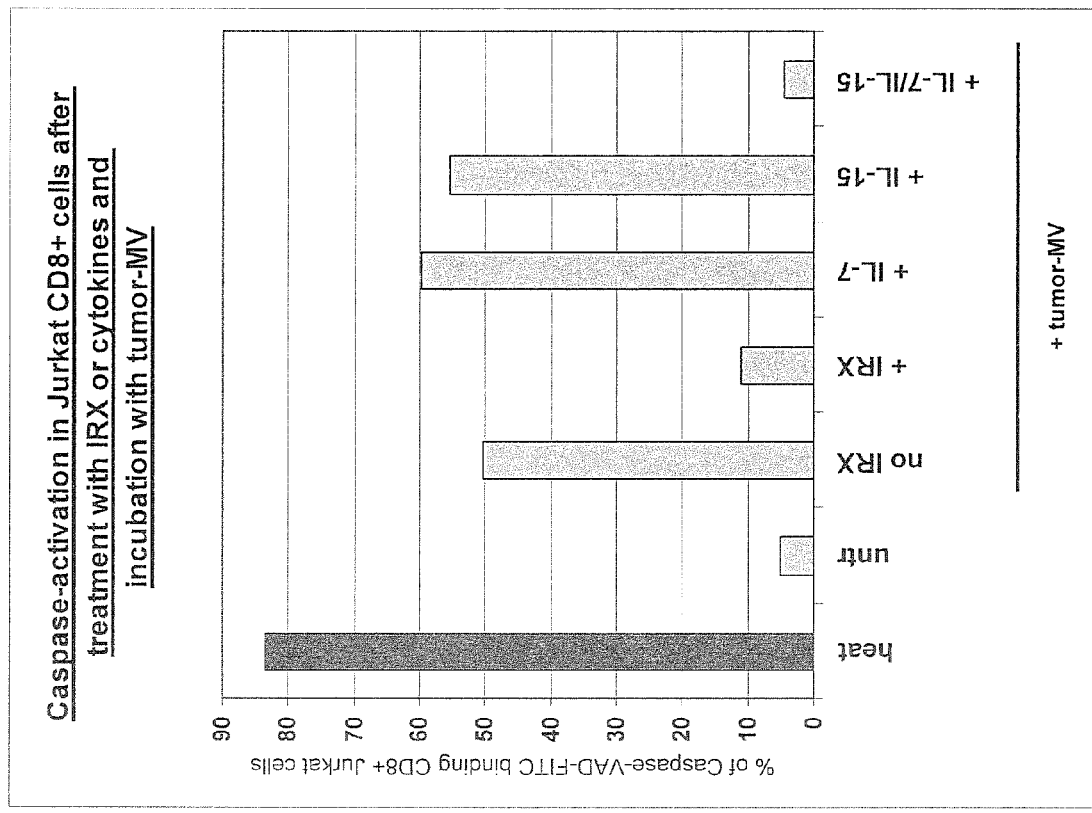
FIG. 7 is a graph of Caspase-activation in Jurkat CD8+ cells after treatment with IRX-2 or cytokines and incubation with tumor-microvesicles (MV)

The percent of activated caspase-VAD-FITC binding CD8+ Jurkat cells were determined for each treatment group as shown in FIG. 7. The MV-induced apoptosis (no IRX-2 lane; 50% cells undergoing apoptosis) was dramatically inhibited by pre-treatment with either IRX-2 alone (11% apoptotic cells=4.5 fold reduction) or a mixture of IL-7 and IL-15 (5% apoptotic cells=10 fold reduction). Singly, neither IL-7 nor IL-15 alone was able to reduce the level of apoptosis below the control MV-induced level. IRX-2 does not contain either IL-7 or IL-15 both of which are recognized as potent "survival" factors of lymphoid cells. This demonstrates that the apoptosis-inhibiting activity of IRX-2 is the result of a synergistic combination of biologically active components and cannot be reproduced by a single recombinant cytokine.

Example 4

Figure 8A:
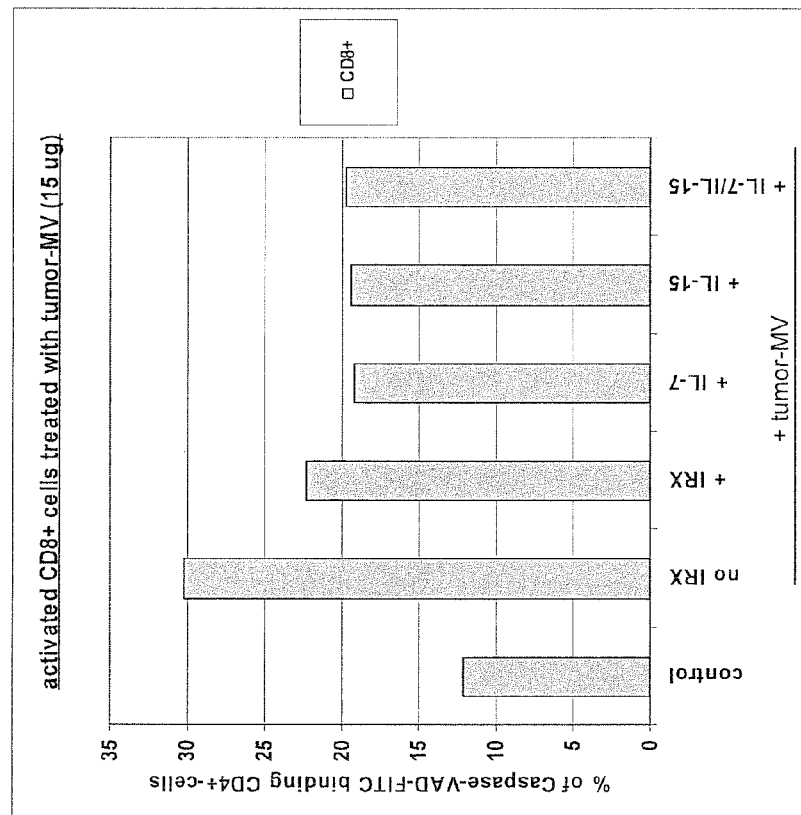
FIG. 8A is a graph of human peripheral blood pre-activated CD4+ cells and FIG. 8B is a graph of human peripheral blood pre-activated CD8+ cells treated with tumor-MV (15 µg) and pre-treated with the indicated cytokines or IRX-2.
Figure 8B:
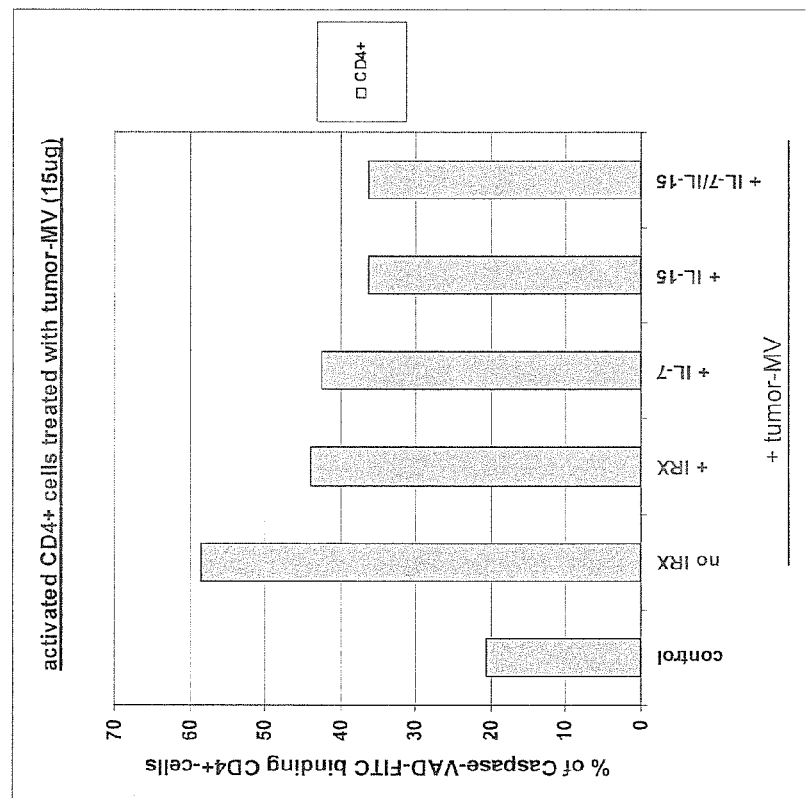
Figure 9A:
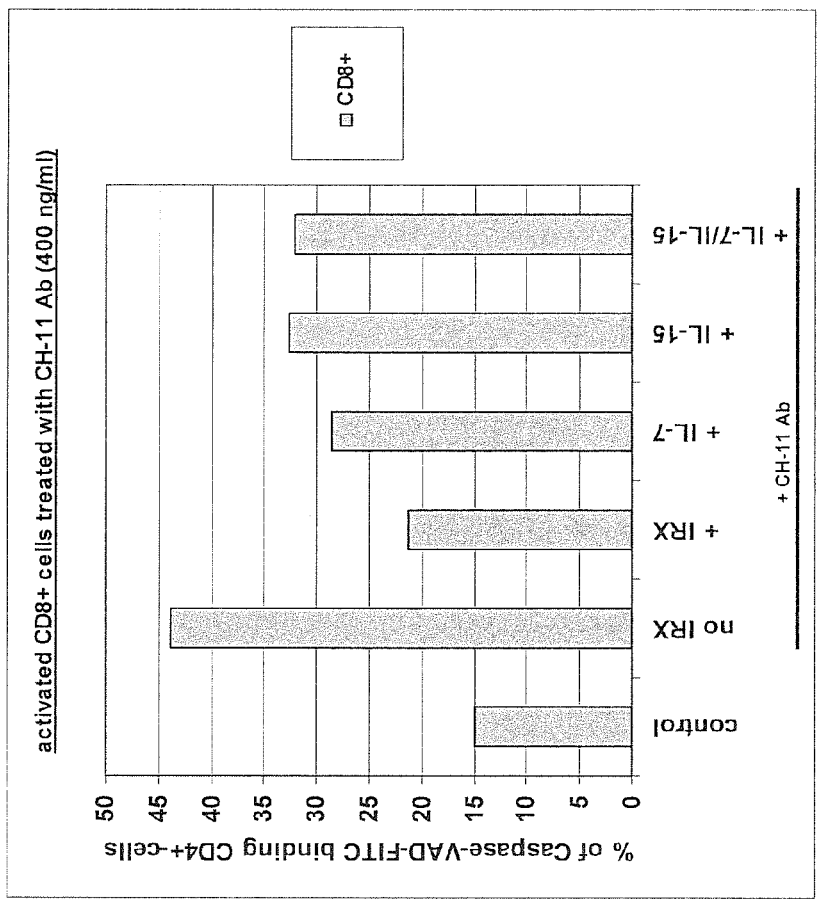
FIG. 9A is a graph of activated human peripheral blood pre-activated CD4+ cells and FIG. 9B is a graph of human peripheral blood pre-activated CD8+ cells treated with CH-11 Ab (400 ng/mL) following pre-treatment with the indicated cytokines or IRX-2.
Figure 9B:
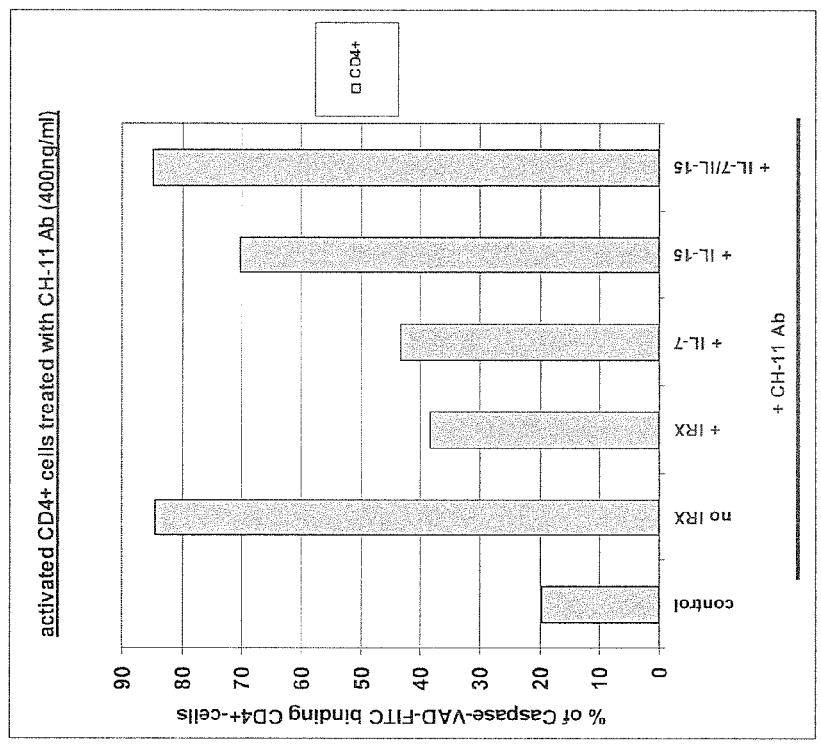

Protective Effect of IRX-2 and Survival Cytokines IL-7 and IL-15: Caspase-Activation in Activated CD8+ and CD4+ T-Cells after Treatment with Apoptosis Inducers Non-adherent cells from leukocyte units (buffy coats) were thawed, $60\times10^6$ cells (in 60 mL 10% FCS, RPMI-medium) were activated with CD3/CD28 Dynal beads (1 bead/cell) for 3 days. After activation, cells were washed and CD8+ and CD4+ cells were isolated by magnetic separation (positive selection, Miltenyi MicroBeads). 300,000 cells were plated in 96 well-plates in 100 μL/well and incubated with IRX-2 (1:3) or the cytokines Il-7 and IL-15 (100 ng/mL) for 24 hours. The cells were then treated for an additional 24 hours with PCI-13/FasL-MV (15 μg) (FIGS. 8A, 8B) or CH-11 Ab (400 ng/mL) (FIGS. 9A, 9B) to induce apoptosis.

After incubation, the cells were harvested, washed in 1 mL PBS, resuspended in 300 μL PBS and stained with 3 μM VAD-FITC at 37 degrees C. for 20 minutes. The cells were washed in PBS and stained for 15 minutes for CD8-PE-Cy5 or CD4-PE-Cy5, as indicated. After washing, the cells were fixed in 1% PFA and analyzed by multiparametric flow cytometry.

In response to apoptosis induction via tumor cell line PCI-13/FasL-MV, the percentage of cells binding caspase-VAD-FITC (indicator of cells were undergoing apoptosis) was determined for pre-activated human peripheral blood-derived CD4+ (FIG. 8A) or CD8+ (FIG. 8B) cells that had been pre-incubated with IRX-2 alone or the indicated recombinant cytokines. These data show that IRX-2 is able to inhibit apoptosis as seen previously on Jurkat CD8+ cells (FIG. 4-6) however the degree of inhibition appears less than what was observed on Jurkat cells. In this experimental situation where primary human (non-cell line) T cells are employed, IL-7 and IL-15 were similarly effective compared to IRX-2, either alone or combined. This apparent difference is most likely related to the use of a heterogeneous T cell population from peripheral blood rather than the cloned homogeneous Jurkat cell line. Nevertheless, in either situation and on both CD4+ and CD8+ populations, IRX-2 did indeed inhibit apoptosis in response to the tumor-derived MV.

In an extension to the above findings, a similar experiment was undertaken to evaluate percent caspase-VAD-FITC binding of pre-activated human peripheral blood-derived CD4+ (FIG. 9A) or CD8+ (FIG. 9B) cells in this case treated with an alternative apoptosis inducer, anti-Fas antibody (CH-11). In this context, IRX-2 is the most effective at inhibiting apoptosis induction compared to either IL-7 or IL-15 or both combined. This was true for both the CD4+ and CD8+ populations taken from normal blood donors. Such results strengthen the argument that IRX-2 provides significant protection from several different types of apoptotic stimuli including that derived from tumors.

Example 5

The Survival Signals Promoted by IRX-2 Greater than the Protective Effects of Other Recombinant Survival Cytokines Since IL-2 is a principal cytokine in IRX-2 (~90 IU/mL IL-2 at the 1:3 dilution used), the observed anti-apoptotic activity of IRX-2 could be in part IL-2-dependent. On the other hand, synergy with other cytokines present in IRX-2 could promote survival. Activated CD8+ and CD4+ T-cells were incubated with either 100 IU/mL of recombinant human IL-2, a dose approximating that present in the 1:3 IRX-2 dilution, or IRX-2 (~90 IU/mL at 1:3) and compared for the ability to inhibit MV- or CH-11 antibody-induced apoptosis. As shown in Table 2A, IL-2 had a similar protective effect against MV-induced apoptosis as IRX-2 in CD8+ T cells, but had a lower protective effect in CD4+ T cells. In terms of protection against CH-11Ab-induced apoptosis, IL-2 was significantly much less effective than IRX-2 in enhancing survival of CD4+ T cells and had almost no effect in CD8+ T cells (Table 2B). These findings indicate that the survival-enhancing potential of IRX-2 is greater than that of its main cytokine IL-2 and that support by other cytokines that are present in IRX-2 at very low physiological concentrations contribute to these effects.

It is likely that cytoprotective effects of IL-2 in IRX-2 are enhanced by the presence of IFNγ and GM-CSF, which in combination, could mediate immuno-potentiating effects. The role of other components of IRX-2 (e.g., IL-1α, IL-6, IL-8, TNFα) in promoting T-cell survival is less clear, although studies have shown that, depending on tissue location and concentration, some of these pro-inflammatory cytokines can also support anti-tumor immune responses. It is important to note that a functional synergism amongst the various components of IRX-2 was previously described, demonstrating, for example, that IRX-2 was able to induce maturation of dendritic cells to a greater extent than comparable levels of TNFα alone.

Additionally, the protective effect of IRX-2 was compared with the activity of recombinant IL-7 and IL-15, both potent survival cytokines for lymphocytes, which are not present in the IRX-2 mixture. Pre-incubation of T cells with these cytokines at a concentration of 10 ng/mL, alone or in combination, provided protection from MV-induced or CH-11 Ab-induced apoptosis in all cases, although to different extents (Table 2A and B). IL-7 alone only weakly inhibited both CH-11 Ab- and MV-induced apoptosis in both cells subsets in comparison to IRX-2. IL-15 alone was as potent as IRX-2 in protection against MV-induced apoptosis but provided a weaker survival signal against CH-11 Ab-induced apoptosis. A combination of both cytokines blocked apoptosis in CD8+ and CD4+ cell subsets, and the level of apoptosis inhibition was similar to that mediated by IRX-2, but only in case of MV-induced apoptosis (Table 2A and B). Thus, the protective effects of IRX-2 were comparable to or in some cases (e.g., protection of CD8+ cells) even stronger than those of the recombinant survival cytokines, IL-7 and IL-15 in protecting CD4+ cells. IRX-2 was found to be significantly more effective than recombinant IL-7 in protecting activated CD4+ and CD8+ T cells from MV- and CH-11 Ab-induced apoptosis and had similar protective effects as IL-15. Among the cytokines tested, IRX-2 had the greatest survival potency when CH-11 Ab was used to induce apoptosis, implying protection against receptor-mediated apoptosis. It should be noted that the concentrations of IL-7 and IL-15 used in these experiments are relatively high and not physiological levels, again suggesting a strong synergy between the components of IRX-2.

TABLE 2

Anti-apoptotic effects of IRX-2 in comparison to IL-2, IL-7 and IL-15 in (a) MV-induced or (b) CH-11 Ab-induced[a] apoptotic primary T cells.

| | CD8+ cells | | CD4+ cells | |
|---|---|---|---|---|
| | mean % of FITC-VAD-FMK+ cells ± SD | p-value[b] | mean % of FITC-VAD-FMK+ cells ± SD | p-value[b] |
| A. MV-induced apoptosis | | | | |
| control | 21.8 ± 3.9 | | 14.3 ± 5.0 | |
| no IRX-2 + MV | 63.2 ± 4.5 | | 52.8 ± 8.7 | |
| +IRX-2 + MV | 20.6 ± 0.8 | 0.0006 | 10.2 ± 0.4 | 0.0038 |
| +IL-7 + MV | 49.5 ± 3.5 | 0.0004 | 34.5 ± 1.9 | 0.0124 |
| +IL-15 + MV | 16.8 ± 6.2 | 0.0044 | 16.7 ± 2.1 | 0.0072 |
| +IL-7/IL-15 + MV | 11.8 ± 6.2 | 0.0036 | 11.9 ± 0.8 | 0.0031 |
| +IL-2 + MV | 21.9 ± 2.7 | 0.0002 | 22.2 ± 2.7 | 0.0113 |
| B. CH-11 Ab-induced apoptosis | | | | |
| control | 12.3 ± 2.8 | | 11.4 ± 1.3 | |
| no IRX-2 + MV | 50.0 ± 0.2 | | 46.8 ± 3.0 | |
| +IRX-2 + MV | 13.4 ± 3.0 | 0.0007 | 12.0 ± 1.7 | 0.0001 |
| +IL-7 + MV | 37.7 ± 1.4 | 0.0015 | 31.8 ± 10.6 | |
| +IL-15 + MV | 28.8 ± 3.1 | 0.0020 | 21.1 ± 5.3 | 0.0086 |
| +IL-7/IL-15 + MV | 24.2 ± 4.9 | 0.0028 | 20.2 ± 0.1 | 0.0010 |
| +IL-2 + MV | 44.2 ± 6.9 | | 31.7 ± 3.0 | 0.0128 |

[a]Activated primary CD8+ and CD4+ T-cells were pre-incubated with IRX-2 (1:3 dilution, includes ~90 IU/ml IL-2, see Materials & Methods.), recombinant human IL-2 (100 IU/mL), IL-7 (10 ng/mL), IL-15 (10 ng/mL) or IL-7 and IL-15 (both 10 ng/mL) for 24 hours and then treated with 10 μg MV or 400 ng/mL CH-11 antibody (Ab) for an additional 24 hours. Activation f caspases was analyzed by flow cytometry. Data are mean percentages of FITC-VAD-FMK+ cells ± SD.
[b]The p values refer to significant differences between cells pre-treated with IRX-2 compared to MV alone or cells pre-treated with the cytokine indicated compared to those pre-treatment with IRX-2.

Example 6

Figure 10:
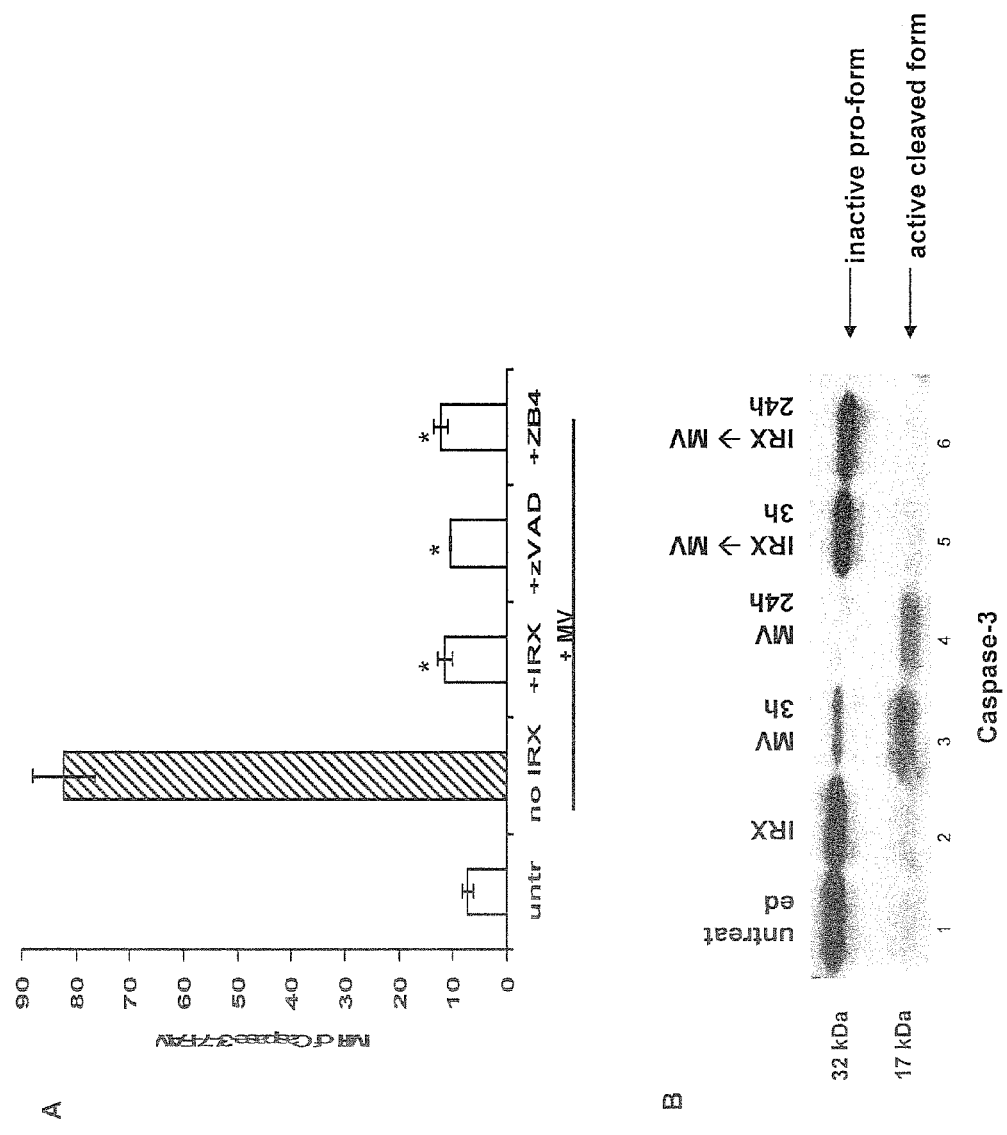
FIG. 10A shows activation of caspases-3 and 7 in CD8+ Jurkat cells assessed via flow cytometry for caspase 3/7-FAM binding.
FIG. 10B shows Western immunoblots showing caspase-3 activation in CD8+ Jurkat cells.
Figure 13:
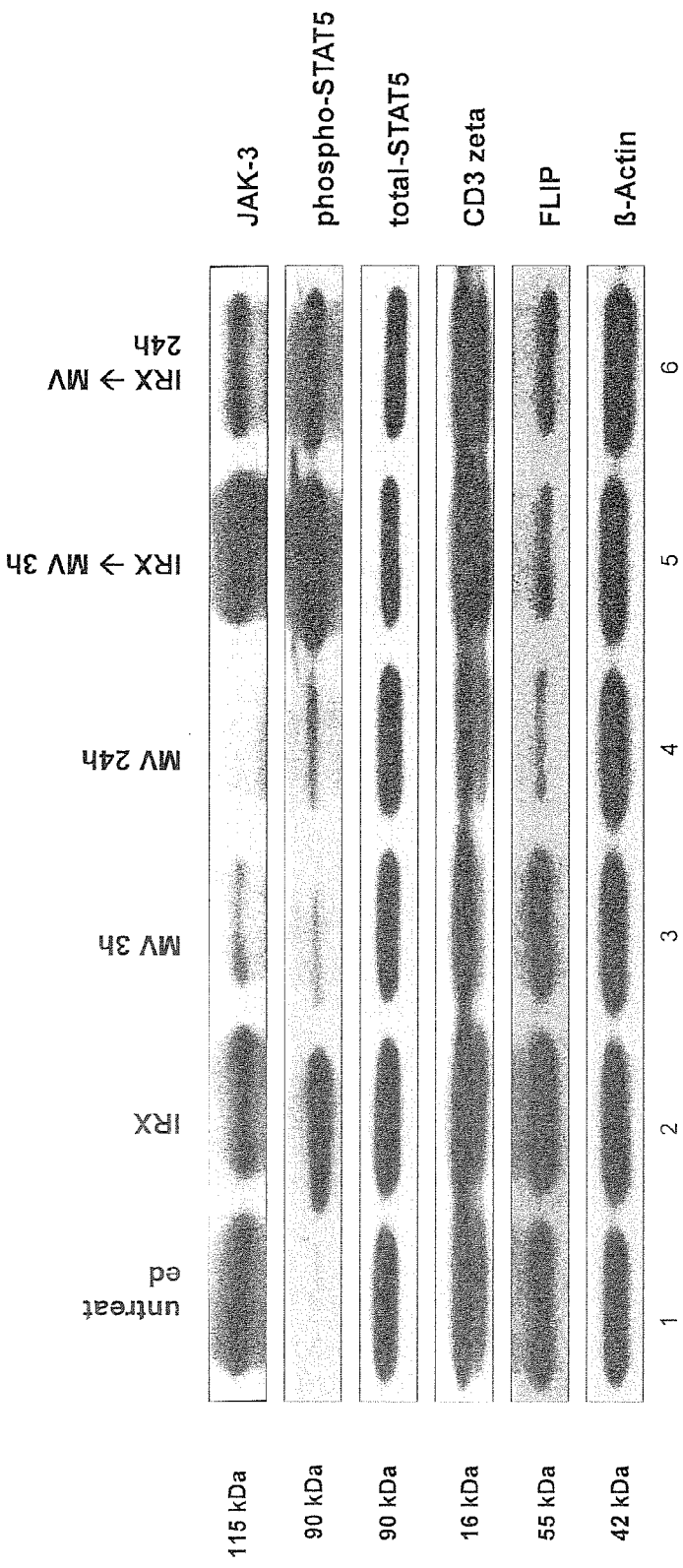
FIG. 13 shows Western blots of CD8+ Jurkat cells with various treatments.

IRX-2 Provides Protection Against MV-Induced Apoptosis at Various Steps in the Apoptotic Pathway Having shown IRX-2-mediated protection extends to primary T cells as well as the Jurkat cell line and several inducing agents, we continued by evaluating the ability of IRX-2 to inhibit downstream steps in the apoptotic process using the co-incubation of Jurkat cells with MV. CD8+ Jurkat cells were either untreated, incubated with 10 μg MV for 3 hours or pre-treated for 24 hours with IRX-2 (1:3 dilution) and then incubated with MV for 3 hours. CD8+ Jurkat cells were also co-incubated with MV and 20 μM of the pan-caspase inhibitor Z-VAD-FMK (zVAD) or co-incubated with MV and the anti-Fas neutralizing mAb ZB4 (10 μg/mL) (controls). Results are the mean MFI±SD of 3 independent experiments. As shown in FIG. 13A, MV-treatment of Jurkat cells led to a very strong increase in the mean fluorescent intensity (MFI) of caspase-3/-7-FAM, a dye which specifically binds to activated caspase-3 and caspase-7, the main effector caspases of both receptor- and mitochondrial-mediated apoptosis. Pretreatment with IRX-2 completely prevented the MV-induced induction of caspase-3 and -7 activity as well as the irreversible caspase inhibitor zVAD and the anti-Fas neutralizing monoclonal antibody (mAb) ZB4. Caspase-3 activation by MV was also detected by Western immunoblot analysis, where a dramatic decrease in the protein level of the inactive caspase-3 pro-form and a simultaneous increase of the active cleaved form was observed in MV-treated Jurkat T cells over 24 hours (FIG. 10B, lanes 3 and 4). IRX-2 pre-treatment effectively blocked induction of the active cleaved form (FIG. 10B, lanes 5 and 6). The cells were either untreated, treated with IRX-2 (1:3 dilution) for 24 hours (+IRX), treated with MV (10 μg) for 3 hours (+MV 3 hours) or 24 hours (+MV 24 hours) or pre-incubated with IRX-2 for 24 hours and then treated with MV (10 μg) for 3 hours or 24 hours (+IRX→MV). Whole cell lysates of the cells were separated on SDS-PAGE and transferred to PVDF membranes for subsequent Western blotting. Activation of caspase-3 is shown as a decrease in the inactive pro-form and the appearance of the active subunits p17 and p10. Results are representative of 3 Western blots.

Figure 11:
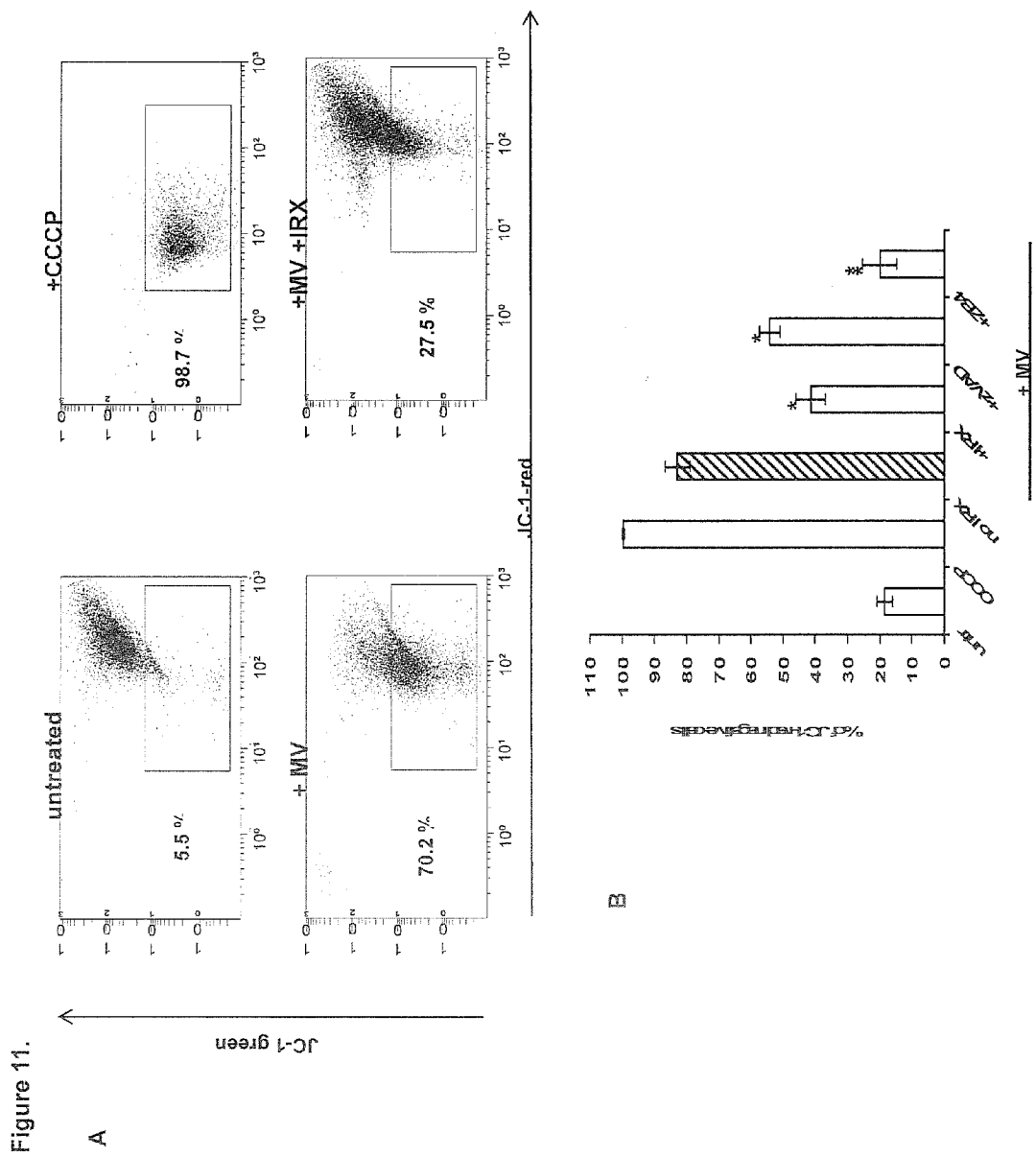
FIG. 11A shows CD8+ Jurkat cells were analyzed by flow cytometry for a decrease in red fluorescence of the cationic dye JC-1, indicating a loss of MMP.
FIG. 11B is a graph of percentage of JC-1 red-negative cells.

In addition, IRX-2 blocked the MV-induced loss of mitochondrial membrane potential (MMP) in Jurkat T cells (FIGS. 11A and 11B). This block was comparable to that provided by the two inhibitors z-VAD and ZB4 (FIG. 11B). CD8+ Jurkat cells were analyzed by flow cytometry for a decrease in red fluorescence of the cationic dye JC-1, indicating a loss of MMP. Percentage of JC-1 red-negative cells were determined in cultures of CD8+ Jurkat cells after no treatment, 24 hours treatment with MV (10 μg) alone (no IRX) or pre-treated for 24 hours with IRX-2 (1:3 dilution) or MV in combination with the apoptosis-inhibitor Z-VAD-FMK (pan-caspase inhibitor; conc) or ZB4 (anti-Fas neutralizing mAb, conc/dose). Cells treated with 50 μM carbonyl cyanide 3-chlorophenylhydrazone (CCCP), a protonophore that dissipates the H+ gradient across the inner mitochondrial membrane, were used as a positive control. Results are mean±SD of 3 independent experiments (*p<0.005; **p<0.002 compared to sample without IRX-2).

Finally, IRX-2 pre-treatment significantly reduced the MV-induced nuclear DNA fragmentation as detected by TUNEL assay (FIGS. 12A and 12B), representing the final step in the apoptotic process (p<0.0002; FIG. 12B). CD8+ Jurkat cells were either untreated (a), incubated for 24 hours with IRX-2 alone (b) or MV alone for 24 hours (c) or pre-incubated with IRX-2 for 24 hours and subsequently treated with MV for 24 hours (d) and then stained by the TUNEL method to reveal DNA strand breaks (red nuclei) indicative of apoptosis. A minimum of 300 CD8+ Jurkat cells were counted for each treatment group. Results are expressed as the mean percentage±SD of two independent experiments (*p<0.0002 compared to MV-treated sample). This data therefore confirms that IRX-2 exhibits protective effects at each of the relevant steps that culminate in T cell death.

Example 7

IRX-2 Protects T Cells from MV-Induced Down-Regulation of JAK3 and STAT5 Expression It has been previously observed that MV derived from sera of patients with cancer down-regulate expression of molecules mediating the common γ chain cytokine receptor signaling pathway, including JAK3 and STAT5. Since this pathway is essential for the development, maintenance and survival of lymphocytes, and in particular, of CD8+ cells, effects of MV and IRX-2 on JAK3 and STAT5 expression in CD8+ Jurkat cells were next examined.

CD8+ Jurkat cells were untreated or treated with IRX-2 (1:3 dilution) and MV in different combinations. Whole cell lysates of cells from each treatment group were separated on SDS-PAGE and transferred to PVDF membranes for subsequent Western blotting. The expression levels of JAK3, phosphorylated and total STAT5, CD3 and FLIP were analyzed by probing membrane with specific antibodies. Reprobing with β-actin antibody confirmed equal protein loading.

Figure 18:
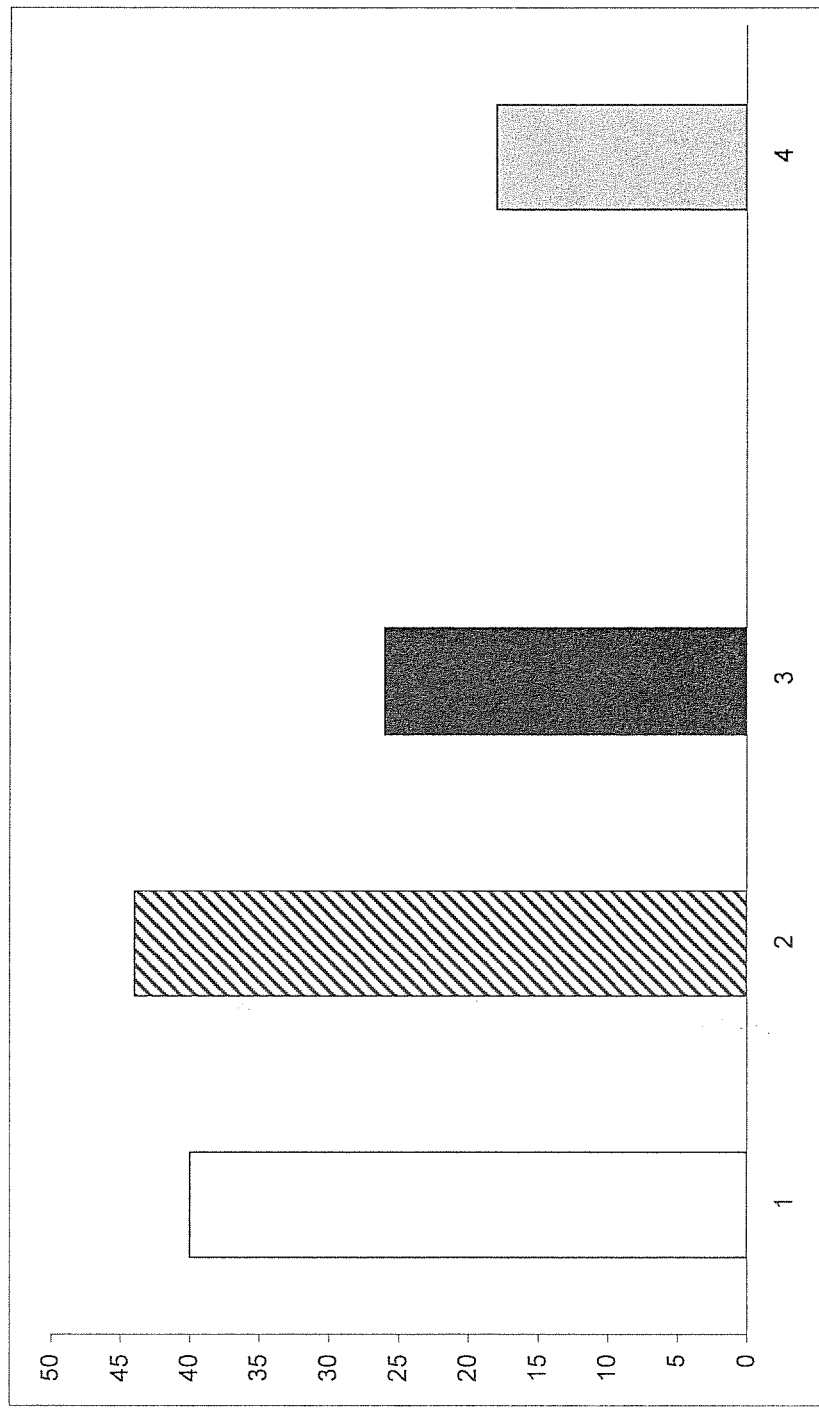
FIG. 18 is a graph of median percentage of lymphocyte infiltration in four groups of patients.

The results shown are representative of 4 experiments performed. As previously observed, MV caused a significant down-regulation of JAK3 in T cells (FIG. 18, panel 1, compare lanes 1 and 3), which intensified with the extended time of co-incubation (FIG. 18, panel 1, lanes 3 and 4). While IRX-2 alone did not increase JAK3 expression (FIG. 18, panel 1, compare lanes 1 and 2), it was able to completely reverse the MV-induced JAK3 down-regulation and restore its expression (FIG. 18, panel 1, compare lanes 3, 4 with lanes 5, 6). Furthermore, IRX-2 caused a strong activation of STAT5, a JAK3 signal transducer, as indicated by phosphorylation of this protein (FIG. 18, panel 2, lane 5). This dramatic activation of STAT5 was sustained even after prolonged (24 hours) incubation with MV (FIG. 18, panel 2, lane 6). Additionally, a loss in CD3-ζ expression in T cells was observed after MV treatment. Here again, pre-incubation with IRX-2 protected T lymphocytes from MV-mediated CD3-ζ down-regulation (FIG. 18, panel 4, compare lanes 3, 4 with lanes 5, 6).

These changes are all consistent with IRX-2 mediating protection from apoptosis via the cytokines present in IRX-2, especially via the primary cytokine IL-2 which is known to signal through the IL-2 receptor and the downstream intracellular signaling molecules Jak3/Stat5. These data elucidate downstream molecular targets of IRX-2 that are central in sending survival and stimulation signals in lymphoid cells.

Example 8

IRX-2 Reverses the MV-Induced Imbalance of Pro- and Anti-Apoptotic Proteins

Figure 14B:
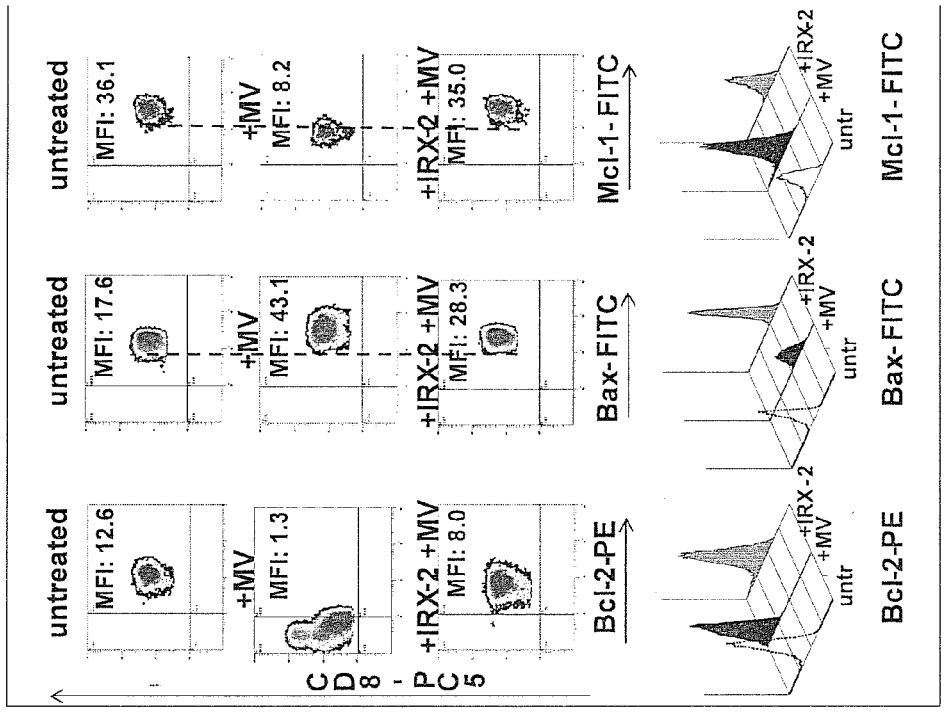
FIG. 14B is a representative dot plot and corresponding histogram showing that IRX-2 treatment modulates the expression of pro- and anti-apoptotic proteins.
Figure 14A:
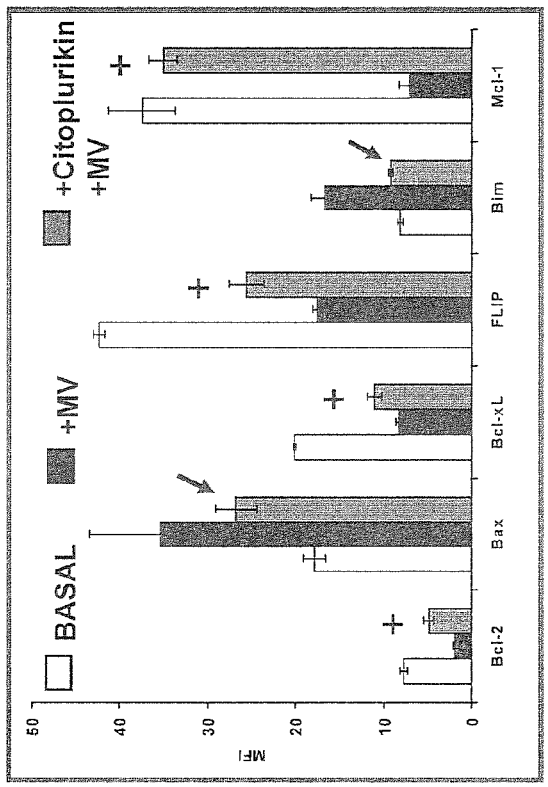
FIG. 14A is a graph showing that pretreatment of cells with IRX-2 reverses the MV-induced changes in the ratios of pro- and anti-apoptotic proteins.

To further examine the mechanisms through which IRX-2 promoted protection of T cells from apoptosis, expression levels of various pro- and anti-apoptotic proteins were measured in activated, MV-treated T lymphocytes and CD8+ Jurkat cells in the presence or absence of IRX-2 by quantitative flow cytometry. Table 3 shows expression levels of several apoptosis-related proteins as mean fluorescence intensity (MFI) in activated CD8+ cells before and after MV treatment. Incubation of T cells with MV caused a significant up-regulation of the pro-apoptotic proteins Bax and Bim, and a concurrent down-regulation of anti-apoptotic Bcl-2, Bcl-xL, FLIP and Mcl-1 (Table 3A). This is consistent with Applicants' previous findings indicating that MV induce apoptosis of T cells. While absolute protein levels are important, it is the ratio of pro-/anti-apoptotic protein levels present in the cell that actually determines cell fate. Thus, changes in these ratios are much more informative of cell state (Table 3B). Dramatic changes of the Bax/Bcl-2, Bax/Bcl-xL and Bim/Mcl-1 ratios upon treatments with MV or IRX-2+ MV were observed. A significant pro-apoptotic shift in these ratios occurred in CD8+ cells upon incubation with MV. In contrast, pre-treatment of T cells with IRX-2 caused a dramatic decrease in these ratios rendering them congruent with those present in untreated cells. (Table 3B), as shown in FIG. 14A. Activated peripheral blood (PB) CD8+ cells were pre-incubated with IRX-2 (at 1:3 dilution) for 24 h and then treated with 10 µg MV for additional 24 h. Expression levels (mean fluorescence intensity) of different pro- and anti-apoptotic protein were measured by quantitative flow cytometry. As shown in FIG. 14B IRX-2 treatment is able to maintain levels of the anti-apoptotic proteins Bcl-2 and Mcl-1 after MV treatment and down regulates expression of the pro-apoptotic protein Bax. MV and IRX-2 had little or no effect on the expression of pro-apoptotic FasL and Bid (data not shown). Similar results were obtained after IRX-2 incubation and MV treatment of activated primary CD4+ cells and CD8+ Jurkat cells.

The balance of pro-versus anti-apoptotic proteins determines whether the cell will complete the apoptotic process resulting in death of the cell. IRX-2 reverses the MV-induced shift toward apoptosis leading to protection from apoptosis. The fact that IRX-2 works to up-regulate core anti-apoptotic proteins such as BCL-2, demonstrates that it is a general inhibitor of apoptosis in lymphoid cells and is beneficial in protecting these cells from a wide variety of tumor derived factors.

TABLE 3

MV and IRX-2 modulate the expression of pro- and anti-apoptotic proteins. The mean fluorescence intensity ± SD (a) and ratios (b) of pro- and anti-apoptotic proteins of MV- and IRX-2-treated activated CD8+ cells[a] are indicated below.

A.

| | | +MV | | +IRX-2 + MV | |
|---|---|---|---|---|---|
| | untreated mean fluorescence intensity ± SD | mean fluorescence intensity ± SD | p value (compared to untreated sample) | mean fluorescence intensity ± SD | p value (compared to MV-treated sample) |
| Bcl-2 | 7.7 ± 0.4 | 1.9 ± 0.1 | 0.0008 | 4.8 ± 0.6 | 0.0049 |
| Bax | 17.9 ± 1.2 | 40.0 ± 1.5 | 0.0001 | 26.8 ± 2.3 | 0.0003 |
| Bcl-xL | 20.1 ± 0.1 | 8.2 ± 0.4 | 0.0001 | 11.0 ± 0.8 | 0.0019 |
| FLIP | 42.4 ± 0.6 | 17.5 ± 0.6 | 0.0002 | 25.5 ± 2.0 | 0.0030 |
| Bim | 8.1 ± 0.3 | 16.7 ± 1.6 | 0.0016 | 9.2 ± 0.3 | 0.0020 |
| Mcl-1 | 37.5 ± 3.8 | 7.1 ± 1.1 | 0.0004 | 35.1 ± 1.6 | 0.0003 |

TABLE 3-continued

MV and IRX-2 modulate the expression of pro- and anti-apoptotic proteins.
The mean fluorescence intensity ± SD (a) and ratios (b) of pro- and anti-apoptotic
proteins of MV- and IRX-2-treated activated CD8+ cells[a] are indicated below.

B.

|  | Bax/Bcl-2 ratio | | Bax/Bcl-xL ratio | | Bim/Mcl-1 ratio | |
| --- | --- | --- | --- | --- | --- | --- |
|  | mean ± SD | p value[b] | mean ± SD | p value[b] | mean ± SD | p value[b] |
| untreated | 2.3 ± 0.6 |  | 0.89 ± 0.3 |  | 0.22 ± 0.3 |  |
| +MV | 18.6 ± 1.2 | 0.0004 | 4.32 ± 0.5 | 0.0001 | 2.35 ± 0.2 | 0.0011 |
| +IRX-2 + MV | 5.58 ± 0.9 | 0.0002 | 2.44 ± 0.4 | 0.0003 | 0.26 ± 0.1 | 0.0009 |

[a]Activated peripheral blood (PB) CD8+ cells were pre-incubated with IRX-2 (at 1:3 dilution; containing ~4 ng/ml or 90 IU/ml IL-2) for 24 hours and then treated with 10 µg MV for additional 24 hours. Expression levels (mean fluorescence intensity) of different pro- and anti-apoptotic protein were measured by quantitative flow cytometry. The data are means ± SD obtained in 3 different experiments.
[b]The p values indicate significant changes in ratios between untreated and MV-treated or IRX-2 + MV-treated cells.

Example 9

The Akt/PI3K-Pathway is the Main Downstream Target of Anti-Apoptotic Activity of IRX-2

The Akt/PI3K signaling pathway is recognized as one of the most critical pathways in regulating cell survival. Since our findings showed a substantial influence of IRX-2 on several key proteins of the Bcl-2-family, which could be regulated by Akt/PKB, we measured the activation of Akt-1/2 in response to MV and/or IRX-2 using an antibody specific for one of the two major regulatory phosphorylation sites, phosphoserine 473. CD8+ Jurkat cells were untreated or treated with IRX-2 and MV (10 µg) in different combinations as indicated. Whole cell lysates of cells from each treatment group were separated on SDS-PAGE and transferred to PVDF membranes for subsequent Western blotting. The activation of Akt-1/-2 was analyzed by immunoblotting with Ser473-specific anti-phospho Akt mAb. Reprobing with a total-Akt antibody confirmed equal protein loading. Results shown are representative from one experiment out of 3 performed.

Figure 15:
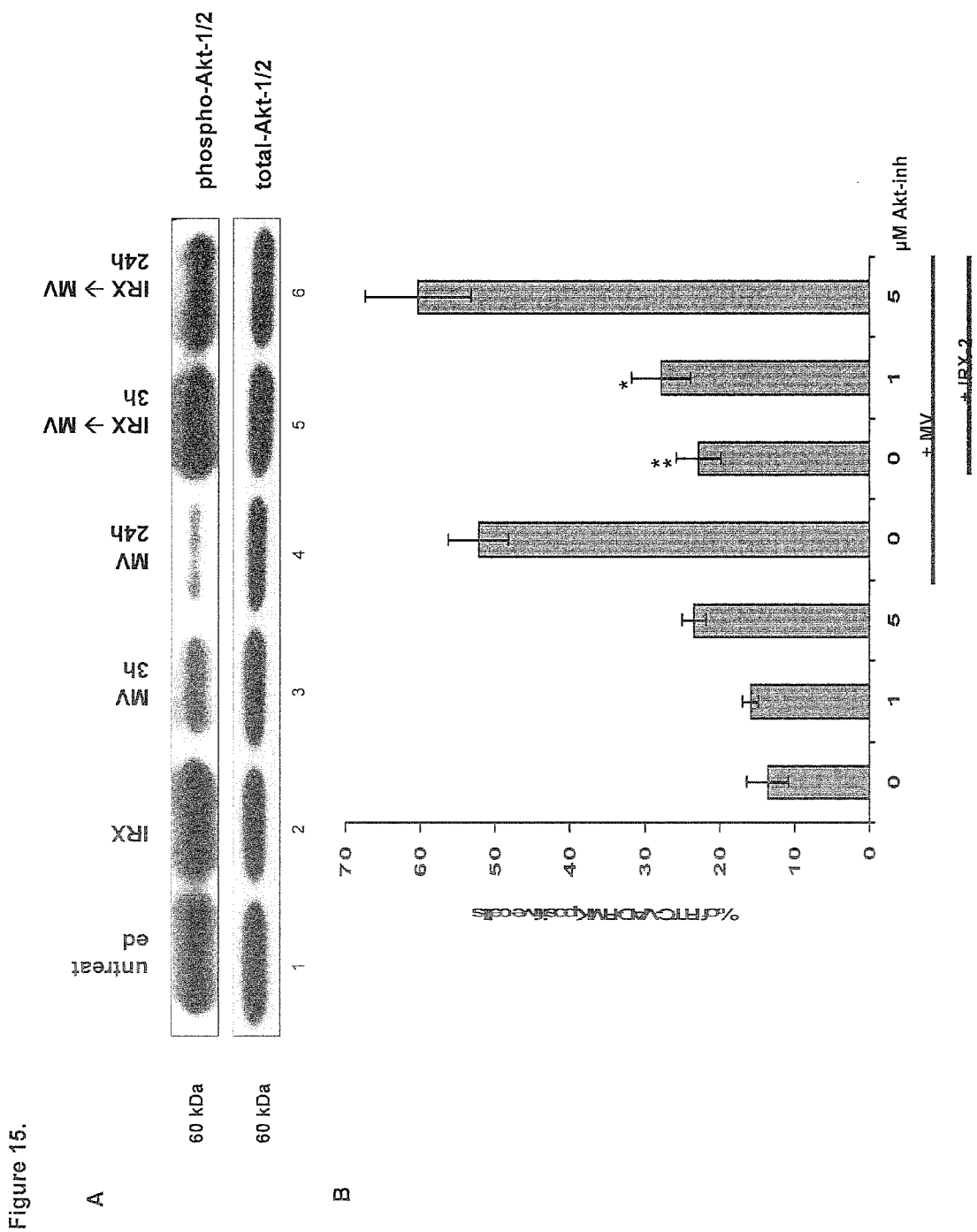
FIG. 15A is a Western blot of CD8+ Jurkat cells with various treatments.
FIG. 15B is a graph of percentage of FITC-VAD-FMK positive cells.
Figure 16:
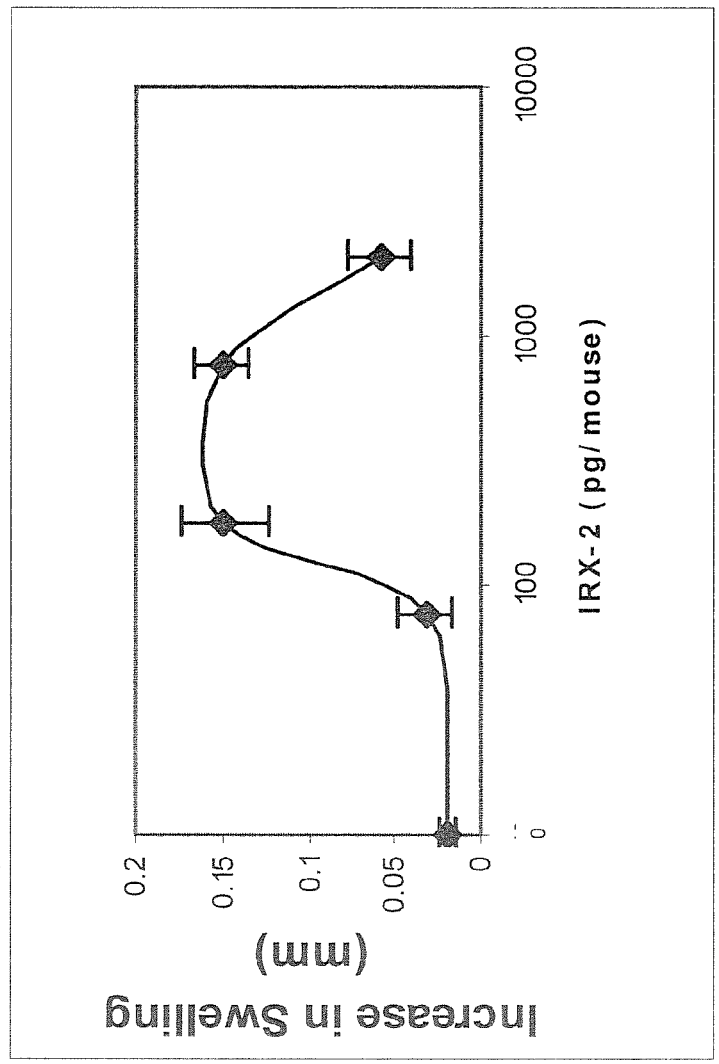
FIG. 16 is a graph of in vivo dose response for IRX-2.
Figure 20:
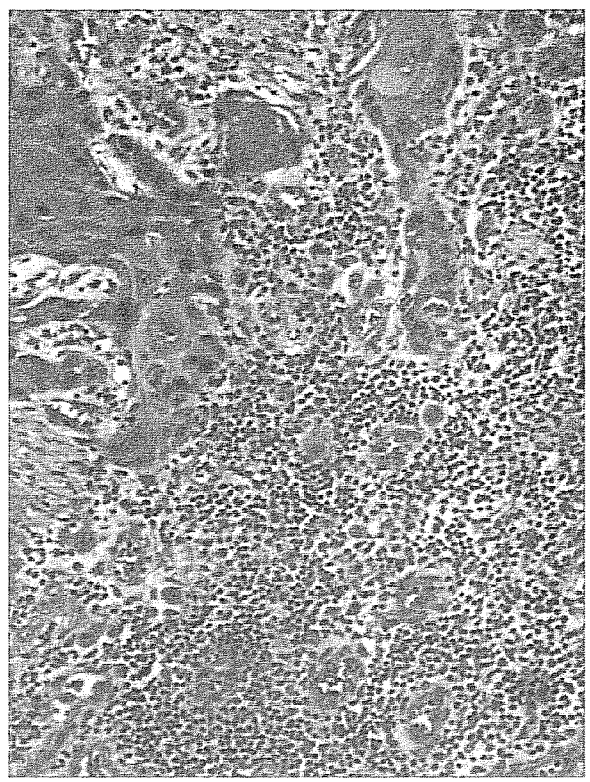
FIG. 20 is a photograph of H&E staining for lymphocyte infiltration.

In untreated CD8+ Jurkat cells (control) Akt-1/2 was constitutively phosphorylated to a level characteristic of Jurkat cells (FIG. 20A, panel 1, lane 1). Pre-incubation with IRX-2 did not enhance basal Akt-phosphorylation (FIG. 15A, panel 1, lane 2). However, when the cells were treated with MV, a dramatic, time-dependent dephosphorylation of Akt-1/2 was observed (FIG. 20A, panel 1, lanes 3 and 4). A time-course study with 10 µg of MV showed that Akt dephosphorylation started at 3 hours of incubation and intensified over time (data not shown). Pre-treatment of Jurkat cells with IRX-2 completely inhibited MV-induced dephosphorylation of Akt-1/2 at both 3 and 24 hours of treatment (FIG. 21S5A, panel 1, lanes 5 and 6).

This pronounced pro-survival effect of IRX-2 on CD8+ Jurkat cells, which clearly counteracted the MV-induced Akt inactivation, indicated that Akt might serve as the main downstream target of IRX-2 signaling. To confirm this hypothesis, CD8+ Jurkat cells were pre-incubated prior to IRX-2 and MV treatment with a small molecule inhibitor specific for Akt, Akti-1/2, and measured the levels of T-cell apoptosis. CD8+ Jurkat cells were pre-incubated with IRX-2 for 24 h or left untreated. Then cells were treated with an Akt inhibitor, Akti-1/2 at different concentrations (0-5 µM) for 1 hour prior to the addition of MV for additional 3 hours. The level of apoptosis was measured by FITC-VAD-FMK staining and flow cytometry analysis. Results are mean percentage±SD obtained in 3 individual experiments (*p<0.05; **p<0.01 compared to MV-treated sample without IRX-2 and Akt inhibitor).

As shown in FIG. 15B, pre-treatment of the cells with the Akt inhibitor resulted in a gradual abrogation of the anti-apoptotic effect of IRX-2. At a relatively low inhibitor-concentration of 1 µM, the protection from apoptosis provided by IRX-2 was only slightly inhibited. However, it was completely blocked at the inhibitor concentration of 5 µM. At these inhibitor concentrations, cell viability was not affected (data not shown). This finding shows that Akt is the main downstream coordinator of the survival signal provided by IRX-2.

Conclusions of Examples 1-9

Confirming previous findings of the Applicants, it was initially showed that incubation of CD8+ Jurkat cells or activated T lymphocytes with MV induced a significant level of apoptosis. Tumor-derived MV expressing a membrane form of FasL were purified from supernatants of the PCI-13 tumor cell line and co-incubated with CD8+ Jurkat cells or activated peripheral blood (PB) T cells. FasL, the Fas ligand, is a type II transmembrane protein belonging to the tumor necrosis factor (TNF) family. FasL-receptor interactions play an important role in the regulation of the immune system and the progression of cancer. Apoptosis is induced upon binding and trimerization of FasL with its receptor (FasR), which spans the membrane of a cell targeted for death. FasL+MV induced not only the extrinsic receptor-mediated apoptotic pathway, but also the intrinsic mitochondrial pathway in activated T cells, with accompanying up-regulation of the pro-apoptotic Bcl-2 family members, Bax and Bim. Pre-incubation of CD8+ Jurkat or activated primary T cells with IRX-2 suppressed both apoptotic pathways in a dose- and time-dependent manner. Further, the pre-treatment of T cells with IRX-2 provided protection not only against MV-induced cell death, but also against CH-11 Ab- and staurosporine-induced apoptosis. Since the former induces apoptosis mainly through the death receptor pathway and the latter activates only the mitochondrial pathway, these findings further show that IRX-2 can protect T-cells from activation of both the extrinsic and the intrinsic death pathways.

Example 10

Figure 21:
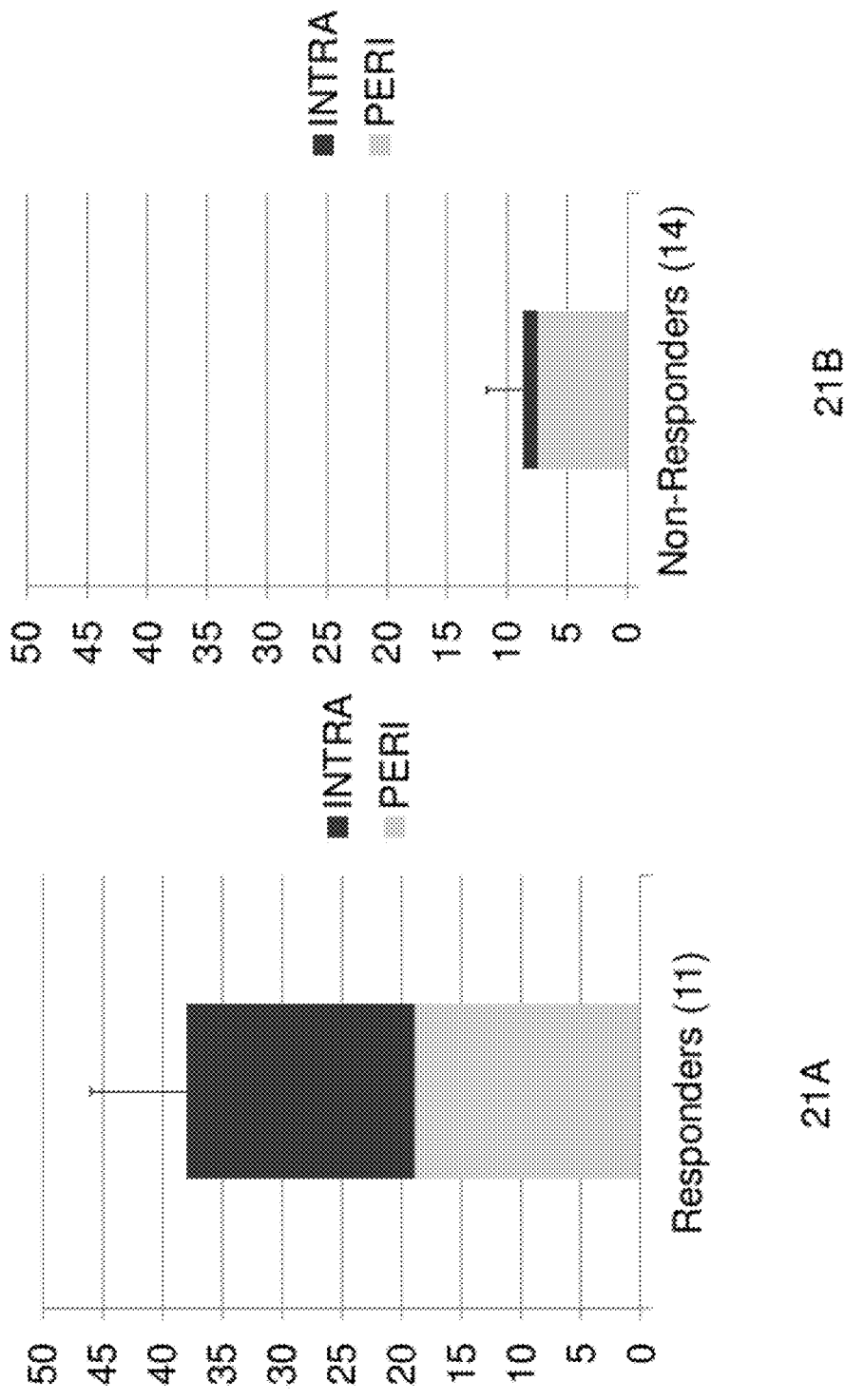
FIG. 21A is a graph of lymphoid infiltration density in responders.
FIG. 21B is a graph of lymphoid infiltration density in non-responders.

The selection of the dose and schedule for the IRX-2 regimen to be used in experiments was based on studies conducted by IRX Therapeutics. The IRX Therapeutics study was performed in mice immunized with prostate specific membrane antigen (PSMA) peptide conjugate and assessed as increase in footpad swelling. FIG. 21 shows these data and the characteristic "bell-shaped" curve.

Figure 17:
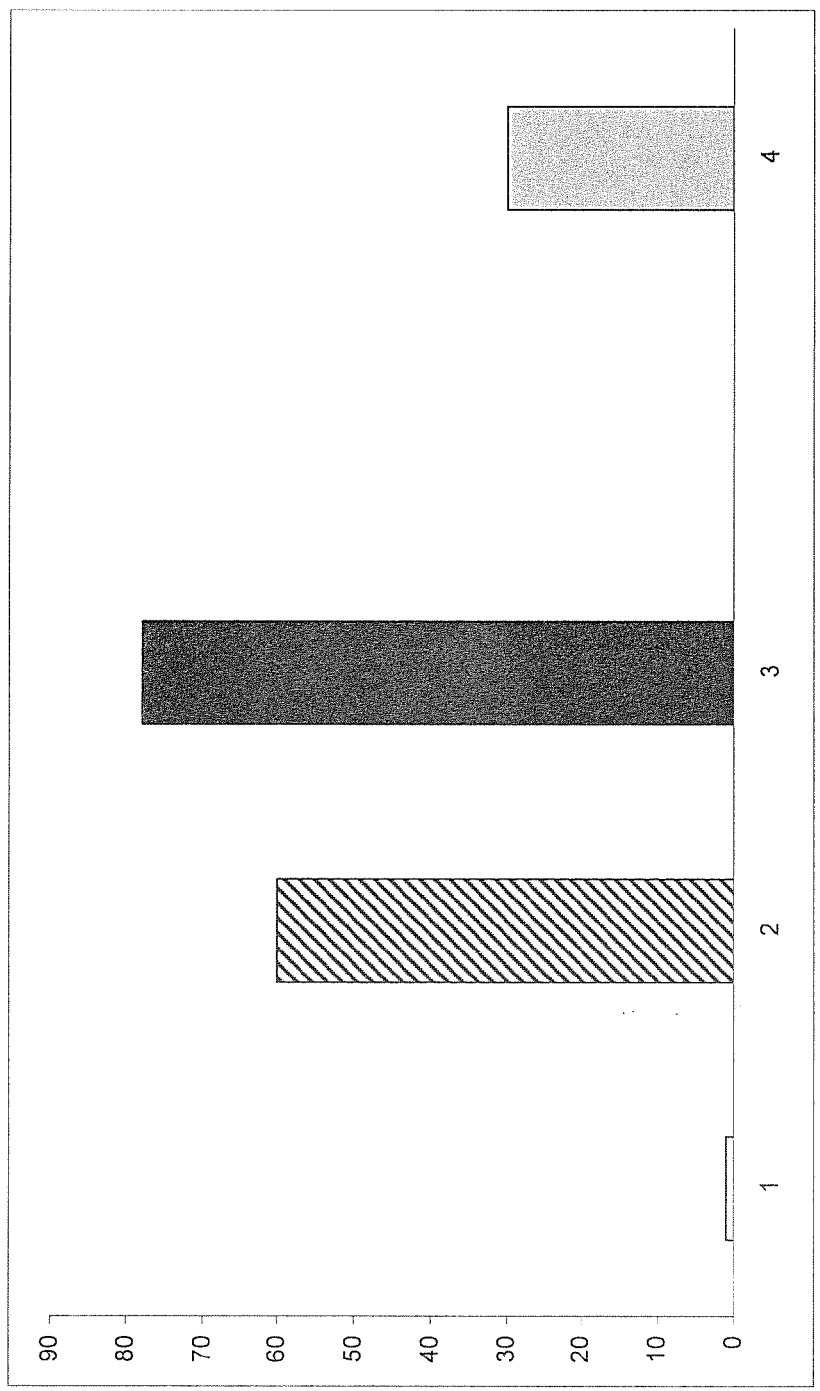
FIG. 17 is a graph of percentage of survival in four groups of patients.

The study was performed in four groups of patients, as shown in Table 4 below. The graph of tumor lymphocyte infiltration and survival for these groups are presented in FIGS. 17 and 18, respectively.

TABLE 4

| Regimen | N | Dose of IRX-2 injection (Units) | Injections/day | # days | Cumulative Dose of IRX-2 (Units) |
|---|---|---|---|---|---|
| 1 | 4 | ~38 U | 1 | 10 | 380 U |
| 2 | 15 | ~115 U | 1 | 10 | 1,150 U |
| 3 | 10 | ~115 U | 2 | 20 | 4,600 U |
| 4 | 6 | ~660 U | 2 | 20 | 26,400 U |

In this study, maximum lymphoid infiltration was achieved for patients treated with the 10 days of 115 U IL-2 equivalence/day. Survival was poor in the four patients who received the lowest dose (regimen 1). Similarly, poorer survival was noted in six patients treated with the highest dose. While survival appeared to be comparable for regimens 2 and 3, regimen 2 patients experienced the most significant histological response as measured by lymphoid infiltration.

The dose of IRX-2 to be studied further was subsequently selected as intermediate between the two most active doses investigated (regimens 2 and 3), a dose clearly adequate to achieve significant histological changes in tumor and lymph nodes. Based upon the additional inconvenience of 20 versus 10 days of treatment and the lesser lymphoid infiltration in the patients who received the higher IRX-2 dose, a 10-day injection protocol with bilateral injection (approximately 2300 U total of IRX-2) was selected for the further studies discussed below.

Example 11

Figure 1:
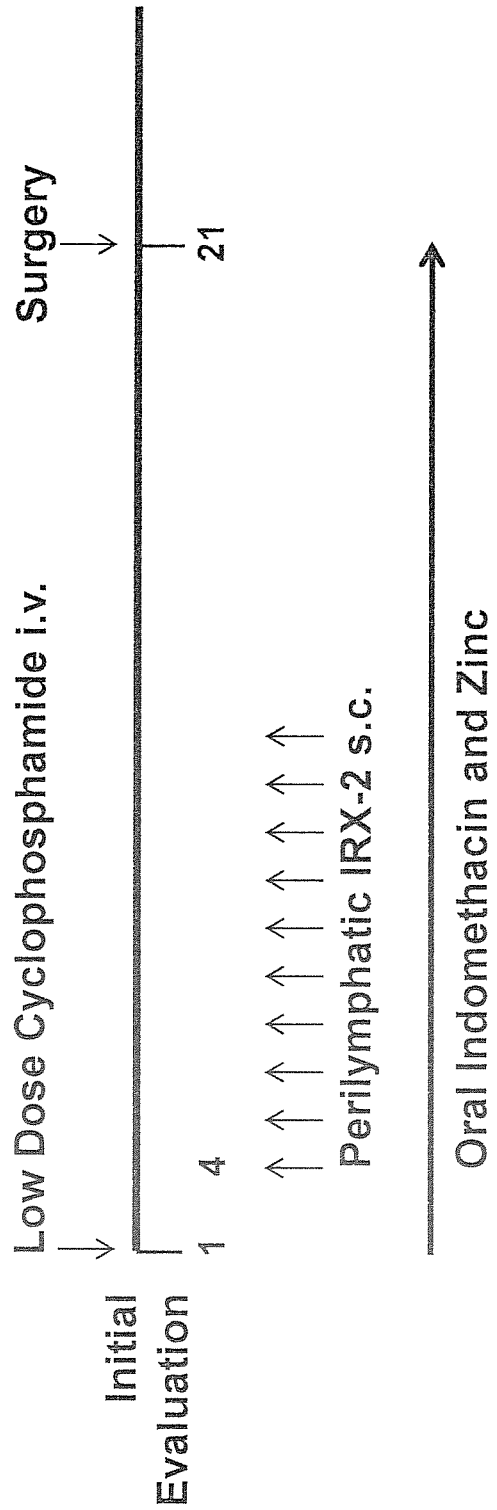
FIG. 1 is a display of the IRX-2 protocol.

A study of the IRX-2 protocol was performed in H&NSCC patients prior to surgery and/or radiotherapy and/or chemoradiotherapy as described in FIG. 1. IRX-2 was administered bilaterally at 115 Units/site. Twenty seven patients were treated; their demographics summarized in Table 5.

TABLE 5

| Number of treated patients | 32 |
|---|---|
| Median age (range) | 66 (34-86) |
| M:F ratio | 25:7 |
| KPS range | 70-100 |
| Patient Characteristics | |
| Oral | 15 |
| Larynx | 13 |
| Other | 4 |
| Stage at Diagnosis | |
| I | 1 |
| II | 5 |
| III | 10 |
| IV | 15 |
| NA | 1 |
| | No. (%) |
| Stage of primary tumor | |
| T1 | 1 (4) |
| T2 | 15 (56) |
| T3 | 6 (22) |

TABLE 5-continued

| T4 | 5 (19) |
|---|---|
| TX | 0 |
| Nodal stage | |
| N0 | 5 (19) |
| N1 | 8 (30) |
| N2 | 14 (52) |
| N3 | 0 |
| NX | 0 |

Radiological studies (CT or MRI) were performed at the onset and prior to surgery and reviewed centrally (Perceptive, Waltham, Mass.). Blood was analyzed centrally (Immunosite, Pittsburgh, Pa.) at onset and prior to surgery for various leukocyte populations (Table 6 and 7). Surgical samples were sent to a central reference laboratory (Phenopath, Seattle, Wash.) for evaluation of the histological changes and performance of immunohistochemistry for various leukocyte markers (Table 8). Appropriate laboratory and clinical measurements were performed to assess toxicology and symptomatic improvement throughout disease-free and overall survival continue to be monitored.

Clinical Results:

Three patients had objective tumor responses (2PR; 1MR). Four patients showed radiological responses (>12.5% reduction); five patients (N2, N2, N1, N1, N1) were down-staged as nodes detected as tumor-positive at the sites and centrally were shown to be negative in the surgical specimens. Four tumors softened (a positive sign), 14 patients had symptomatic improvement/reduced pain and tenderness, improved swallowing, and less bleeding. Treatment related side effects were generally mild (grade I or II) and infrequent including nausea, vomiting, dry mouth, constipation, injection site pain, headache, myalgia, anemia, and contusion. A single example of dyspepsia grade III was observed. Disease-free and overall-survival are being followed. Most patients have cleared one year and survival curves closely parallel those previously observed by Applicants in studies at the National Cancer Institute of Mexico and appear better than case-matched U.S. and Mexican controls.

Example 12

Heparinized blood was collected for immunophenotyping studies to determine numbers of immune cell subsets including B, T, NK, and T naïve, T memory, and T effector cells. Fluorescently tagged monoclonal antibodies to the indicated cell surface markers (or corresponding isotype control) were used to stain fresh, unfractionated whole blood.

The stained and fixed samples were then acquired and analyzed by multi-parameter flow cytometry using a Beckman Coulter FC500 flow cytometer and CXP™ analysis software. Enumeration of absolute T lymphocyte subsets using this single platform (flow cytometry only) method that employs Flow Count™ beads has been demonstrated to be more accurate than dual (hematology instruments and flow cytometry) platform techniques (Reimann et al., 2000). Table 6 below presents a list of the immune markers analyzed by ImmunoSite and their role in an immunization.

TABLE 6

Immune Markers Analyzed & Role in Immune Response

| Cell | Marker | Role |
|---|---|---|
| T cell | CD3 | Mediates cellular immunity |
| B cell | CD3− CD19+ CD14− | Mediates humoral immunity |

TABLE 6-continued

Immune Markers Analyzed & Role in Immune Response

| Cell | Marker | Role |
|---|---|---|
| Helper T cell | CD3+ CD4 | Makes cytokines, provides B cells "help" |
| Cytotoxic T cell | CD3+ CD8 | Kills tumor cells |
| Naïve T cell ($T_N$) | CD3+ CD45RA+ CCR7+ | Antigen naïve or very early post-primary stimulation; lymph node homing ability |
| Central Memory T cell ($T_{CM}$) | CD3+ CD45RA− CCR7+ | Long-lived memory cell, low effector function; homes to lymph nodes |
| Effector Memory T cell ($T_{EM}$) | CD3+ CD45RA− CCR7− | Intermediate effector function; shorter half-life in vivo; seeds tissues/tumors over lymph nodes |
| Effector T cell ($T_{EMRA}$) | CD3+ CD45RA+ CCR7− | Highest effector function (e.g. cytolysis); localizes best to tissues/tumor |

For the purposes of the present invention, only the cell populations directly relevant to evaluating the hypothesis of whether an immunization occurred or not are discussed herein.

The developmental pathways for T lymphocytes, especially CD8+ T cells, have been intensively studied over the last decade with a particular focus on CD8+ T cells since they are most closely associated with effective anti-tumor immunity. Both CD4+ helper T cells and CD8+ cytotoxic T cells can be subdivided into reciprocal CD45RA+ and CD45RO+ subpopulations. CD45RA+ cells have previously been termed naïve T cells; however, more recent work indicates that these T cells in blood comprise naïve T cells as well as more fully differentiated effectors often termed $T_{EMRA}$ (Lanzavecchia, 2005; Kaech, 2002). CD45RO+ (CD45RA−) memory T cells can also be subdivided into T central memory ($T_{CM}$) and T effector memory ($T_{EM}$). These sub-classifications are based upon surface expression of additional markers including CCR7 (Sallusto, 1999; Tomiyama, 2004). The developmental pathways of these various T cell subsets and their lineage relationships remain complex. The data and tests for significance are presented in Table 7 below.

Consistent with the hypothesis that IRX-2 acts on both T cells and DC's to foster activation, maturation, and enhance endogenous tumor antigen presentation to naïve T cells, it was observed that the naïve T cell population (CD3+ CD45RA+ CCR7+) decreased between baseline and Day 21. Naïve T cells are initially activated by recognition of antigen when presented on the appropriate major histocompatibility complex (MCH) molecules by mature DC's. The subsequent steps of generating T cell memory and full effector function are not perfectly defined, but it is clear that different subpopulations of T cells as defined by several markers, i.e. CD45RA/RO and CCR7 have distinct functional properties. For example, CCR7 expression confers the ability of the T cell to home to lymph nodes where the most effective anti-tumor priming occurs.

A significant decline was observed in the naïve T cell population (CD3+ CD45RA+ CCR7+) with population levels of 55.6 cells/mL$^3$ at baseline falling to 17.4 cells/mL$^3$ at Day 21 (p=0.02). A loss of naïve T cells results from those cells finding and being stimulated by their respective cognate antigen and the differentiating into an alternative functional population, either of the two memory or full effector populations.

In addition, the central memory T cell population (CD3+ CD45RA− CCR7+) with the CCR7+ conferred lymph node homing propensity, fell from 56.9 cells/mL$^3$ at baseline to 34.1 cells/mL$^3$ at Day 21 (p=0.028). This too is an indicator that immunization to tumor antigens is taking place in response to IRX-2 therapy. Studies show that the $T_{CM}$ population of T cells represents the earlier, more "stem-like" memory population that upon re-stimulation, preferentially homes to the lymph node where it can gain more effector, e.g. cytolytic function. The significant decline seen in this population is consistent with these $T_{CM}$ cells exiting the bloodstream and migrating to the draining lymph nodes where they will be further activated.

After an immunization, one would expect other immune cells to be enlisted in the attack on the antigen-bearing offender. Further support to the immunization hypothesis was observed in that a significant drop (p<0.01) in B cells was observed. B cells are recruited into lymph nodes where they

TABLE 7

Summary of Immunology Assessments & Tests of Significance

| Cell population | N | Mean cells/mL$^3$ | Std Dev | Baseline to Day 21 Difference | Std Dev | Degrees of Freedom | T value | P value |
|---|---|---|---|---|---|---|---|---|
| Baseline | | | | | | | | |
| Lymphocyte Gate | 25 | 1177.5 | 442.4 | −69.6 | 260.7 | 24 | −1.33 | 0.1946 |
| B cell | 18 | 275.4 | 132.2 | −74.3 | 74.8 | 17 | −4.22 | 0.0006 |
| Helper T cell | 25 | 817.0 | 330.7 | −65.4 | 184.0 | 24 | −1.78 | 0.0884 |
| Cytotoxic T cell | 25 | 351.9 | 193.3 | −4.4 | 87.9 | 24 | −0.25 | 0.8061 |
| Naïve T cell | 25 | 55.6 | 89.8 | −38.2 | 76.9 | 24 | −2.49 | 0.0203 |
| Central Memory T cell | 25 | 56.9 | 84.5 | −22.8 | 48.6 | 24 | −2.34 | 0.0280 |
| Effector Memory T cell | 25 | 689.0 | 354.7 | 41.2 | 223.4 | 24 | 0.92 | 0.3651 |
| Effector Memory RA T cell | 25 | 395.0 | 250.2 | −35.2 | 132.7 | 24 | −1.33 | 0.1968 | are exposed to antigen and then exit to be found in the tumor where they presumably produce antibodies capable of attacking the tumor directly or supporting antibody-dependent cellular cytotoxicity (ADCC).

The statistically significant changes and trends observed herein strongly show that an immunization of naïve T cells is occurring due to IRX-2 administration. As no other primary interventions were observed in these patients, it is unlikely that these changes occurred at random.

The hypothesis that IRX-2 treatment induces immunization to autologous tumor antigens is also supported by Applicants' published information on H&NSCC lymph node response following IRX-2 treatment as compared to non-randomized normal and H&NSCC control patients (Meneses, 2003). The salient lymph node response features associated with IRX-2 treatment were nodal replenishment and lymphocyte expansion, particularly T lymphocytes, which were shown to be depleted in the lymph nodes of untreated H&NSCC patients (Verastegui, 2002). Nodal expansion that occurs during an immunization presumably due to IRX-2 was also observed to be associated with a reversal of sinus histiocytosis, an apparent dendritic cell functional defect. These changes are consistent with an immunization. A prior study confirms that immunization to tumor antigen occurs at the level of the regional lymph node, not the tumor itself (Maass, 1995).

Histology

When an immunization occurs in lymph nodes, the new killer memory T cells are thought to develop and then exit the nodes through blood vessels, and flow into tissues to patrol for the antigenic target (i.e. the immune target). If the antigenic target is identified, the killer memory T cell will infiltrate the tissue to kill the target. When a cellular immune response is initiated, other immune cells are recruited to participate in the kill and clean-up process.

T lymphocyte infiltration into tumors, particularly of CD45RO+ CD8+ T cells, is evidence of an immunization to tumor antigens and that such infiltration correlates with improved survival in a variety of cancers including H&NSCC, melanoma, colorectal, and ovarian (Wolf, 1986; Pages, 2005; Galon, 2006.

It was hypothesized herein that an IRX-2 induced immunization in lymph nodes would result in lymphocytic infiltrate in the tumor and tumor disruption and the presence of specific immune cells in the tumor would provide evidence of an anti-tumor immune response. It was also hypothesized that an immune response to the tumor would be evidenced by diffuse lymphocytic infiltrate, spanning the tumor's peripheral area to its intratumoral area.

Formalin fixed paraffin embedded blocks or unstained slides from primary tumor biopsy and resection specimens were submitted by the clinical sites to PhenoPath Laboratories (Seattle, Wash.) for hematoxylin and eosin ("H&E") and immunohistochemistry staining ("IHC"). Paired samples from 26 IRX-2 study subjects were submitted, 25 were evaluable, and one surgical specimen had no histological evidence of tumor. Two ad-hoc comparator groups of surgical specimens were collected at the end of the study for H&E comparison: 25 surgical specimens from MD Anderson, and 10 surgical specimens from Stony Brook Health Sciences Center, randomly selected from untreated H&NSCC surgical specimens.

Immunohistochemistry staining was performed only on the IRX-2 treated samples to determine the presence of immune markers in the tumor. Their markers are listed in Table 8.

TABLE 8

Immune Markers Analyzed by IHC

| Cell | Marker | Role in Immune Response |
|---|---|---|
| T cell | CD3 | Mediate cellular immunity |
| B cell | CD20 | Produce antibody |
| Helper T cell | CD4 | Make cytokines; help B cells |
| Cytotoxic T cell | CD8 | Kill tumor |
| Plasma cell | CD138 | Produce antibody |
| Macrophage | CD68 | Assist T cell and kill tumor |
| Naïve/Effector T cell | CD45RA+ | Naïve/Effector T cell |
| Memory T cell | CD45RO (RA−) | Antigen committed T cell |

The presence of IHC stained markers was evaluated under low power and graded using a prospectively defined 0-100 mm visual analog scale (VAS), where 0 represented 0% presence and 100 represented 100% of cells staining positive for the marker. The peroxidase reaction used to highlight the marker overestimates the area or density of lymphocyte infiltration as compared to H&E staining, thus making IHC-based density determinations unreliable, but IHC remains useful for elucidating the relative relationships between and among cell types.

H&S Studies: Methods and Analyses

Three analyses were performed comparing the H&E stained slides. Two analyses were blinded feature extractions from the 25 IRX-2 treated and 25 untreated surgical specimens from MD Anderson, one for tumor features and one for immune response features. The third analysis was an identical but unblended immune response feature extraction from the 10 H&E stained slides from Stony Brook. In each case, features were extracted and quantified using a VAS on case report forms.

Two assessments were made for each of the immune response features, the first assessment was the overall presence of the marker across the entire surgical specimen and the second was to the degree to which the location of the infiltrate was peripheral or intratumoral.

Figure 19:
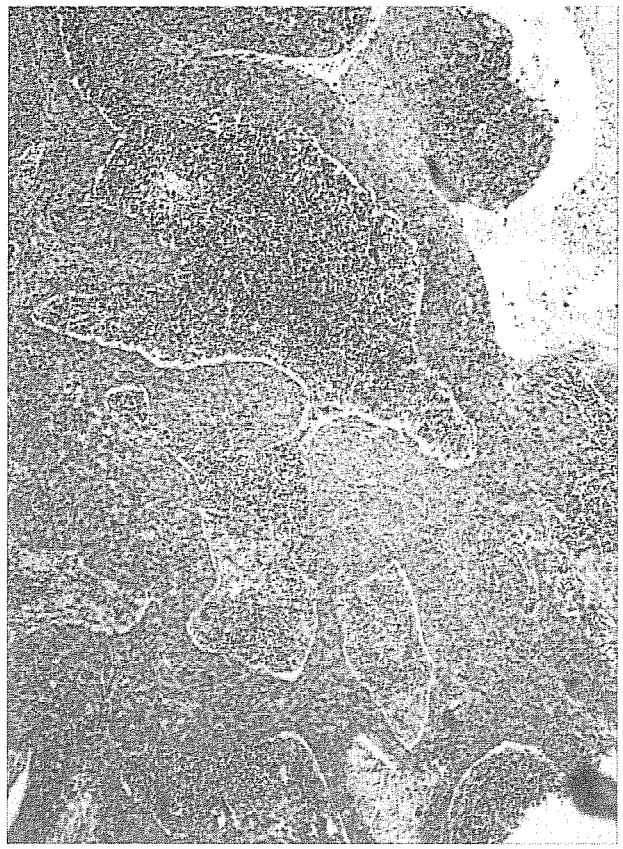
FIG. 19 is a photograph of H&E staining for lymphocytes.

An overall assessment was made taking into account: lymphocyte infiltration, its density, its balance between tumor and infiltration, and other features that comprise the gestalt impression of the tumor. The other sub-features include the extent of fibrosis and necrosis, suggesting where tumor was but is no longer and in the case of well differentiated squamous cell cancer, a concentration of keratin pearls with minimal or not tumor surrounding it is another sign of tumor destruction. An "Active Immunologic Response" includes lymphoid infiltration evidence of damage created by the immune system, and the degree to which tumor is no longer viable and disrupted—in short the extent and process by which the host is combating the tumor. An example of the lymphocyte infiltration sub-feature of the "Active Immune Response" is presented in FIGS. 19 and 20.

One of the dominant sub-features on the Active Immune Response variable is the localization and intensity of the lymphocyte infiltration (LI) that are observed in patients treated with IRX-2. Surgical specimens demonstrating this reaction in both IRX-2-treated patients and the ad-hoc comparator groups demonstrated marked increases in the density of overall LI, peritumoral LI, and intratumoral LI.

Based on the pre-specified critical point of 50 mm or greater on the VAS, the analysis showed different Active Immunologic Response rates among the three groups of surgical specimens as showed in Table 9 below.

TABLE 9

| Group | Patient w/AIR | Total Patients | Active Immune Response Rate |
|---|---|---|---|
| 1. IRX-2 Treated | 11 | 25 | 44.0% |
| 2. MD Anderson | 6 | 1 | 24.0% |
| 3. Stony Brook | 1 | 10 | 10.0% |

The increase in the frequency of those patients demonstrating an Active Immune Response went from 20% in the pooled MD Anderson and Stony Brook groups to 44% in the IRX-2 treated group (p<0.05 by Chi square test).

Determination of Peritumoral vs. Intratumoral LI

The location of immune cells in the tumor was also evaluated. It was hypothesized herein that an active anti-tumor immune response would include lymphycytic infiltrate that expanded from the peripheral area to include the intratumoral area.

Based upon the VAS analysis for Active Immune Response in the IRX-treated patients, 11 showed intense reactions (≥50, termed responders) and 14 showed less intense reactions (<50, termed non-responders). A comparison of the LI of these two groups is shown in FIGS. 21A and 21B.

As can be seen, the responders showed a marked increase in LI (both area and density) of the typical section and compared to the non-responders, the increase in intratumoral LI is proportionally much greater than the peritumoral change.

Figure 22:
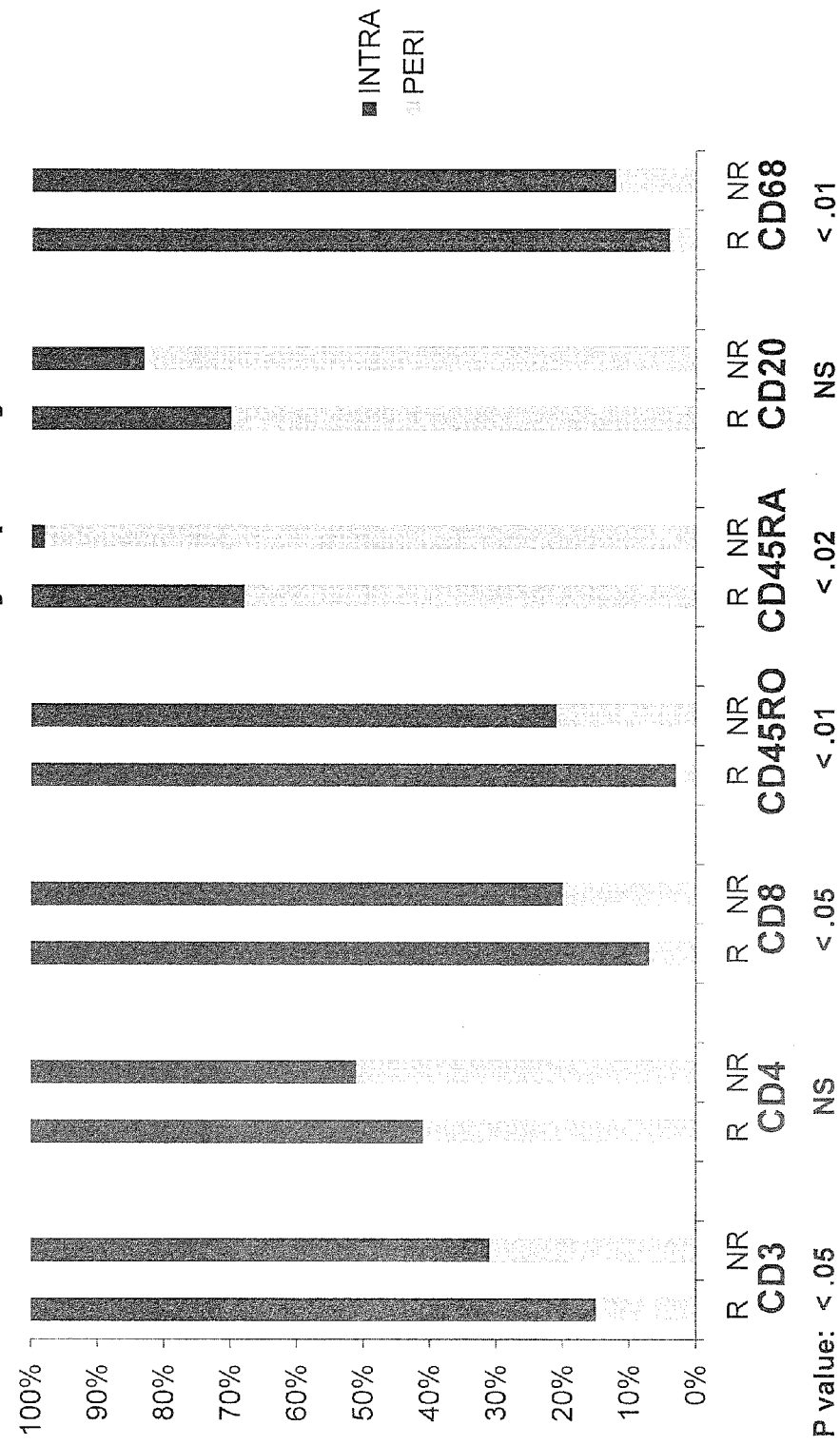
FIG. 22 is a graph of location of intratumoral/peritumoral lymphocyte infiltrates.
Figure 23:
FIG. 23 is a photograph of IHC staining for CD45RO+ memory T cells.

Immunohistochemistry for the location of various markers helps clarify which cells dominate in each region. FIG. 22 shows these results. The peritumoral infiltrate, representing approximately 25% of the LI in the specimen was dominated by CD45RA+, CD3+, CD4+ T lymphocytes and CD20+ B lymphocytes. Whereas the intratumoral infiltrate, representing approximately 75% of the LI in the specimen, was dominated by CD45RO+, CD3+ and CD8+ lymphocytes (i.e. the "killer" effector T cell phenotype) and CD68+ macrophages. FIG. 23 provides a pictoral example of IHC staining fro CD45RO+ memory T cells in an IRX-2 treated surgical specimen. TABLE 10 shows the results of each cell population's presence in the tumor.

TABLE 10

| | | Presence in the Tumor* | |
|---|---|---|---|
| Cell Population | N | Overall Mean | Intratumoral Mean |
| T cell (CD3) | 24 | 52.3 | 76.5 |
| B cell (CD20) | 24 | 11.0 | 21.2 |
| Helper T cell (CD4) | 24 | 15.5 | 53.1 |
| Cytotoxic T cell (CD8) | 24 | 37.8 | 85.7 |
| Macrophage (CD68) | 24 | 42.1 | 91.5 |
| Effector T cell (CD45 RA) | 24 | 7.4 | 18.4 |
| Memory T cell (CD45 RO) | 24 | 65.4 | 87.3 |

*Measurements based on 100 mm Visual Analog Scale (VAS) assessments

The strongest support for this immunization hypothesis derives from the examination of lymphocyte infiltration for infiltration in and around the tumor and the picture of tumor rejection indicating necrosis, fibrosis, and reduced tumor. The rejection patterns are characteristic for both humoral and cellular immunity with increased B lymphocytes and activated macrophages within the tumor, respectively. By shifting the balance back to immunosurveillance by overcoming the immune suppression seen in cancer patients and restoring immune function, IRX-2 therapy causes the host to reject the tumor and immunize itself against the tumor leading to reduced recurrence and increased survival.

Example 13

Figure 24:
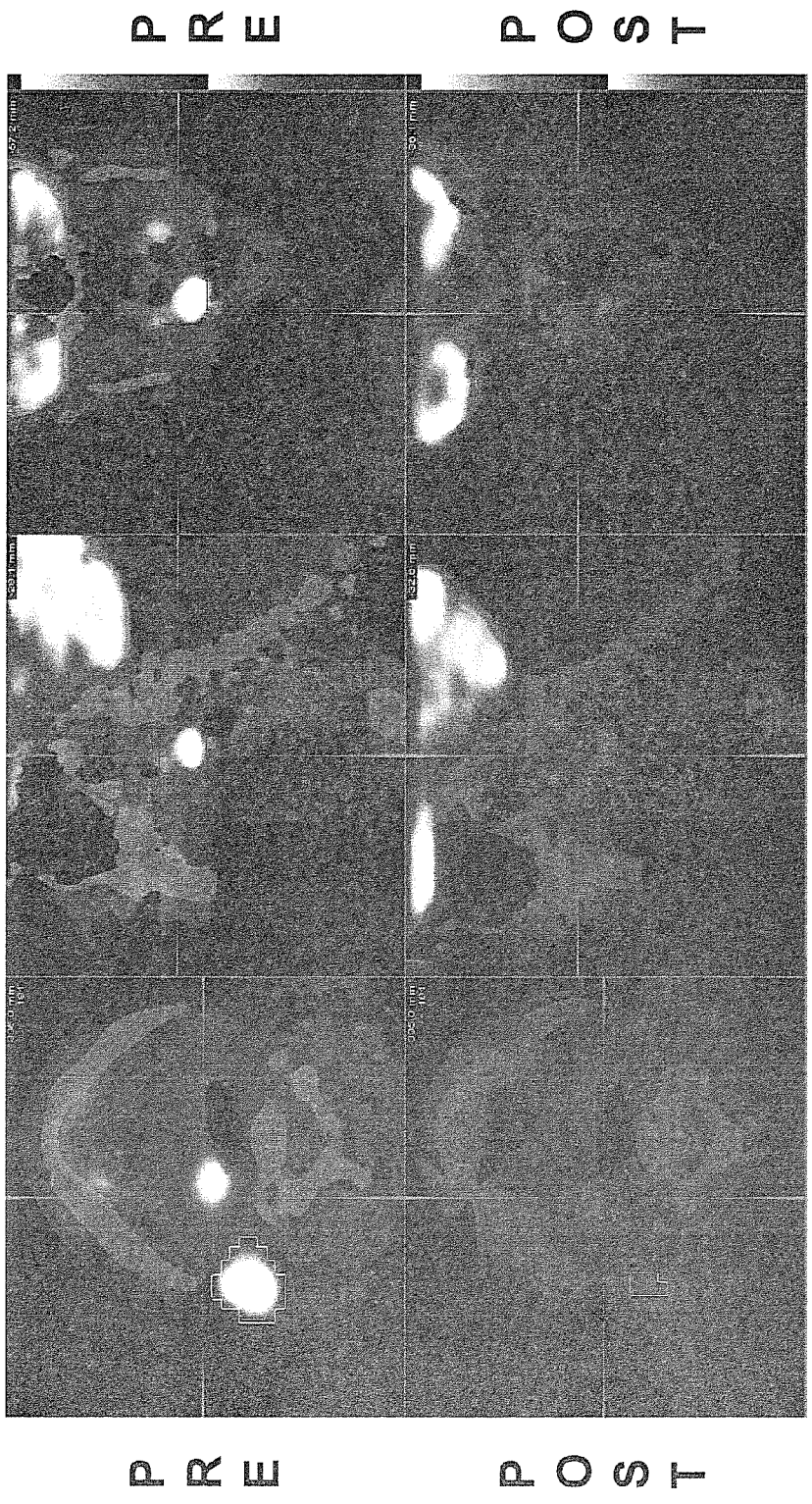
FIG. 24 is a photograph of fused FDG PET/CT scan images at day 0 and day 21.

In one patient, fused FDG PET/CT scans were compared at day 0 and day 21, as shown in FIG. 24. Total glycolitic activity and volume were measured and are shown in Table 11.

TABLE 11

| | Baseline | Day 21 | % Change |
|---|---|---|---|
| | Total Glycolytic Activity | | |
| Tumor | 68.91 | 31.36 | −54.49% |
| Node 1 | 72.54 | 4.97 | −93.15% |
| Node 2 | 14.35 | 3.15 | −78.05% |
| | 155.80 | 39.48 | −74.66% |
| | Volume | | |
| Tumor | 12.16 | 7.33 | −39.72% |
| Node 1 | 9.46 | 1.44 | −84.78% |
| Node 2 | 2.28 | 1.24 | −45.61% |
| | 23.90 | 10.01 | −58.12% |

Example 14

Figure 25:
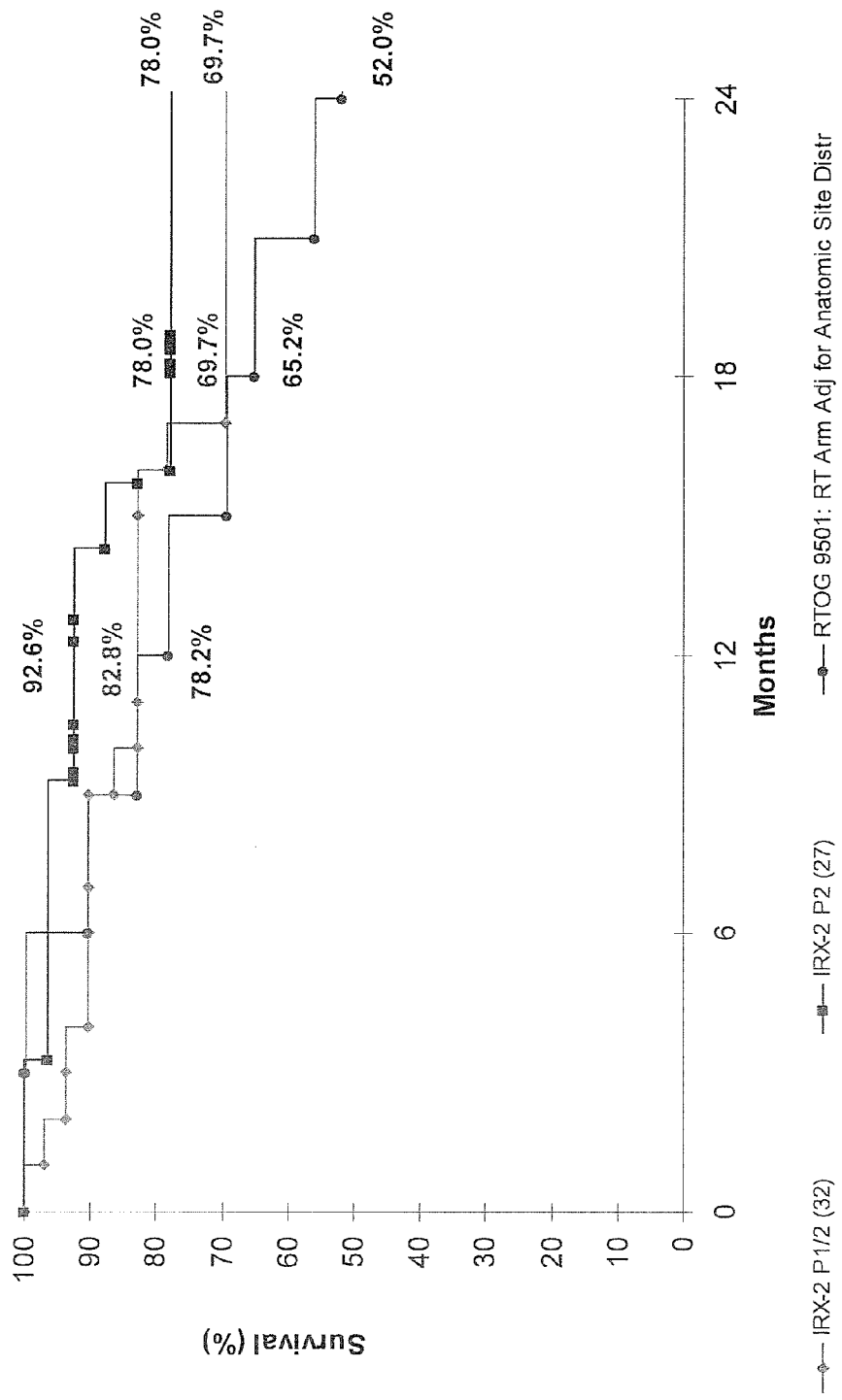
FIG. 25 is a graph showing Kaplan Meir plots of overall survival.
Figure 26:
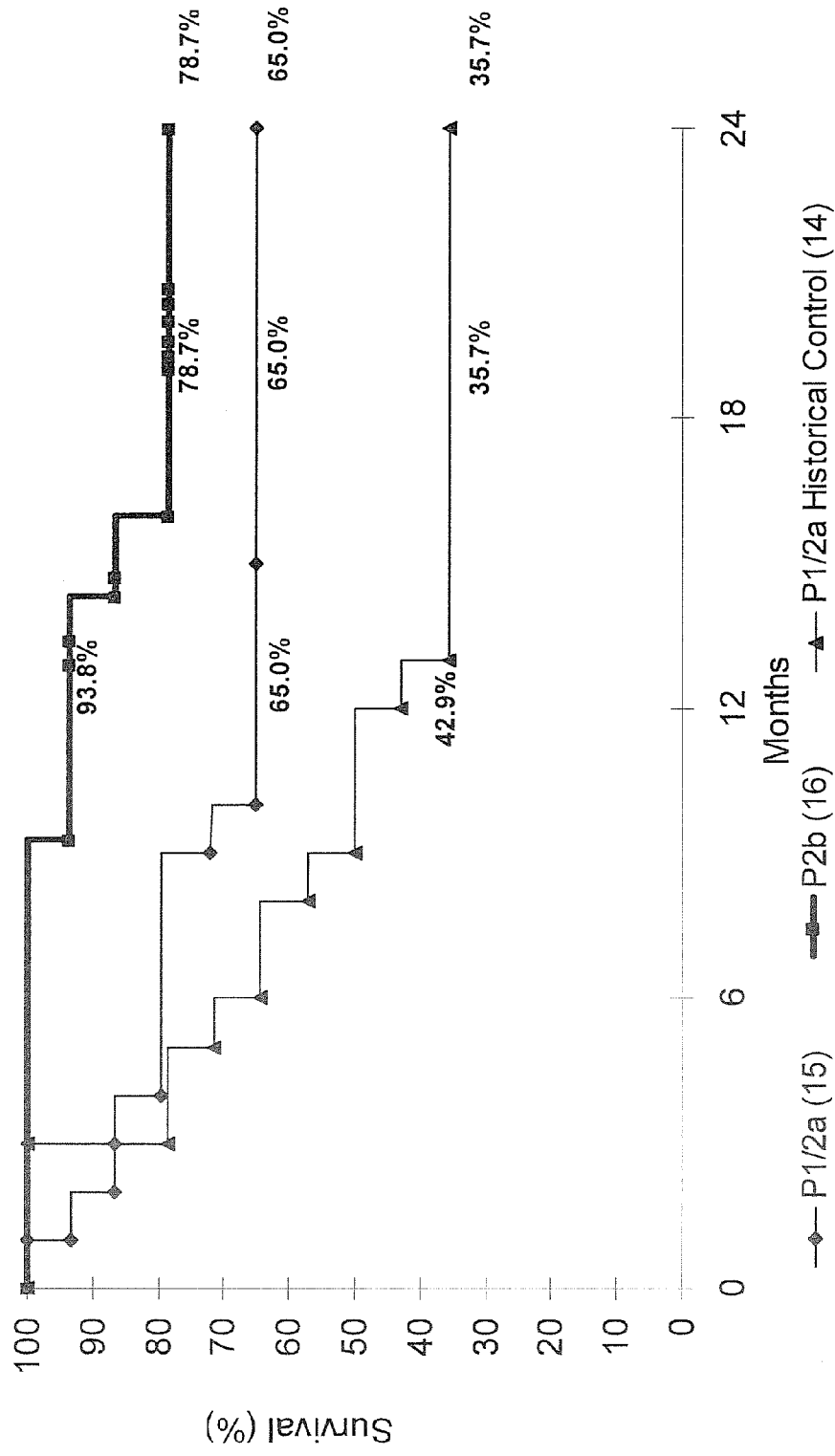
FIG. 26 is a graph of overall survival for Stage IVa patients.

Overall survival was determined both for patients overall (FIG. 25) and for patients in Stage IVa (FIG. 26). FIG. 25 shows three Kaplan Meir plots of overall survival. The top line is the recently completed multicenter Phase 2 study (median follow-up of 18.6 months), the middle line is the single center Phase 1/2 study completed 10 years ago and as compared to the best available comparator—the randomized site matched RTOG 9501 trial. In both IRX-2 treated groups, survival is above the anatomic site-matched RTOG 9501 trial data. The data suggests that the IRX-2 driven immunization is durable and leads to improved survival. FIG. 26 shows the three Kaplan Meier plots of overall survival the Stage Iva cohort. The top line is the recently completed multicenter Phase 2 study (median follow-up of 18.6 months), the middle line is the single center Phase 1/2 study completed 10 years ago and as compared to the best available comparator—the randomized site matched RTOG 9501 trial. In both IRX-2 treated groups, survival is above the anatomic site-matched RTOG 9501 trial data. The data suggests that the IRX-2 driven immunization is durable and leads to improved survival in Stage IVa patients.

Example 15

Figure 27:
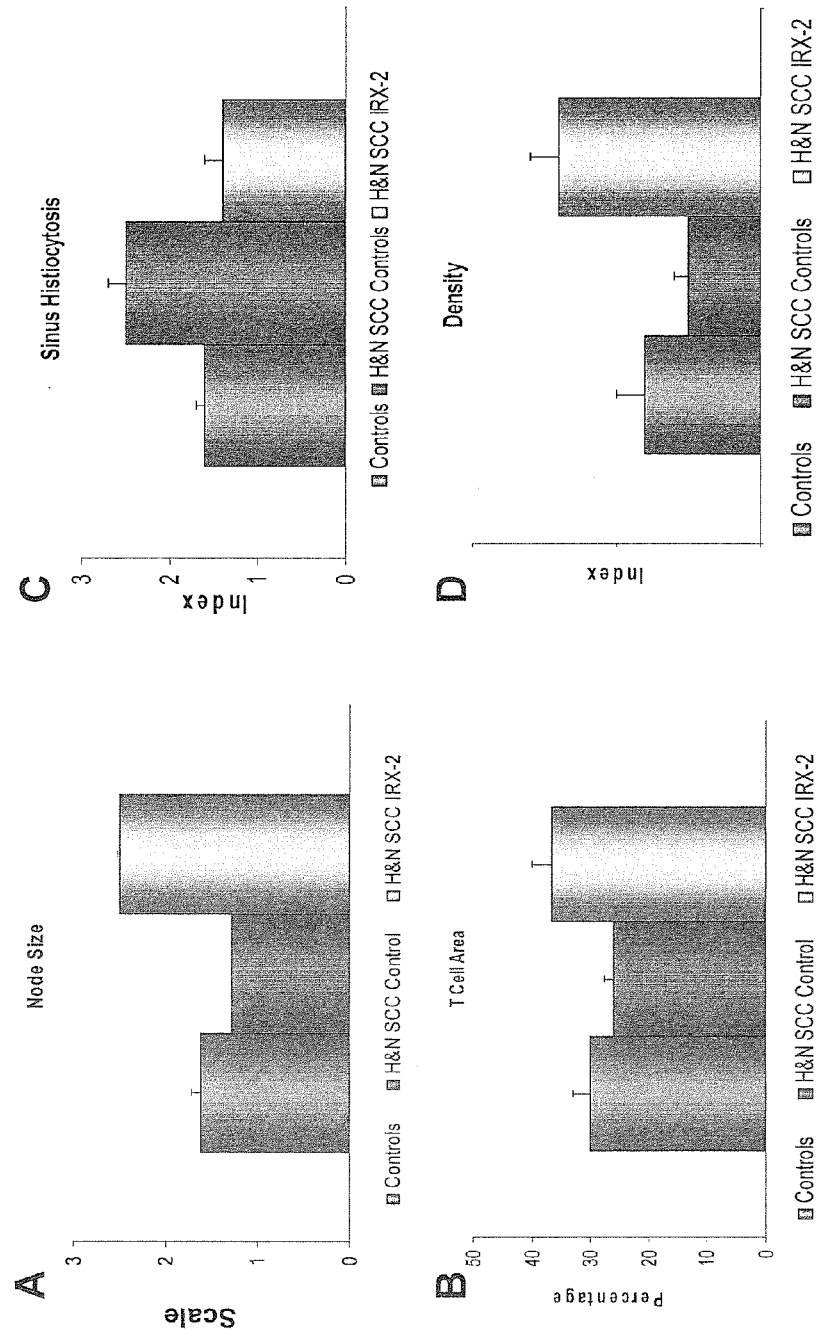
FIG. 27A is a graph of node size.
FIG. 27B is a graph of T cell area.
FIG. 27C is a graph of sinus histiocytosis.
FIG. 27D is a graph of T cell density as compared in controls, H&NSCC controls, and H&NSCC patients administered IRX-2.

IRX-2 was shown to increase regional lymph node size, T cell area and density, and reverse sinus histiocytosis. Controls, H&NSCC controls, and H&NSCC patients administered IRX-2 are compared in FIGS. 27A-D. Twenty patients from a total of 50 with H&N SCC treated with the IRX-2 protocol were selected as having uninvolved regional lymph nodes suitable for evaluation. All displayed clinical responses, either partial responses (PR, >50% tumor reduction) or minor responses (MR, <50%>25% tumor reduction). Complete responders (3/50) and non-responders (5/50) were excluded for obvious reasons. Ten untreated H&N SCC control LN specimens were selected randomly as one control group (H&N SCC control) and 10 non-cancer control LN biopsies were selected randomly (control group). Obvious LN pathologies were excluded from the control group. Overall, 95% of the IRX-2 LN, 80% of the noncancer controls, and 60% of the H&N SCC controls were adjudged to be stimulated Overall, the LN of IRX-2-treated patients showed a high percentage of stimulation with a shift toward T cell reactivity. The mean size of the LN of H&N SCC controls was significantly smaller than the control group and those of the IRX-2-treated H&N SCC patients were significantly larger than both cancer and non-cancer control p's <0.01) (FIG. 27A). The non-T and B cell "other cell" LN area by subtraction and by PAS staining was approximately 25% of the total and corresponded mostly to the degree of sinus histiocytosis (FIG. 5). It is of note that sinus histiocytosis was marked in the H&N SCC control but not in the other groups. In 9 of the 10 H&N SCC controls, but in none of the other cases, sinus congestion with erythrocytes was also observed; however, erythrophagocytosis by the his-lymphocytes, either B and PC or T lymphocytes, were calculated and correlated with the area of the lymph node bearing the corresponding lymphoid populations. (FIG. 27C. The T cell area of H&N SCC controls was modestly reduced (p=NS) and the density significantly reduced (p<0.01), compared to non-cancer controls (FIG. 27B). T cell area of IRX-2-treated patients was modestly increased compared to non-cancer controls (p=NS) and significantly so over the H&N SCC controls (p<0.01). T cell density of the IRX-2-treatedLN was significantly greater than both controls (p's <0.01) FIG. 27D.

Example 16

Figure 28:
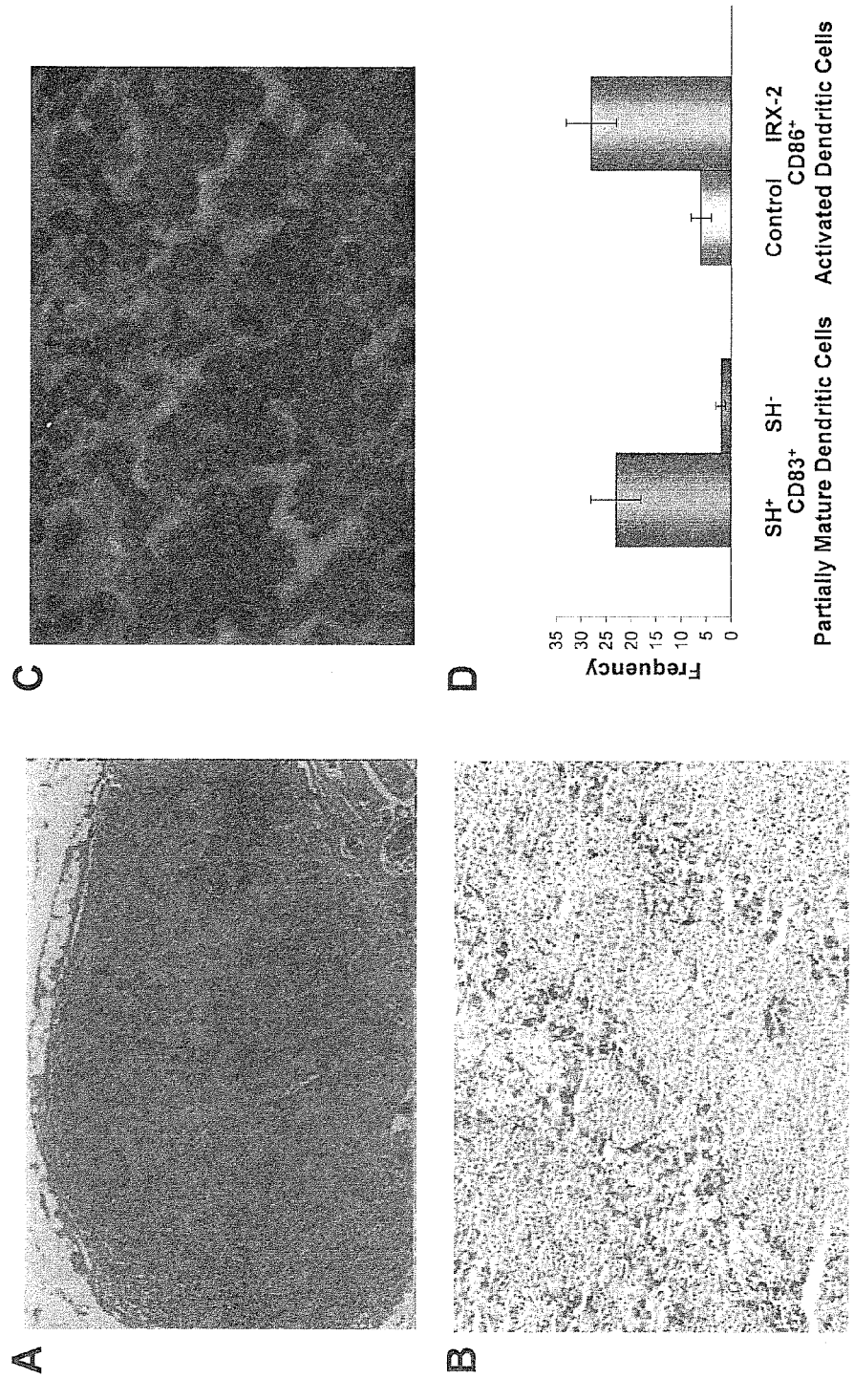
FIG. 28A is a photograph of H&E staining of a typical lymph node in a head and neck cancer patient with sinus histiocytosis.
FIG. 28B is a photograph of H&E and CD68 staining of a typical lymph node in a head and neck cancer patient with sinus histiocytosis.
FIG. 28C is a photograph of H&E staining of a lymph node with erythrocyte congestion in a head and neck cancer patient with sinus histiocytosis.
FIG. 28D is graph showing that IRX-2 treatment increases the number of activated dendritic cells in lymph nodes.
Figure 29:
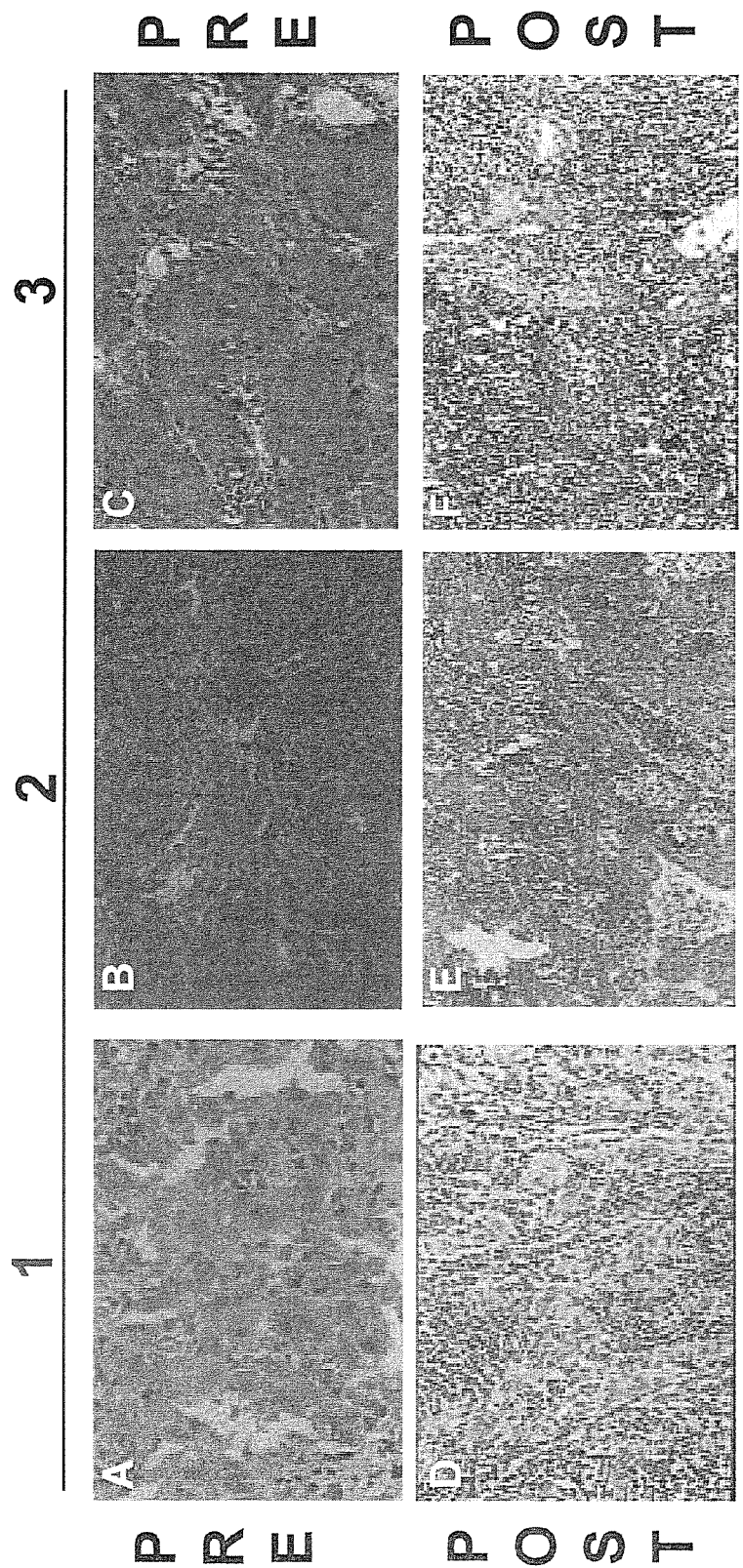
FIGS. 29A-C are photographs of H&E staining of tumor samples of patients with head and neck cancer showing a lack of lymphocyte infiltration.
FIGS. 29D-F are photographs of H&E staining of tumor samples of patients with head and neck cancer after IRX-2 treatment showing a lack of lymphocyte infiltration.

FIGS. 28A-D—Sinus histiocytosis is characterized by the majority of cells being large, granular, PAS-positive and a minority of CD3+ T cells of varying size. FIG. 28A depicts a typical example of a HN SCC control with Sinus Histiocytosis. FIG. 28B shows CD68+ staining of a lymph node with Sinus Treatment with IRX-2 was associated with a reversal of sinus histiocytosis apparent in the HN SCC controls. FIG. 28C shows a typical example of a lymph node with sinus histiocytosis and erythrocyte congestion. FIG. 28D is a bar graph showing the reversal of sinus histiocytosis in IRX-2 treated patients.

Example 17

FIGS. 29A-F—The upper panel shows examples of the pre-treatment biopsy of three patients with squamous cell head and neck cancer (H&N SCC). The biopsies average 80% tumor and 20% stroma with a light sprinkling of lymphocytes in the stroma. The lower panel shows typical sections of the tumor following treatment with the IRX-2 regimen. Notable is the heavy infiltration of lymphocytes with displacement of tumor. In this trial at INCAN 22/25 patients (88%) showed the response.

Example 18

Figure 30:
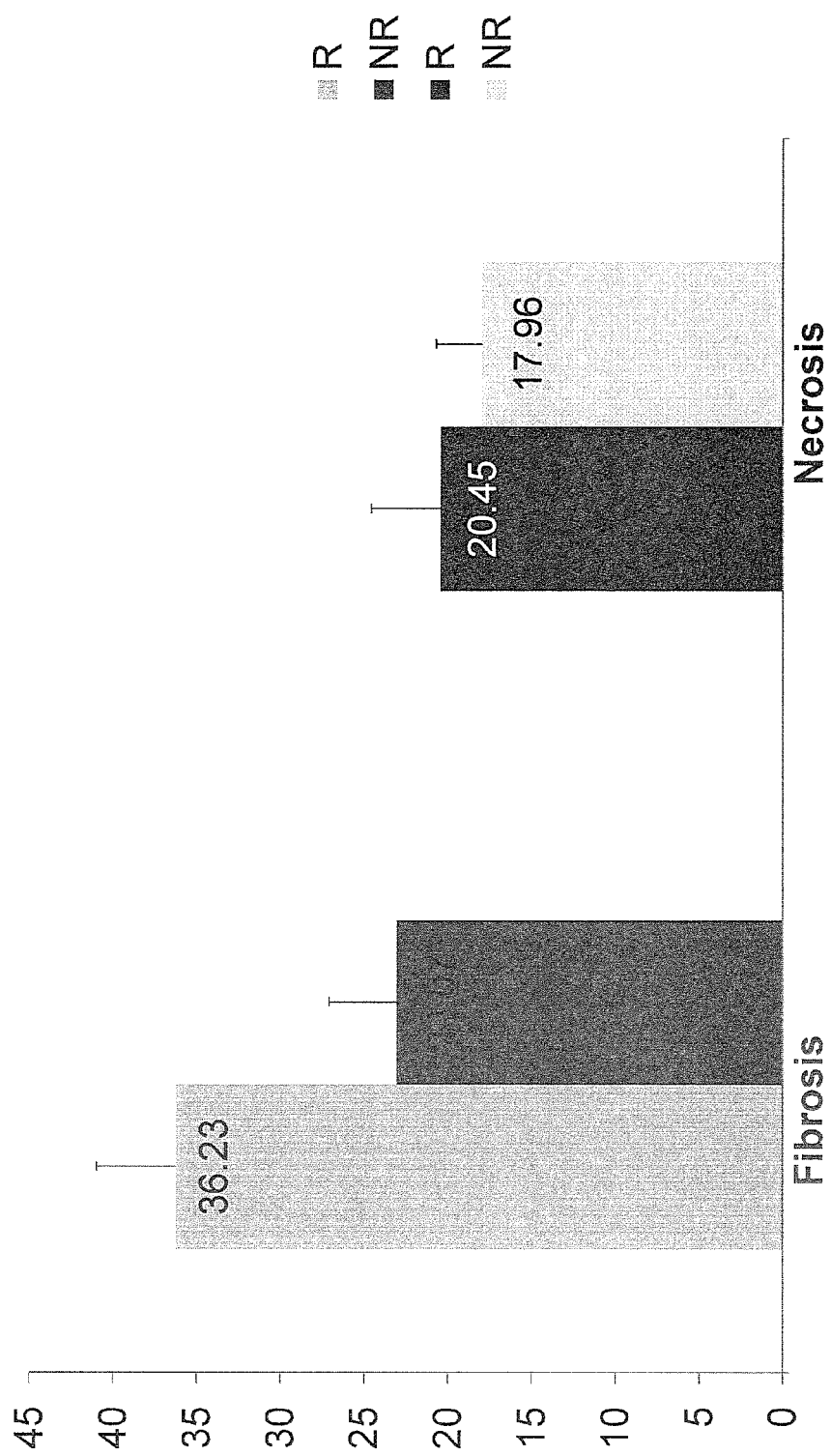
FIG. 30 is a graph of fibrosis and necrosis in responders and non-responders.
Figure 31:
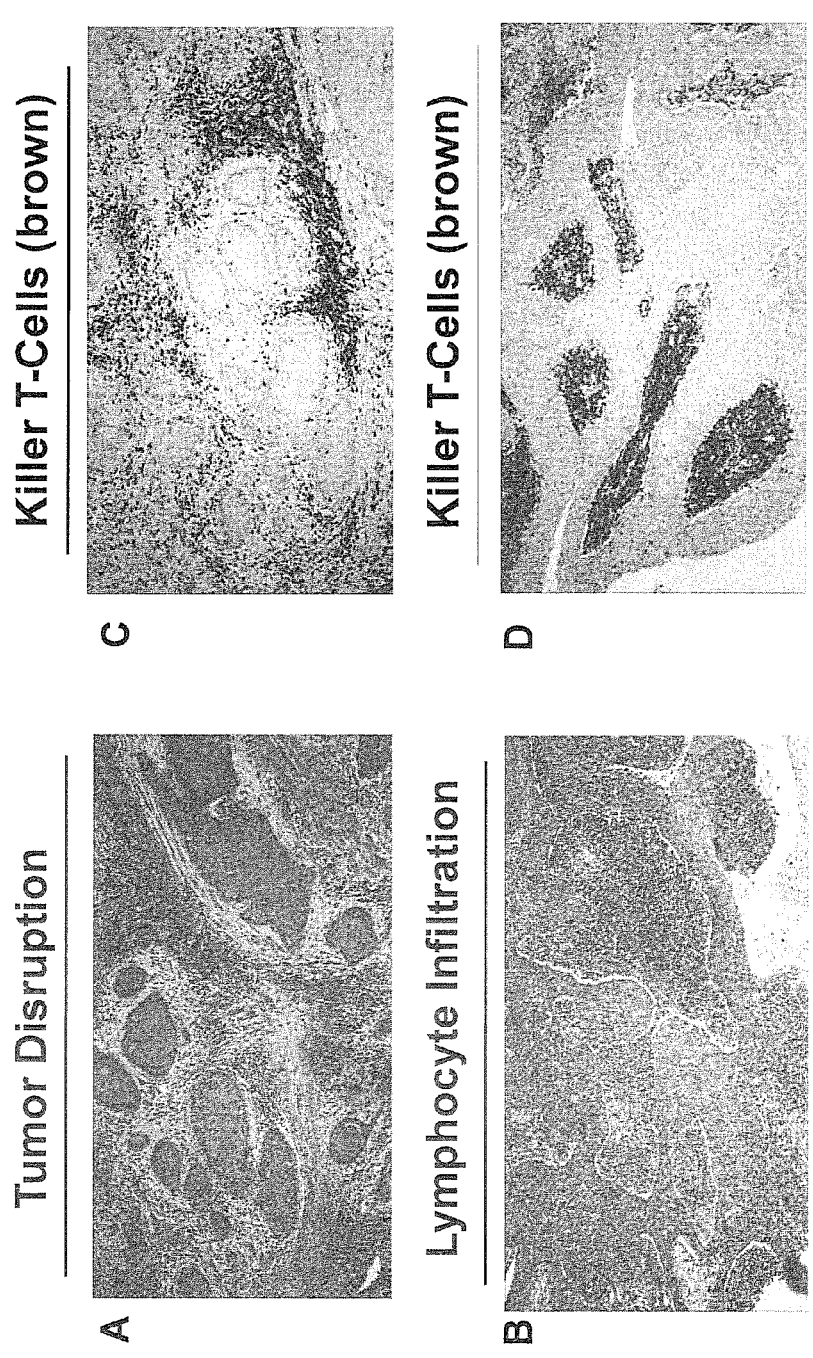
FIG. 31A is a photograph of tumor fragmentation.
FIG. 31B is a photograph of lymphocyte infiltration.
FIGS. 31C-D are photographs of killer T cells.

FIG. 30 Shows the intensity of necrosis and fibrosis in the surgical specimen of 11 responder patients (44%) vs 14 non-responder patients treated with the IRX-2 regimen in the US Phase 2 trial.

Example 19

IRX-2 is shown to stimulate killer T cell infiltration that causes tumor destruction, as shown in FIGS. 31A-D. FIGS. 31A-D are H&E and IHC (Immiochemistry) stains of resection specimens from patients treated with IRX-2. Despite the heterogeneity of tumors, there is seen an increased frequency of the brisk infiltrate pictured in FIG. 31B and noted by the arrow as a lake of lymphocytes. Pictured in FIG. 31D, the immunohistochemistry staining confirms that the infiltrate is the CD45RO memory killer T-cell phenotype. There is growing evidence that lymphocyte infiltration into tumors predicts improved outcome in colorectal, ovarian, breast, head and neck cancer. The lymphocytic infiltrate provides a link as to why patients appear to be living longer without disease than expected—the result of immune memory that can attack micro metastases and thereby delay or prevent recurrence and improve survival.

Example 20

Immunohistochemistry was performed to compare intratumoral versus peritumoral infiltrates. Summary data from the evaluation of overall presence and location of immune cells in the tumor resection specimen based on immunohistochemistry stain is presented below in Table 12. The combined presence of B cells in the tumor's peripheral area and the diffuse intratumoral lymphocytic infiltrate that is primarily CD8+ and CD45 RO+ (ie, the "killer" effector T-cell phenotype) copresent with activated CD68+ macrophages suggest antigenic stimulation and an antitumor immune response.

TABLE 12

|  | Responders | Non-Responders | P value |
| --- | --- | --- | --- |
| CD3 | 85:15 | 69:31 | <0.05 |
| CD4 | 59:41 | 49:51 | NS |
| CD8 | 93:7 | 80:20 | <0.05 |
| CD45RO | 97:3 | 79:21 | <0.01 |
| CD45RA | 32:68 | 2:98 | <0.02 |
| CD20 | 30:70 | 17:83 | NS |
| CD68 | 96:4 | 88:12 | <0.01 |

Example 21

Dendritic Cells

One of the key cell types that IRX-2 acts on is the dendritic cell. Cancer patients have reduced dendritic cell function as a result of reduced antigen uptake, antigen presentation, and expression of the signaling molecules necessary for effective T cell stimulation.

Figure 32:
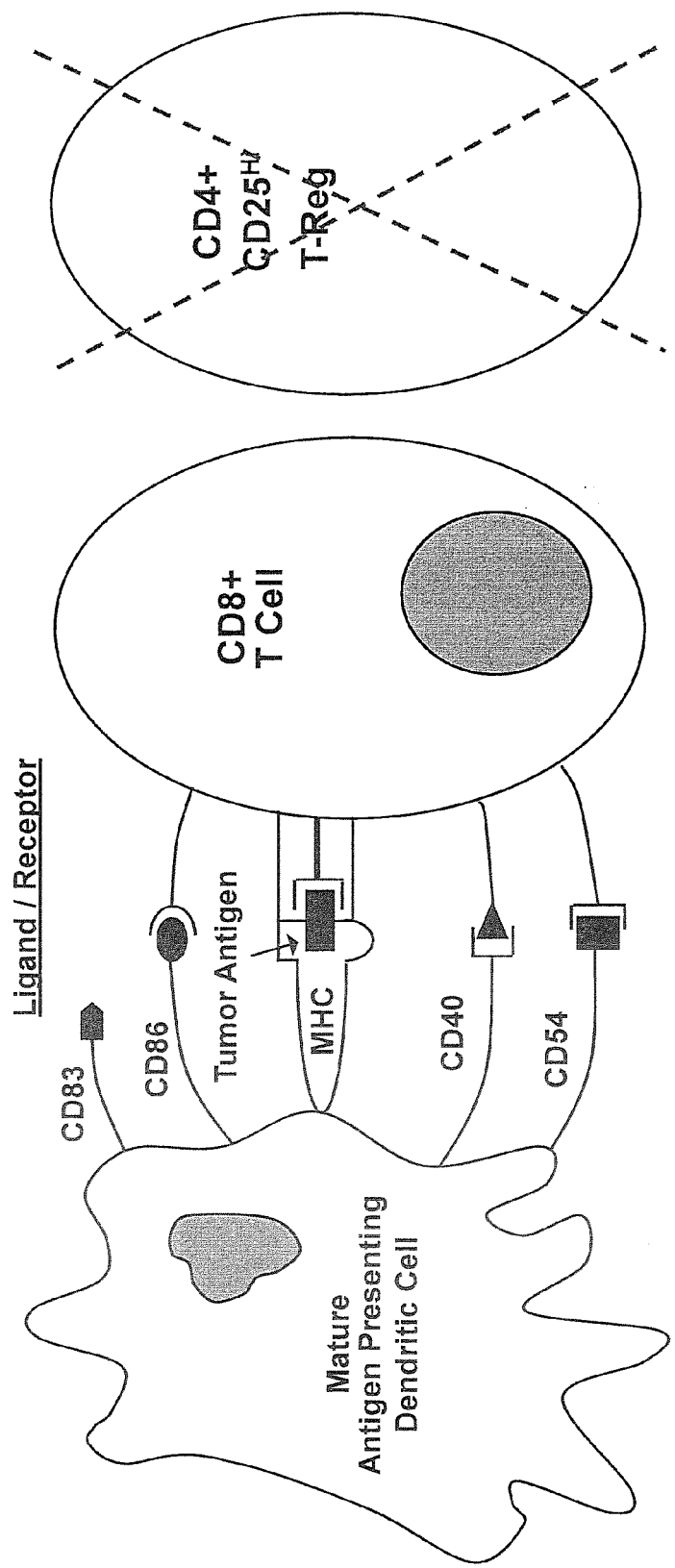
FIG. 32 is a display of the mechanism of IRX-2 restoring dendritic cell function by up-regulating key activation receptors.

As shown in FIG. 32, the key signaling molecules for T cell stimulation and adhesion on dendritic cells are CD86, CD40 and CD54. In cancer patients, the components of the antigen presenting machinery are down-regulated in dendritic cells, resulting in a reduction of effective antigen presentation to T cells. IRX-2 is able to activate and mature dendritic cells both phenotypically and functionally. By increasing expression of the antigen presenting machinery, IRX-2 acts to restore antigen presentation function.

Figure 33:
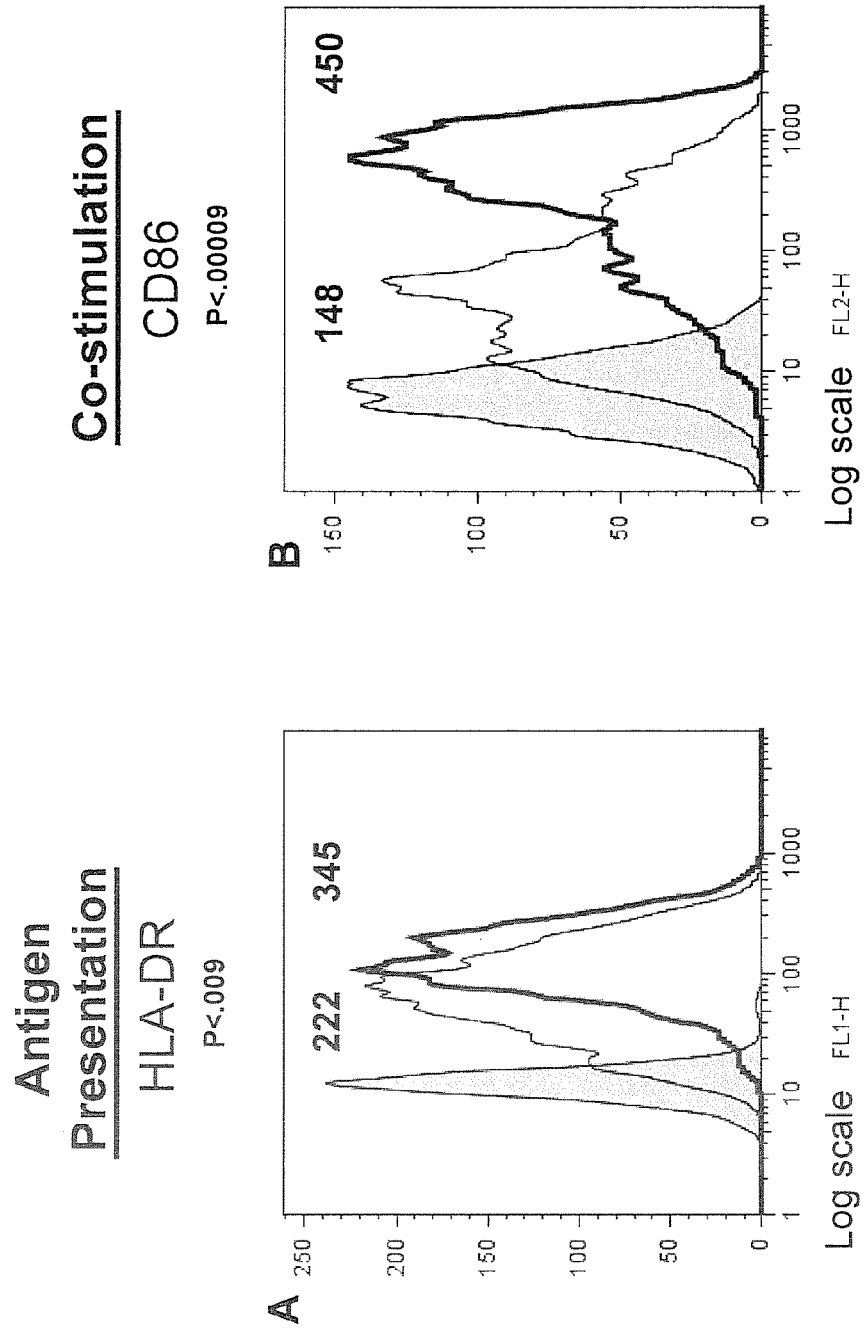
FIG. 33A is a graph of antigen presentation increase (HLA-DR) by IRX-2.
FIG. 33B is a graph of co-stimulation increase (CD86) by IRX-2.

Shown in FIG. 33 is highly statistically significant flow cytometry data that show the actions of IRX-2 on the dendritic cell's antigen presenting machinery and T cell stimulatory capacity. HLA-DR up-regulation is required by dendritic cells to present antigen in the MHC Class II groove. CD86 is the co-stimulatory receptor for naïve T-cells, that is one of the required signals for T-cell activation and the creation of killer memory T-cells. Dendritic cells that do not express CD86 are tolerizing dendritic cells and function to create antigen-specific suppressive regulatory T cells. By administering IRX-2 and increasing the co-stimulatory proteins, it is possible to shift this balance from tolerizing dendritic cells to activating dendritic cells, and a coordinated and robust immune response against the immune target is initiated.

Figure 34:
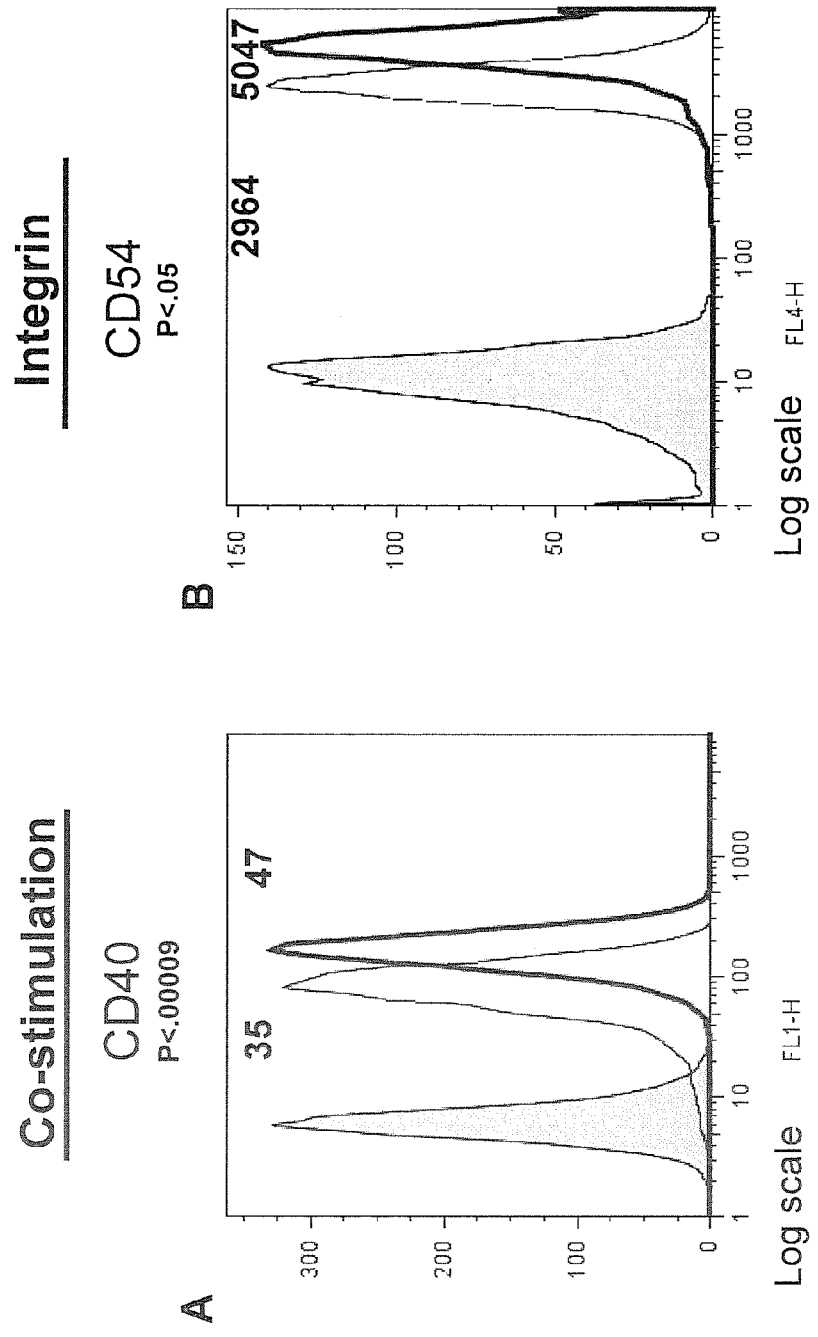
FIG. 34A is a graph of up-regulation of CD40 by IRX-2.
FIG. 34B is a graph of up-regulation of CD54 by IRX-2.
Figure 35:
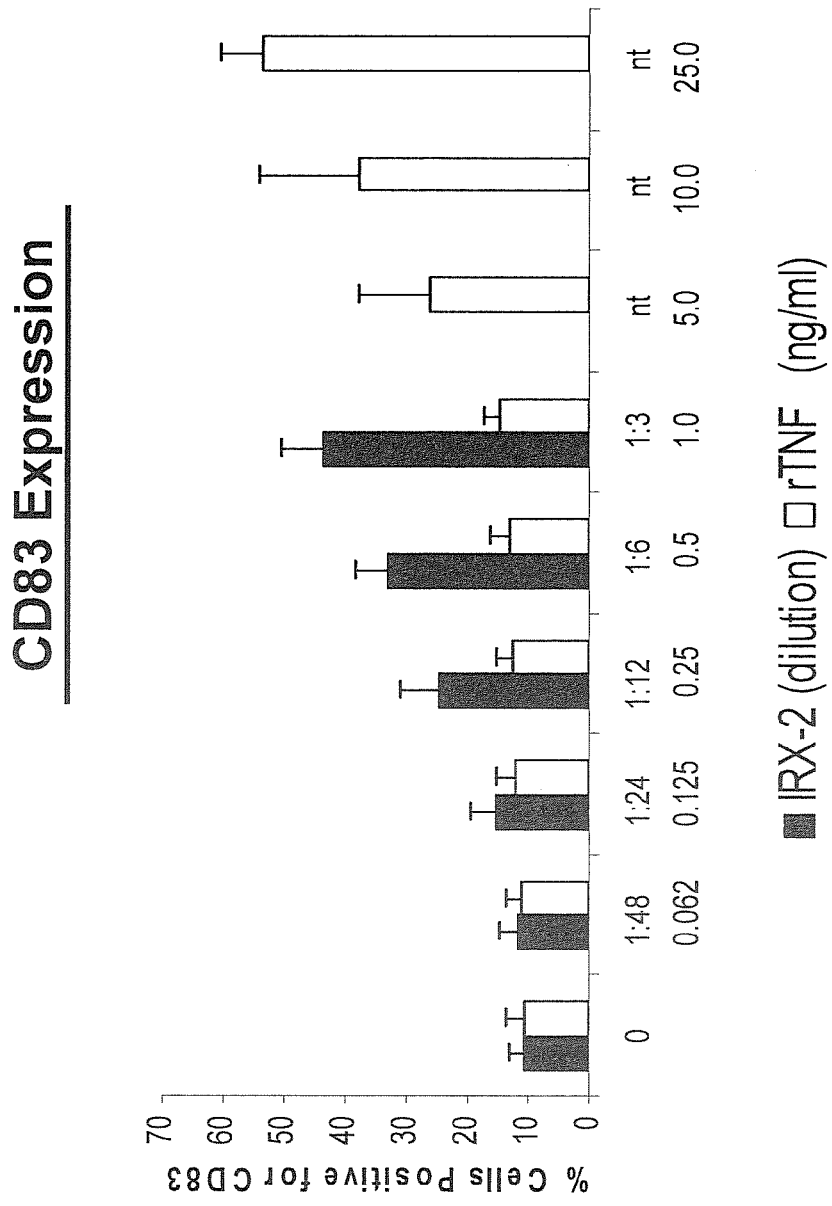
FIG. 35 is a graph of CD83 expression with IRX-2.

FIG. 34 shows highly statistically significant flow cytometry data that show the actions of IRX-2 on the dendritic cells' potential T cell stimulatory capacity. Increases in CD40 expression are necessary to generate a sustained T cell activation and generation of memory T cells. CD54 also called ICAM-1, and is involved in dendritic cell-T cell interactions and provides a second of the required signals for T-cell activation. Thus the up-regulation of these molecules in dendritic cells ensures that the cellular immune response initiated by IRX-2 is sustained and robust.

FIG. 45 shows data comparing various dilutions of IRX-2 and recombinant TNF and their respective ability to up-regulate CD83 expression, a marker of mature dendritic cells. The multiple active components in IRX-2, present in physiologic quantities, act synergistically to increase CD83 expression by about 4 times the magnitude of the equivalent amount of TNF present in IRX-2. To achieve similar results with TNF alone, 10-25 times the concentration was required, amounts that would clearly exceed the concentration in tissue or lymph node (supra-physiologic/pharmacologic).

Figure 36:
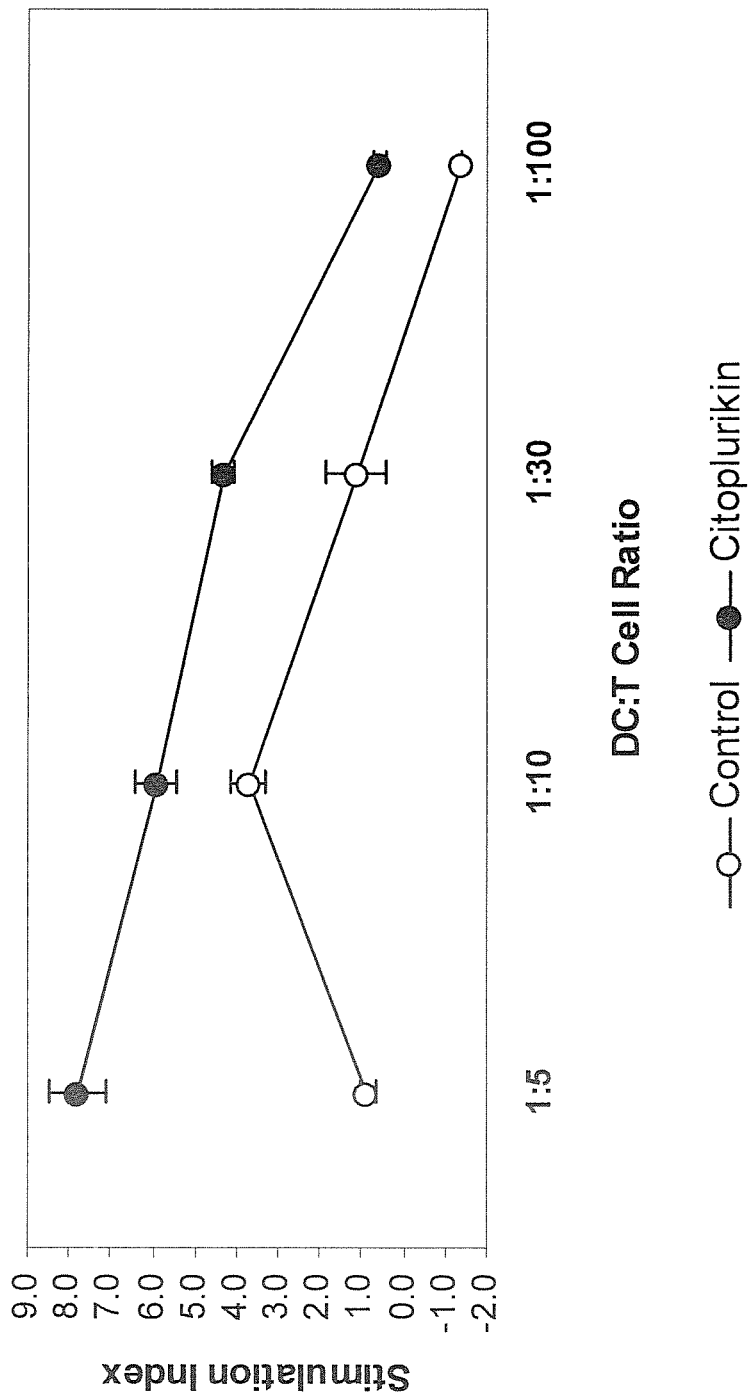
FIG. 36 is a graph of dendritic cell-mediated T cell stimulation after IRX-2 treatment.

FIG. 36 shows data from an assay to determine the ability of dendritic cell to induce T-cell proliferation, a functional assessment of a dendritic cell's ability to activate naïve T-cells. IRX-2 enhances T cell stimulatory activity of DC. Immature DC (GM-CSF/IL4×7d) were stimulated with IRX-2 or X-VIVO 10 media alone control (closed or open circles, respectively). After 48 h, DC were harvested, washed extensively and co-cultured with allogeneic nylon wool-purified T cells (2×105/well) in round bottom 96-well microtiter plates at the indicated stimulator (DC) to responder (T) ratios. On day 5 of the co-culture, cells were pulsed with BrdU and incorporated BrdU was measured 18 h later by a colorimetric anti-BrdU ELISA assay. This graph shows the results from a representative donor of 6 individual donors tested, expressed as mean stimulation index (S.I.) (+/−SEM) at the 4 DC:T ratios tested. S.I. is defined as [(O.D. DC stimulated T cell−O.D. DC alone)/O.D. resting T cell]. The mean S.I. from all 6 donors across the entire range of DC:T ratios showed a statistically significant improvement when IRX-2-treated DC were used as stimulators (p<0.05, by ANOVA). There was a significant increase in the IRX-2 treated dendritic cells ability to induce T-cell proliferation—a confirmation that the phenotypic dendritic cell changes induced by IRX-2 also results in a functionally active dendritic cell that is capable of effectively causing T cell stimulation and proliferation.

Example 22

IRX-2 Enhances Peptide-Specific IFN-γ Production and DTH

Figure 37:
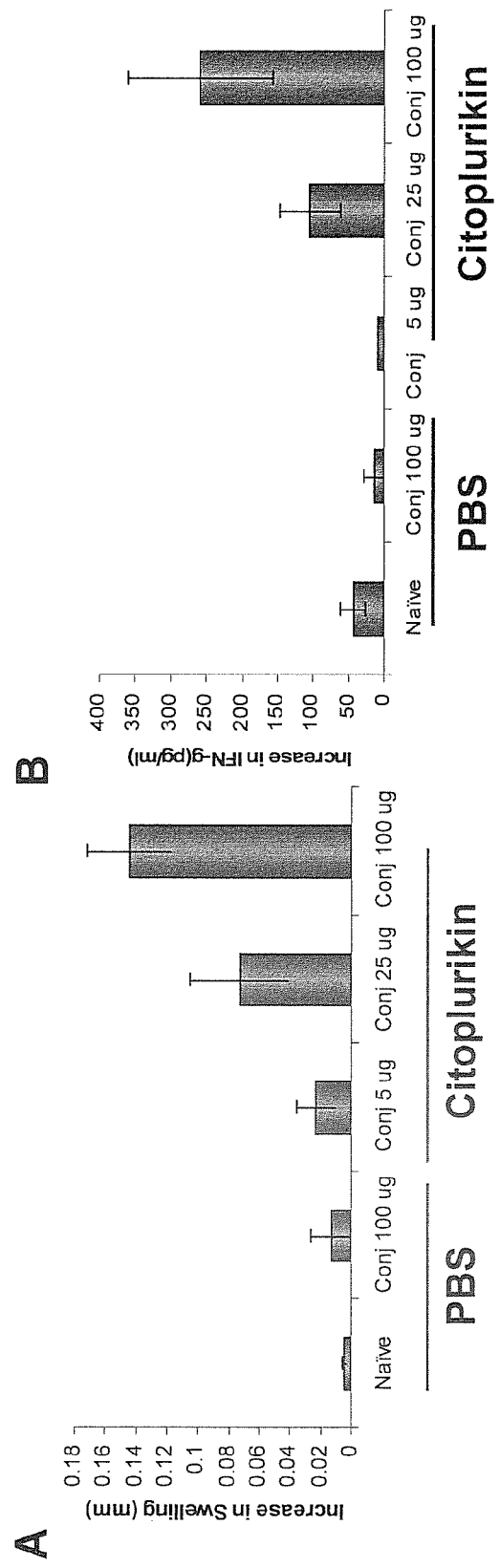
FIG. 37A is a graph of delayed type hypersensitivity and FIG. 37B is a graph of increase in IFN-γ with IRX-2.

Mice were immunized with varying doses of PSMA peptides with and without IRX-2. The T cell response after peptide or conjugate challenge was assessed by DTH response (FIG. 37A) or IFN-γ production (FIG. 37B) in response to a subsequent peptide. IRX-2 plus conjugate vaccine enhances antigen specific cellular T cell response in vivo (DTH) and ex vivo (IFN-γ production by spleen lymphocytes). This is important because a cellular response is an essential requirement in an effective cancer vaccine. Also, the T cell responses in vivo and ex vivo are both related to the dose of the vaccine used with IRX-2. The dose response confirms that the response is vaccine antigen driven and not just due to IRX-2.

Example 23

IRX-2 is Superior to Other Adjuvants in Enhancing Peptide-Specific DTH

Figure 38:
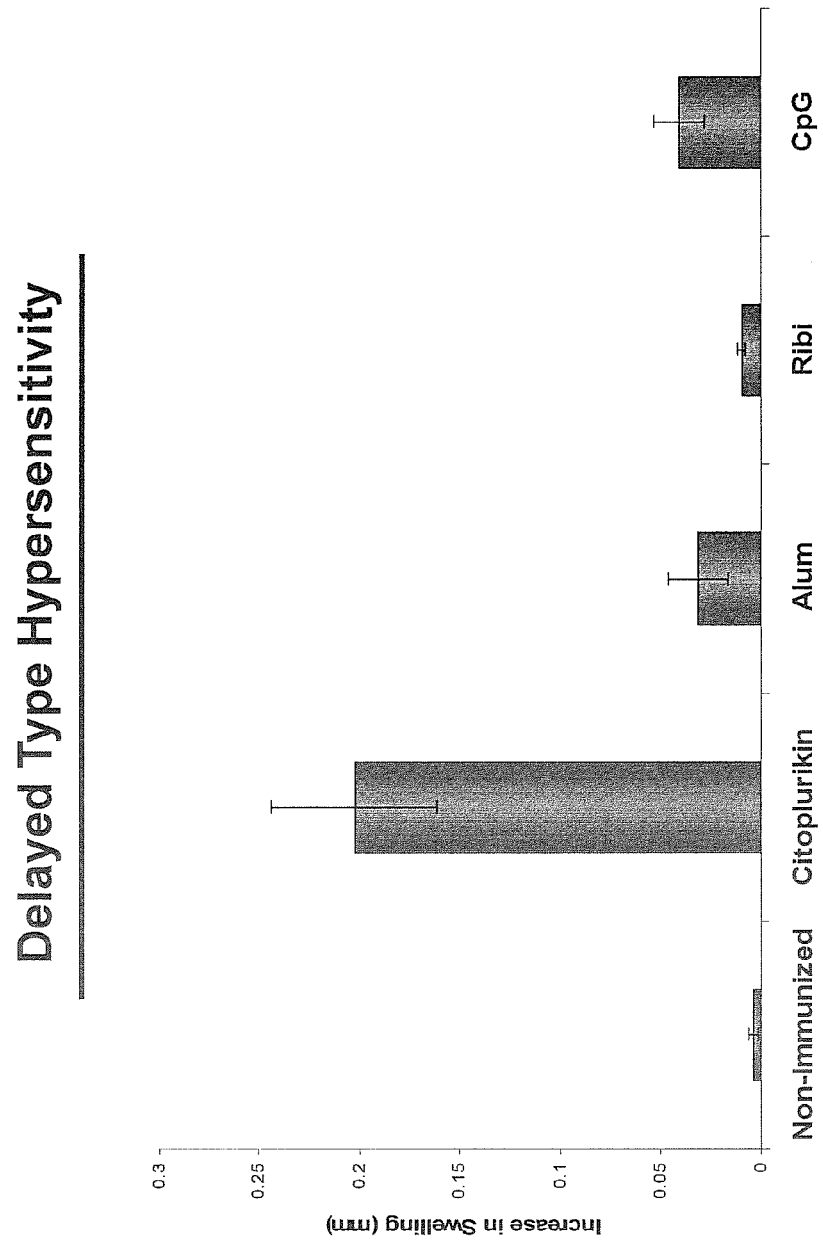
FIG. 38 is a graph of delayed type hypersensitivity compared across treatments.

The novel nature of the IRX-2 activity was confirmed by comparing IRX-2 to other adjuvants which were selected to represent various mechanisms of action. Alum was evaluated because it is a widely used FDA approved adjuvant, CpG because it is a TLR agonist that targets antigen presenting cells and the RIBI Adjuvant System (RAS) because it contains multiple adjuvant activities and is a safer alternative than Freund's adjuvant. As shown in FIG. 38 all of the adjuvants tested caused a DTH response when challenged with the conjugate; however, only IRX-2 enhanced the peptide-specific DTH response to the conjugate vaccine while alum, CpG or RAS did not as shown in FIG. 43. The studies reported here provide important preclinical data supporting the hypothesis that IRX-2 enhances T cell immune responses to exogenous antigens for use in combination with multiple antigen types in therapeutic cancer vaccines. The unique nature of the T cell peptide-specific response to the conjugate vaccine is a result of the multi-target mode of action of IRX-2 and the presumed synergy among the cytokines.

Example 24

Evidence of Action on Immune Cells in Peripheral Circulation

Figure 39:
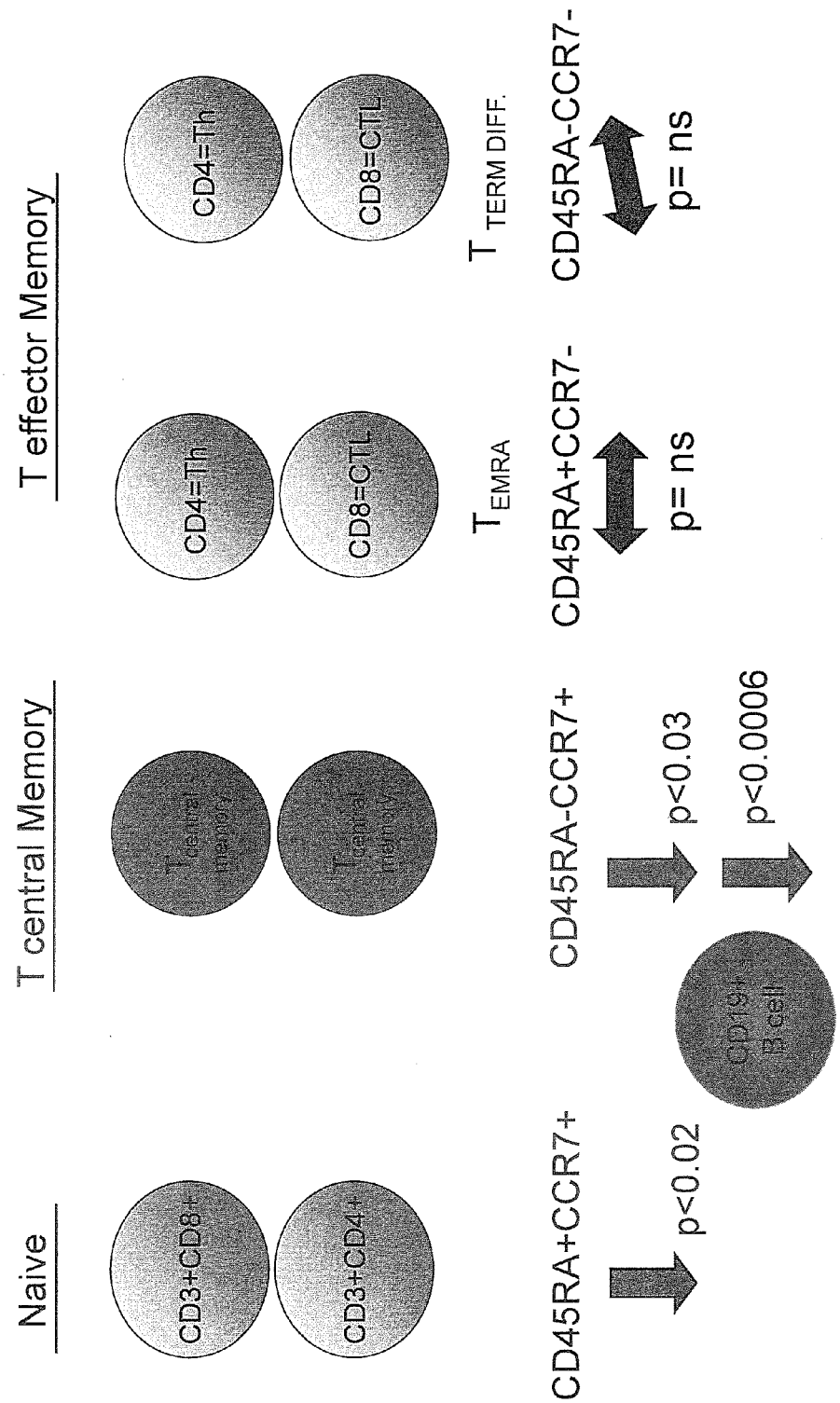
FIG. 39 is a display of evidence of action on immune cells in peripheral circulation.

The following data are summarized from immune monitoring of peripheral blood at baseline and day 21. Statistically significant decreases in peripheral blood in 21 days in the $CCR7^+$ cell populations-those with lymph node homing potential and B cells are consistent with these cells recruitment out of the circulation and into lymph nodes for activation by dendritic cells. No change or a slight trend towards increased numbers of effector cells are consistent with cytotoxic T cells that pass temporarily into the circulation and then into tissue to kill the antigenic target. The overall changes in peripheral blood of the IRX-2 regimen treated patients of both immune cells and T regulatory cells are consistent with an immunization in lymph nodes a shift from a tolerizing to a stimulating environment, as shown generally in FIG. 39.

Figure 40:
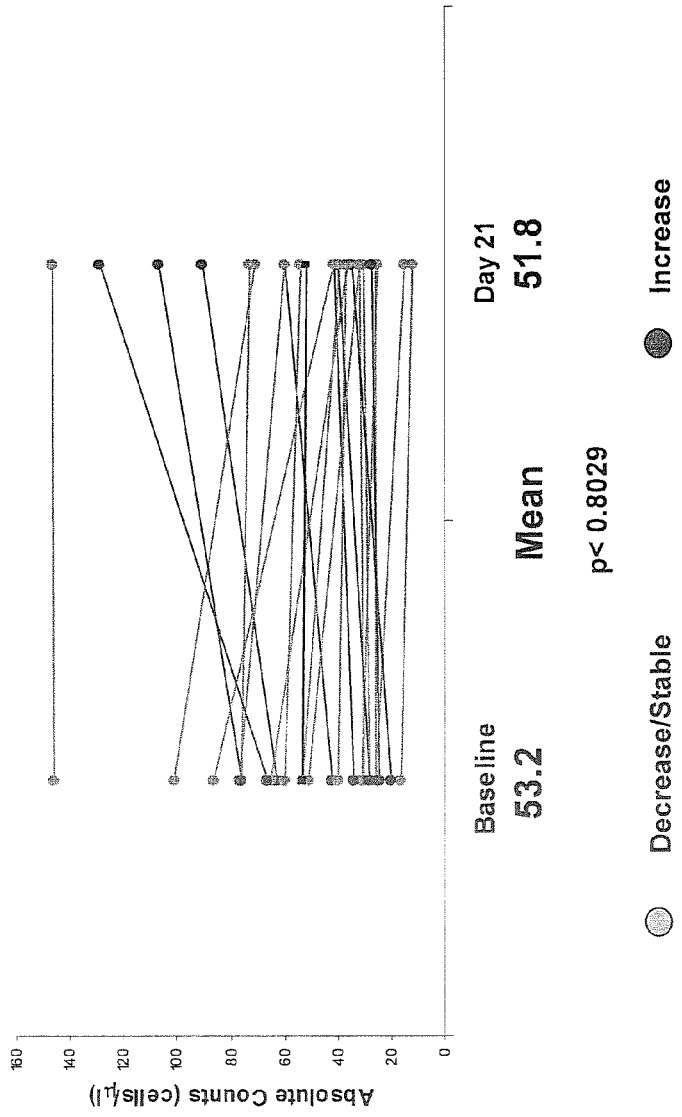
FIG. 40 is a graph of T reg counts with IRX-2 treatment.

Presented in FIG. 40 are the absolute counts at baseline and day 21 (after completion of IRX-2 regimen) of T regulatory cells in peripheral blood from Head and Neck cancer patients. Each line represents a patient and the bold line represents the group mean. Several prior studies have indicated that T reg cells are increased in cancer patients (ovarian, colorectal, hepatocellular, HNSCC) and that increased T regs is associated with a worse prognosis. The fact that the T regs of 18 of 26 patients stay the same or go down in only 21 days is a striking and significant finding because tolerizing dendritic cells should continue to expand the T reg population. The IRX-2 regimen stabilizes Treg counts at baseline levels is a significant finding reflective of improved survival in these patients.

Example 25

Evidence of Tumor Shrinkage Consistent with Immunization

Figure 41:
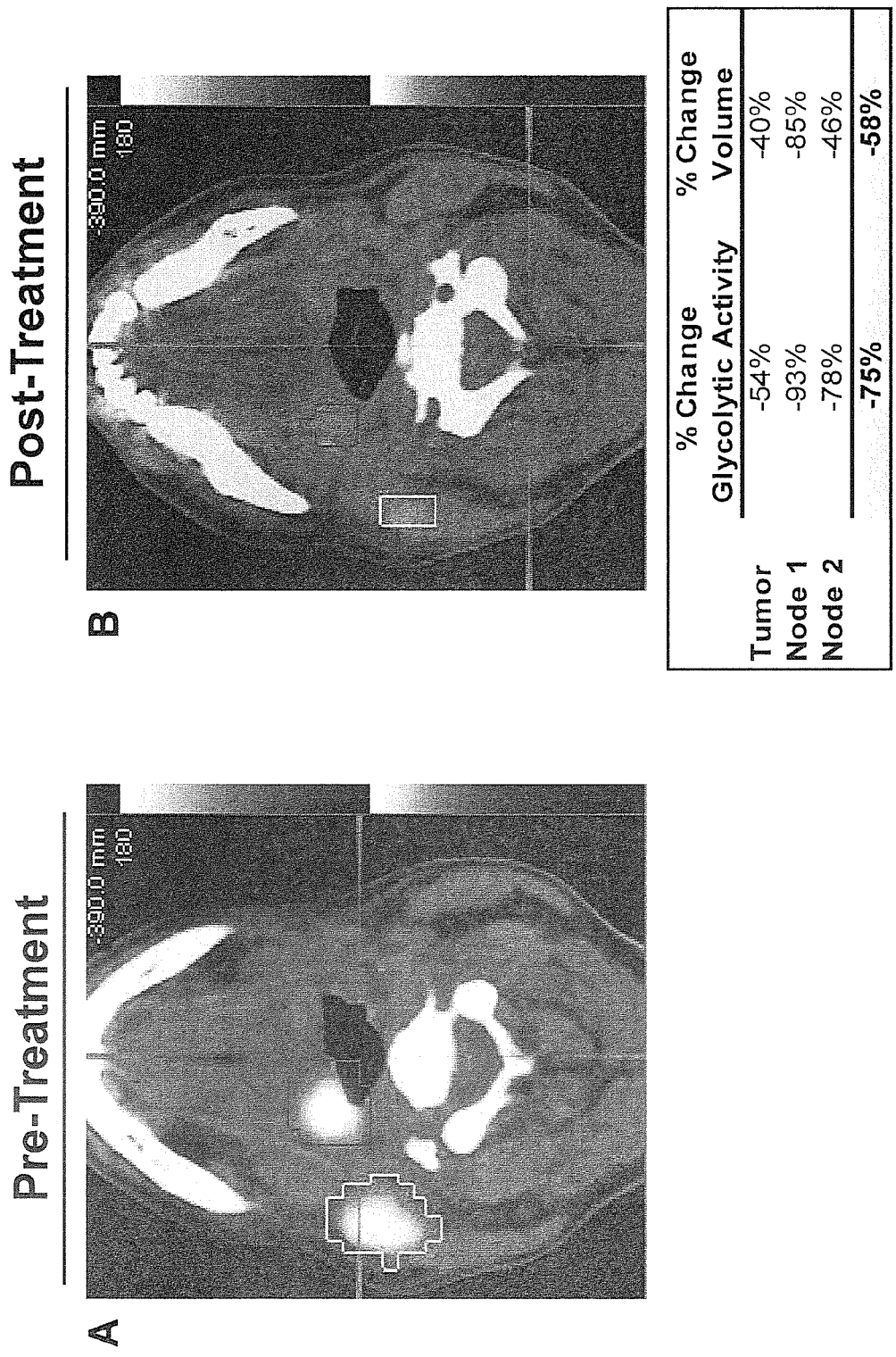
FIG. 41A is an image of a tumor pre-treatment with IRX-2.
FIG. 41B is an image of a tumor post-treatment with IRX-2.

FIGS. 41A and 41B show fused FDG-PET/CT scans of a large 5.2 cm right base of tongue primary with two involved lymph nodes shows a 58% reduction in volume and a 75% reduction in total glycolytic activity in 21 days. There is evidence of tumor shrinkage which supports the hypothesis that an anti-tumor rejection and immunization is occurring.

Example 26

Previously, the criteria for histopathology of a biopsy versus a tumor specimen (Meneses) were that the tumor was reduced overall, fragmentation of the tumor occurred, and there was increased lymphocyte infiltration (LI). According to the present invention, there are new criteria presented herein for a treated tumor versus a control tumor, namely tumor disruption with necrosis and fibrosis, and increased LI that is greater intratumorally than peritumorally. Table 13 below summarizes various findings of cytokine treatment on H&NSCC. Importantly, IRX-2 is shown to work on all arms of the immune system whereas other multiple component cytokine therapeutics do not. MULTIKINE (Cel-Sci) includes multiple cytokines in its formulation; however, its effect is a single one on the tumor itself, not on the immune system.

TABLE 13

| | Treated | Control | |
|---|---|---|---|
| De Stefani rIL-2 | Tumor | Control tumor | ↑ LI, ↑ necrosis, ↑ fibrosis |
| Meneses IRX-2 | Tumor | Biopsy | ↑ LI, ↓ tumor, ↑ fragmentation |
| Feinmesser Multikine | Tumor | Biopsy | ↑ LI, ↓ tumor |
| Timar Multikine | Tumor | Control tumor | ↑ LI, No ↓ tumor or fragmentation |
| IRX Therapeutics | Tumor | Biopsy | ↑ LI - small tumor, ↑ fragmentation |
| | Tumor | Control tumor | ↑ LI, ↑ fibrosis |

OVERALL CONCLUSION

This study confirms and extends Applicants' prior observations concerning the ability of the IRX-2 regimen to have significant biological activity on patients with squamous cell head and neck cancer treatment prior to surgery. The present study confirms that the treatment is safe with few adverse events attributed to the regimen. In fact, those patients who showed evidence of histopathologic changes of lymphocyte infiltration had the majority of symptom improvements like reduced pain and tenderness, improved breathing and phonation, and softening of the tumor (as sign of dissolution). Three patients were adjudged to have clinical responses (2PRs, 1MR). Overall survival data and recurrence free survival while immature are encouraging and similar in degree and profile to Applicants' previous study. Notable is that no deaths occurred due to recurrence in the first 12 months of follow up. All deaths to date but one are in the non-responder group.

The most compelling data are those associated with the mechanism of action studies. It was observed that declines of B lymphocytes and two T cell subsets associated with initial immunization and lymph node homing. No increases in memory/effector cell were observed in blood; however, this is explainable based upon the traffic patterns of T cells which occur with an immunization. Notably no increase in T regs was observed.

Applicants' prior studies showed that patients responding to the IRX-2 regimen show increase of uninvolved lymph nodes proximal to the tumor, replenishment of depleted T lymphocyte areas and the picture of activation as occurs with antigen. Thus, lymphocytes are trafficking via blood and lymphatics to the regional lymph nodes where they are presumably immunized to autologous tumor antigens. As shown herein, they then leave the lymph node and travel by blood to the tumor where they infiltrate in and around the tumor and correlate with evidence of tumor destruction (necrosis, fibrosis, and tumor reduction). In the patients showing this reaction, the increases in lymphocyte infiltration involves predominantly CD3+ CD4+ CD45RA+ T cell populations and CD20+ B lymphocytes around the tumor periphery and CD3+ CD8+ CD45RO+ T lymphocyte populations and macrophages within the tumor. The changes within the tumor are greater than these in the periphery. This mechanism is generally shown in FIG. 2.

Notably, untreated patients show such a reaction only occasionally (20%) and while significantly less frequently than patients treated with the IRX-2 regimen (44% vs. 20%) the presence of the reaction in controls represent a new biomarker for predicting favorable outcome.

The picture is an integrated one clinically, radiologically, pathologically, and immunologically and provides ample evidence for an immunization to autologous tumor antigen. IRX-2 is shown to activate all arms of the immune system to provide a total restoration of immune function and ability to attack immune targets.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

REFERENCES

Dunn G, et al. Dendritic cells and HNSCC: A potential treatment option? (Review). Oncology Reports 13:3-10, 2005.
Egan J E, et al. IRX-2, a novel in vivo immunotherapeutic, induces maturation and activation of human dendritic cells in vitro. J Immunother 30:624-633, 2007.
Galon J, et al. Type, density, and location of immune cells within human colorectal tumors predict clinical outcome. Science 313:1960, 2006.
Hadden J W, et al. Immunotherapy with natural interleukins and/or thymosin alpha 1, potently augments T-lymphocyte responses of hydrocortisone-treated aged mice. Int J Immunopharm 17(10):821-828, 1995.
Hadden J W, et al. Zinc induces thymulin secretion from human thymic epithelial cells in vitro and augments splenocytes and thymocyte responses in vivo. Int J. Immunopharm 17(9):729-733, 1995.
Kaech S M, et al. Effector and memory T-cell differentiation: implications for vaccine development. Nature Rev Immunol 2:251, 2001.
Lanzavecchia A, et al. Understanding the generation and function of memory T cell subsets. Curr Opin Immunol 17:326, 2005.
Maass G, et al. Priming of tumor-specific T cells in the draining lymph nodes after immunization with interleukin-2-secreting tumor cells: Three consecutive stages may be required for successful tumor vaccination. Proc Natl Acad Sci 92:5540, 1995.

Mantovani A, et al. Macrophage polarization: tumor associated macrophages as a paradigm for polarized M2 mononuclear phagocytes. Trends in Immunology, 23 (11) 2002.

Meneses A, et al. Lymph node histology in head and neck cancer: impact of immunotherapy with IRX-2. Intl Immunopharm. 3:1083-1091, 2003.

Pages F, et al. Effector memory T cells, early metastasis, and survival in colorectal cancer. NEJM 353:2654-66, 2005.

Sallusto F, et al. Two subsets of memory T lymphocytes with distinct homing potentials and effector functions. Nature 401:708, 1999.

Tomiyama H, et al. Phenotypic classification of human CD8+ T cells reflecting their function: inverse correlation between quantitative expression of CD27 and cytotoxic effector function. Eur J Immunol 34:999, 2004.

Verastegui E, et al. Immunological approach in the evaluation of regional lymph nodes of patients with squamous cell carcinoma of the head and neck. Clin Immunol 102:37, 2002.

Whiteside T L. Immunobiology and immunotherapy of head and neck cancer. Curr Onc Reports 3:46-55, 2001.

Wolf G T, et al. Lymphocyte subpopulations infiltration squamous carcinomas of the head and neck: correlations with extent and tumor prognosis. Otolaryngol Head Neck Surg 95:145, 1986.

What is claimed is:

1. In a method of cytoprotective cancer therapy, the improvement comprising ex-vivo pre-incubation of T cells from a patient with an effective amount of a primary cell derived biologic, prior to administering said T cells to the patient.

2. The method of claim 1 wherein the primary cell derived biologic comprises interleukin 1beta (IL-1beta), interleukin 2(IL-2), interleukin 6 (IL-6), interleukin 8 (IL-8), tumor necrosis factor alpha (TNF-alpha), and interferon-gamma (IFN-gamma).

3. The method of claim 1, wherein the T cells are primary blood-derived T cells from the patient.

4. The method of claim 3, wherein the T cells comprise CD4 positive T cells.

5. The method of claim 3, wherein the T cells comprise CD8 positive T cells.

* * * * *